United States Patent
Gallo et al.

(10) Patent No.: US 9,914,929 B2
(45) Date of Patent: Mar. 13, 2018

(54) GENERATING TARGETED SEQUENCE DIVERSITY IN FUSION PROTEINS

(71) Applicant: Innovative Targeting Solutions Inc., Vancouver (CA)

(72) Inventors: Michael Gallo, North Vancouver (CA); Jaspal Singh Kang, Surrey (CA); Craig Robin Pigott, Vancouver (CA)

(73) Assignee: Innovative Targeting Solutions Inc., Burnaby (CA)

( * ) Notice: Subject to any disclaimer, the term of this patent is extended or adjusted under 35 U.S.C. 154(b) by 347 days.

(21) Appl. No.: 14/384,758

(22) PCT Filed: Mar. 14, 2013

(86) PCT No.: PCT/CA2013/050204
§ 371 (c)(1),
(2) Date: Sep. 12, 2014

(87) PCT Pub. No.: WO2013/134881
PCT Pub. Date: Sep. 19, 2013

(65) Prior Publication Data
US 2015/0240243 A1    Aug. 27, 2015

Related U.S. Application Data

(60) Provisional application No. 61/610,797, filed on Mar. 14, 2012, provisional application No. 61/731,988, filed on Nov. 30, 2012.

(51) Int. Cl.
| | |
|---|---|
| *C12P 21/00* | (2006.01) |
| *C12N 15/62* | (2006.01) |
| *C07K 14/605* | (2006.01) |
| *C07K 16/28* | (2006.01) |
| *C07K 16/32* | (2006.01) |
| *C12N 15/85* | (2006.01) |
| *C07K 14/52* | (2006.01) |
| *C07K 14/54* | (2006.01) |
| *C07K 14/575* | (2006.01) |
| *C07K 14/71* | (2006.01) |
| *C07K 14/78* | (2006.01) |
| *C07K 14/47* | (2006.01) |
| *C07K 16/00* | (2006.01) |

(52) U.S. Cl.
CPC ........ *C12N 15/625* (2013.01); *C07K 14/4723* (2013.01); *C07K 14/522* (2013.01); *C07K 14/5421* (2013.01); *C07K 14/57563* (2013.01); *C07K 14/605* (2013.01); *C07K 14/71* (2013.01); *C07K 14/78* (2013.01); *C07K 16/00* (2013.01); *C07K 16/2839* (2013.01); *C07K 16/2866* (2013.01); *C07K 16/2869* (2013.01); *C07K 16/32* (2013.01); *C12N 15/62* (2013.01); *C12N 15/85* (2013.01); *C07K 2317/565* (2013.01); *C07K 2318/10* (2013.01); *C07K 2319/00* (2013.01); *C07K 2319/01* (2013.01); *C07K 2319/03* (2013.01); *C12N 2800/30* (2013.01)

(58) Field of Classification Search
None
See application file for complete search history.

(56) References Cited

U.S. PATENT DOCUMENTS

| | | | |
|---|---|---|---|
| 5,756,323 A | 5/1998 | Kallenbach et al. | |
| 6,242,236 B1 | 6/2001 | Wohlstadter | |
| 8,012,714 B2 | 9/2011 | Gallo et al. | |
| 2006/0275288 A1 | 12/2006 | Grihalde et al. | |
| 2007/0060512 A1 | 3/2007 | Sadeghi et al. | |
| 2009/0130110 A1 | 5/2009 | Babcock et al. | |
| 2015/0329850 A1* | 11/2015 | Gallo ................... C07K 14/78 435/455 |

FOREIGN PATENT DOCUMENTS

| | | |
|---|---|---|
| WO | 1993/12228 A1 | 6/1993 |
| WO | 2005/060642 A2 | 7/2005 |
| WO | 2005060642 | 7/2005 |
| WO | 2009/129247 A2 | 10/2009 |
| WO | 2011109784 | 9/2011 |
| WO | 2012/018764 A1 | 2/2012 |
| WO | 2013134880 | 9/2013 |

OTHER PUBLICATIONS

Alajez et al., "Cloning and Expression of Human Membrane-Bound and Soluble Engineered T Cell Receptors for Immunotherapy," Journal of Biomedicine and Biotechnology, vol. 2006, pp. 1-9, (2006).
Couvineau et al., "VPAC Receptors: Structure, Molecular Pharmacology and Interaction with Accessory Proteins," British Journal of Pharmacology, vol. 166, pp. 42-50 (2012).
Harmar et al., "Family-B G-Protein-Coupled Receptors," Genome Biology, vol. 2, No. 12 (2001).
Kieffer et al., "The Glucagon-Like Peptides," Endocrine Reviews, vol. 20, No. 6, pp. 876-913 (1999).
Rolz et al., "Molecular Characterization of the Receptor-Ligand Complex for Parathyroid Hormone," Biochemistry, vol. 38, pp. 6397-6405 (1999).
Zhang et al., "Genome-wide Analysis of cAMP-Response Element Binding Protein Occupancy, Phosphorylation, and Target Gene Activation in Human Tissues," PNAS, vol. 102, No. 12, pp. 4459-4464 (2005).
International Search Report and Written Opinion for International Application No. PCT/CA2014/051167, dated Mar. 10, 2015, 10 pages.

(Continued)

*Primary Examiner* — Michael Burkhart
(74) *Attorney, Agent, or Firm* — Thompson Coburn LLP

(57) ABSTRACT

Methods of generating fusion protein variants are provided that comprise introducing sequence diversity at the junction region or regions in the fusion and allows for the generation of variants having a desired activity. Examples include immunoglobulins comprising a domain or polypeptide inserted into, or replacing, a CDR. Also provided are polynucleotides encoding a fusion protein and comprising two or more RSSs, and compositions and host cells comprising same, as well as fusion proteins variants produced by the described methods.

17 Claims, 17 Drawing Sheets

(56) References Cited

OTHER PUBLICATIONS

Nguyen, Final Office Action issued in U.S. Appl. No. 14/384,772, entitled "Generating Targeted Sequence Diversity in Proteins," dated Nov. 16, 2016, 23 pages.
Verhoeyen et al., "Reshaping Human Antibodies: Grafting an Antilysozyme Activity," Science, 1988, pp. 1534-1536, vol. 239.
Wollscheid et al., "Lipid Raft Proteins and Their Identification in T. Lymphocytes," Subcellular Biochemistry, vol. 37: Membrane Dynamics and Domains, 2004, pp. 121-152, Chapter 3.
Yang et al., "CDR Walking Mutagenesis for the Affinity Maturation of a Ptent Human Anti-HIV-1 Antibody into the Picomolar Range," Journal of Molecular Biology, 1995, pp. 392-403, vol. 254.
Zanetti et al., "Expression of Conformationally Constrained Adhesion Peptide in an Antibody CDR Loop and Inhibition of Natural Killer Cell Cytotoxic Activity by an Antibody Antigenized with the RGD Motif," The EMBO Journal, 1993, pp. 4375-4384, vol. 12, No. 11.
Zeytun et al., "Fluorobodies combine GFP Fluorescence with the Binding Characteristics of Antibodies," Nature Biotechnology, 2003, pp. 1473-1479, vol. 21, No. 12.
Akamatsu et al., "Essential Residues in V(D)J Recombination Signals," The Journal of Immunology, vol. 153, pp. 4520-4529 (1994).
Allgood et al., "Chimeric Receptors as Gene Switches," Current Opinion in Biotechnology, vol. 8, pp. 474-479 (1997).
Baubonis et al., "Genomic Targeting with Purified Cre Recombinase," Nucleic Acids Research, vol. 21, No. 9, pp. 2025-2029 (1993).
Bentolila et al., "Constituitive Expression of Terminal Deoxynucleotidyl Transferase in Transgenic Mice is Sufficient for N Region Diversity to Occur at Any Ig Locus Throughout B Cell Differentiation," The Journal of Immunology, vol. 158, pp. 715-723 (1997).
Bernath et al., "Directed Evolution of Protein Inhibitors of DNA-Nucleases by In Vitro Compartmentalization (IVC) and Nano-Droplet Delivery," Journal of Molecular Biology, vol. 345, pp. 1015-1026 (2005).
Binz et al., "Engineering Novel Binding Proteins from Nonimmunoglobulin Domains," Nature Biotechnology, 2005, pp. 1257-1268, vol. 23, No. 10.
Browman et al., "The SPFH Domain-Containing Proteins: More Than Lipid Raft Markers," Trends in Cell Biology, 2007, pp. 394-402, vol. 17, No. 8.
Carra et al., "Variation of the Half-Site Organization and DNA Looping by AraC Protein," The EMBO Journal, 1993, pp. 35-44, vol. 12, No. 1.
Casillas et al., "RAG-1 and RAG-2 Gene Expression and V(D)J Recombinase Activity are Enhanced by Protein Phosphatase 1 and 2A Inhibition in Lymphocyte Cell Lines," Molecular Immunology, 1995, pp. 167-175, vol. 32, No. 3.
Certo et al., "Coupling Endonucleases with DNA End-Processing Enzymes to Drive Gene Disruption," Nature Methods, 2012, pp. 973-975, vol. 9, No. 10.
Chatterjee et al., "The GPI-Anchor and Protein Sorting," Cellular and Molecular Life Sciences, 2001, pp. 1969-1987, vol. 58.
Chen et al., "Immunoglobulin G Expression in Carcinomas and Cancer Cell lines," The FASEB Journal, 2007, pp. 2931-2938, vol. 21.
Colas et al., "Genetic Election of Peptide Aptamers that Recognize and Inhibit Cyclin-Dependent Kinase 2," Letters to Nature, 1996, pp. 548-550, vol. 380, No. 6574.
Cowell et al., "Computational Tools for Understanding Sequence Variability in Recombination Signals," Immunological Reviews, 2004, pp. 57-69, vol. 200.
Dudley et al., "Mechanism and Control of V(D)J Recombination Versus Class Switch Recombination: Similarities and Differences," Advances in Immunology, 2005, pp. 43-112, vol. 86.
Zheng et al., Expression and Secretion of Immunoglobulin Alpha Heavy Chain with diverse VDJ Recombinations by Human Epithelial Cancer Cells, Molecular Immunology, 2007, pp. 2221-2227, vol. 44.
Engler et al., "Influence of CpG Methylation and Target Spacing on V(D)J Recombination in a Transgenic Substrate," Molecular and Cellular Biology, 1993, pp. 571-577, vol. 13, No. 1.
Extended European Search Report for European Application No. 13760461.7 dated Sep. 15, 2015.
Extended European Search Report for European Application No. 13761957.3 dated Dec. 21, 2015.
Fanning et al., "Mouse RSS Spacer Sequences Affect the Rate of V(D)J Recombination," Immunogenetics, 1996, pp. 146-150, vol. 44.
Ford et al., "Fusion Tails for the Recovery and Purification of Recombinant Proteins," Protein Expression and Purification, 1991, pp. 95-107, vol. 2.
Frederickson et al., "A Rationally Designed Agonist Antibody Fragment that Functionally Mimics Thrombopoietin," Proceeding s of the National Academy of Sciences, 2006, pp. 14307-14312, vol. 103, No. 39.
Fukushige et al., "Genomic Targeting with a Positive-Selection lox Integration Vector Allows Highly Reproducible Gene Expression in Mammalian Cells," Proceedings of the National Academy of Sciences, 1992, pp. 7905-7909, vol. 39.
Gauss et al., "V(D)J Recombination Activity in Human Hematopoietic Cells: Correlation with Developmental Stage and Genome Stability," European Journal of Immunology, 1998, pp. 351-358, vol. 28.
Gebauer et al., "Engineered Protein Scaffolds as Next-Generation Antibody Therapeutics," Current Opinion in Chemical Biology, 2009, pp. 245-255, vol. 13.
Griffiths et al., "Isolation of High Affinity Human Antibodies Directly from Large Synthetic Repertoires," The EMBO Journal, 1994, pp. 3245-3260, vol. 13, No. 14.
Guzman et al., "Tight Regulation, Modulation, and High-Level Expression by Vectors Containing the Arabinose P BAD Promoter," Journal of Bacteriology, 1995, pp. 4121-4130, vol. 177, No. 14.
Hackel et al., "Picomolar Affinity Fibronectin Domains Engineered Utilizing Loop Length Diversity, Recursive Mutagenesis, and Loop Shuffling," Journal of Molecular Biology, 2008, pp. 1238-1252, vol. 381.
Haldimann et al., "Use of New Methods for Construction of Tightly Regulated Arabinose and Rhamnose Promoter Fusion in Studies of the *Escherichia coli* Phosphate Regulon," Journal of Bacteriology, 1998, pp. 1277-1286, vol. 180, No. 5.
Harder, "Lipid Raft Domains and Proteins Networks in T-Cell Receptor Signal Transduction", Current Opinion in Immunology, 2014, 353-359, vol. 16.
Hattori et al., "Grafting of Material-Binding Function Into Antibodies Functionalization by Peptide Grafting," Biochemical and Biophysical Research Communications, 2008, pp. 751-757, vol. 365.
Hattori et al., "High Affinity-inorganic Material Antibody Generation by Integrating Graft and Evolution Technologies," The Journal of Biological Chemistry, 2010, pp. 7784-7793, vol. 285, No. 10.
Hayashi et al., "The Potential Role of Sigma-1 Receptors in Lipid Transport and Lipid Raft Constitution in the Brain: Implication for Drug Abuse," Life Sciences, 2005, pp. 1612-1624, vol. 77.
Heckmann et al., "Design and Chemical Synthesis of Integrin Ligands," Methods in Enzymology, 2007, pp. 463-503, vol. 426.
Heese et al., "V(D)J Recombination: A Functional Definition of the Joining Signals," Genes & Development, 1989, pp. 1053-1061, vol. 3.
Heuck et al., "Pore-Forming Protein Structure Analysis in Membranes Using Multiple Independent Fluorescence Techniques," Cell Biochemistry and Biophysics, 2002, pp. 89-101, vol. 36.
Hikida et al., "Rearrangement of . Light Chain Genes in Mature B Cells In Vitro and In Vitro. Function of Reexpressed Recombination-activating Gene (RAG) Products," The Journal Experimental Medicine, 1998, pp. 795-799, vol. 187, No. 5.
Hikida et al., "Reexpression of RAG-1 and RAG-2 Genes in Activated Mature Mouse B Cells," Science, 1996, pp. 2092-2094, vol. 274, No. 5295.

(56) References Cited

OTHER PUBLICATIONS

Holland et al., "The T-Cell Receptor is not Hardwired to Engage MHC Ligands," Proceedings of the National Academy of Sciences, 2012, pp. E3111-E3118.
Holowka et al., "Fce RI as a Paradigm for a Lipid Raft-Dependent Receptor in Hematopoietic Cells," Immunology, 2001, pp. 99-105, vol. 13.
Hooper, "Determination of Glycosyl-Phosphatidylinositol Membrane Protein Anchorage," Proteomics, 2001, pp. 148-755, vol. 1.
Hopp et al., "A Short Polypeptide Marker Sequence Useful for Recombinant Protein Identification and Purification," Biotechnology, 1988, pp. 1204-1210, vol. 6.
Ignatovich et al., "The Creation of Diversity in the Human Immunoglobulin V Repertoire," Journal of Molecular Biology, 1997, pp. 69-77, vol. 268.
International Search Report and Written Opinion for International Application No. PCT/CA2013/050203 dated Jun. 19, 2013.
International Search Report and Written Opinion for International Application No. PCT/CA2013/050204 dated Jun. 14, 2013.
Jones et al., "Replacing the Complementarity Determining Regions in a Human Antibody with Those from a Mouse," Letters to Nature, 1986, pp. 522-525, vol. 321.
Kaczmarczyk et al., "A Single Vector Containing Modified cre Recombinase and LOX Recombination Sequences for Inducible Tissue-Specific Amplification of Gene Expression," Nucleic Acids Research, 2001, pp. 1-13, vol. 29, No. 12 e56.
Kallenbach et al., "Three Lymphoid-Specific Factors Account for all Junctional Diversity Characteristic of Somatic Assembly of T-cell Receptor and Immunoglobulin Genes," Proceedings of the National Academy of Sciences, 1992, pp. 2799-2803, vol. 89.
Koiwai et al., "Analysis of Human Terminal Deoxynucleotidyl Transferase cDNA Expressible in Mammalian Cells," Biochemical and Biophysical Research Communications, 1987, pp. 185-190, vol. 144, No. 1.
Kondo et al., "Simultaneous on/off Regulation of Transgenes Located on a Mammalian Chromosome with Cre-Expressing Adenovirus and a Mutant loxP," Nucleic Acids Research, 2003, pp. 1-10, vol. 31, No. 14 e76.
Lantelme et al., "An in vitro Model of T Cell Receptor Revision in Mature Human CD8+ T Cells," Molecular Immunology, 2008, pp. 328-337, vol. 45.
Larijani et al., "The Role of Components of Recombination Signal Sequences in Immunoglobulin Gene Segment Usage: a V81x Model," Nucleic Acids Research, 1999, vol. 27, No. 11.
Lee et al., "A Functional Analysis of Spacer of V(D)J Recombination Signal Sequences," PLoS Biology, 2003, pp. 66-69, vol. 1, Issue 1.
Lipovsek et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," Journal of Molecular Biology, 2007, pp. 1024-1041, vol. 368.
Lutz et al., "Independent and Tight Regulation of Transcriptional Units of *Escherichia coli* via the LacR/O, the TetR/O and AraC/11-12 Regulatory Elements," Nucleic Acids Research, 1997, pp. 1203-1210, vol. 25, No. 6.
Maes et al., "Secondary V(D)J Rearrangements and B Cell Receptor-Mediated Down-Regulation of Recombination Activating Gene-2 Expression in a Murine B Cell Line," The Journal of Immunology, 2000, pp. 703-709, vol. 165.
Makrides et al., "Strategies for Achieving High-Level Expression of Genes in *Escherichia coli*," Microbiological Reviews, 1996, pp. 512-538, vol. 60, No. 3.
Mayer, "A New Set of Useful Cloning and Expression Vectors Derived from pBlueScript," Gene, 1995, pp. 41-46, vol. 163.
Miller et al., "Improved Retroviral Vectors for Gene Transfer and Expression," Biotechniques, 1989, pp. 980-990, vol. 7, No. 9.
Miller, "Retrovirus Packaging Cells," Human Gene Therapy, 1990, pp. 5-14, vol. 1.

Minke et al., "TRP Channel Proteins and Signal Transduction," Physiological Review, 2002, pp. 429-472, vol. 82.
Nadel et al., "Sequence of the Spacer in the Recombination Signal Sequence Affects V(D)J Rearrangement Frequency and Correlates with Nonrandom VK Usage in Vitro," Journal of Experimental Medicine, 1998, pp. 1495-1503, vol. 187, No. 9.
Nareoja et al., "Selective Targeting of G-Protein-Coupled Receptor Subtypes with Venom Peptides," Acta Physiologica, 2012, pp. 186-201, vol. 204.
Nicaise et al., "Affinity Transfer by CDR Grafting on a Nonimmunoglobulin Scaffold," Protein Science, 2004, pp. 1882-1891, vol. 13.
Non-Final Office Action issued in U.S. Appl. No. 14/384,772 dated Feb. 1, 2016.
Nord et al., "Binding Proteins Selected from Combinatorial Libraries of a-Helical Bacterial Receptor Domain," Nature Biotechnology, 1997, pp. 772-777, vol. 15.
Nygren et al., "Binding Proteins from Alternative Scaffolds," Journal of Immunological Methods, 2004, pp. 3-28, vol. 290.
Oettinger et al., "RAG-1 and RAG-2, Adjacent Genes That Synergistically Activate V(D)J Recombination," Science, 1990, pp. 1517-1523, vol. 248, No. 4962.
Parker et al., "Antibody Mimics Based on Human Fibronectin Type Three Domain Engineered for Thermostability and High-Affinity Binding to Vascular Endothelial Growth Factor Receptor Two," Protein Engineering, Design & Selection, 2005, pp. 435-444, vol. 18, No. 9.
Partial Supplementary European Search Report for European Application 13761957.3 dated Sep. 1, 2015.
Peterson et al., "Molecular Cloning of Human Terminal Deoxynucleotidyltransferase," Proceedings of the National Academy of Sciences, 1984, pp. 4363-4367, vol. 81.
Phoenix et al., "The Hydrophobic Moment and its Use in the Classification of Amphiphilic Structures (Review)," Molecular Membrane Biology, 2002, pp. 1-10, vol. 19.
Ramsden et al., "Mouse K light-Chain Recombination Signal Sequences Mediate Recombination More Frequently than do those of . Light Chain," Proceedings of the National Academy of Sciences, 1991, pp. 10721-10725, vol. 88.
Rathbun et al., "Comparison of RAG Gene Expression in Normal and Transformed Precursor Lymphocytes," International Immunology, 1993, pp. 997-1000, vol. 5, No. 8.
Restriction Requirement issued in U.S. Appl. No. 14/384,772 dated Oct. 15, 2015.
Riechmann et al., "Reshaping Human Antibodies for Therapy," Nature, 1998, pp. 323-327, vol. 332.
Ritter et al., "Fine-Tuning of GPCR Activity by Receptor-Interacting Proteins," Nature Reviews Molecular Cell Biology, 2009, pp. 819-830, vol. 10, No. 12.
Robinson et al., "Optimizing the Stability of Single-Chain Proteins by Linker Length and Composition Mutagenesis," Proceedings of the National Academy of Sciences, 1998, pp. 5929-5934, vol. 95.
Roch et al., "V(D)J Recombination Frequency is Affected by the Sequence Interposed Between a Pair of Recombination Signals: Sequence Comparison Reveals a Putative Recombinational Enhancer Element," Nucleic Acids Research, 1997, pp. 2303-2310, vol. 25, No. 12.
Rock et al., "CDR3 Length in Antigen-Specific Immune Receptors," Journal of Experimental Medicine, 1994, pp. 323-328, vol. 179.
Rothe et al., "In Vitro Display Technologies Reveal Novel Biopharmaceutics," The FASEB Journal, 2006, pp. 1599-1610, vol. 20.
Runge et al., "Crystal Structure of the Ligand-Bound Glucagon-Like Peptide-1 Receptor Extracellular Domain," The Journal of Biological Chemistry, 2008, pp. 11340-11347, vol. 283, No. 17.
Sadlish et al. "Cytoplasmic Domains of the Reduced Folate Carrier are Essential for Trafficking, but not Function," Biochemical Journal, 2002, pp. 777-786, vol. 364.
Sarmiento et al., "Diverging Mechanisms of Activation of Chemokine Receptors Revealed by Novel Chemokine Agonists," PLoS ONE, 2011, vol. 6, No. 12 e27967.

(56) References Cited

OTHER PUBLICATIONS

Sauer, "Cre/lox: One More Step in the Taming of the Genome," Endocrine, 2002, pp. 221-227, vol. 19, No. 3.

Sauer, "Inducible Gene Targeting in Mice Using the Cre/lox System," Methods: A Companion to Methods in Enzymology, 1998, pp. 381-392, vol. 14.

Schatz et al., "The V(D)J Recombination Activating Gene, RAG-1," Cell, 1989, pp. 1035-1048, vol. 59.

Schlessinger, "Ligand-Induced, Receptor-Mediated Dimerization and Activation of EGF Receptor," Cell, 2002, pp. 669-672, vol. 110.

Simon et al., "Display of Somatostatin-Related Peptides in the Complementarity Determining Regions of an Antibody Light Chain," Archives of Biochemistry and Biophysics, 2005, pp. 148-157, vol. 440.

Sollazzo et al., "Expression of an Exogenous Peptide Epitope Genetically Engineered in the Variable Domain of an Immunoglobulin: Implications for Antibody and Peptide Folding," Protein Engineering, 1990, pp. 215-220, vol. 4, No. 2.

Spiro, "Protein Glycosylation: Nature, Distribution, Enzymatic Formation, and Disease Implications of Glycopeptide Bonds," Glycobiology, 2002, pp. 43R-56R, vol. 12, No. 4.

Stemmer, "Rapid Evolution of a Protein in Vitro by DNA Shuffling," Letters to Nature, 1994, pp. 389-391, vol. 370.

Takada et al., "The Integrins," Genome Biology, 2007, pp. 215.1-215.9, vol. 8, No. 5.

Thai et al., "Distinct and Opposite Diversifying Activities of Human Terminal Deoxynucleotidyltransferase Splice Variants," The Journal of Immunology, 2004, pp. 4009-4019, No. 173.

Thai et al., "Distinct and Opposite Diversifying Activities of Terminal Transferase Splice Variants," Nature Immunology 2002, vol. 3, No. 5.

Thomson et al., "Mutational Analysis of LoxP Sites for Efficient Cre-Mediated Insertion Into Genomic DNA," Genesis, 2003, pp. 162-167, vol. 36.

Tomlinson et al., "The Imprint of Somatic Hypermutation on the Repertoire of Human Germline V Genes," Journal of Molecular Biology, 1996, pp. 813-817, vol. 256.

Underwood et al., "Crystal Structure of Glucagon-Like Peptide-1 in Complex with the Extracellular Domain of the Glucagon-Like Peptide-1 Receptor," Journal of Biological Chemistry, 2010, pp. 7223-730, vol. 285, No. 1.

Van Craenebroeck et al., "Episomal Vectors for Gene Expression in Mammalian Cells," European Journal of Biochemistry, 2000, pp. 5665-5678, vol. 267.

Van Den Beucken et al., "Building Novel Binding Ligands to B7.1 and B7.2 Based on Human Antibody Single Variable Light Chain Domains," Journal of Molecular Biology, 2001, pp. 591-601, vol. 310.

Extended European Search Report issued in European Patent Application 16180577.5 dated Mar. 1, 2017, 11 pages.

Montrose-Refizadeh et al., "High Potency Antagonists of the Pancreatic Glucagon-like Peptide-1 Receptor," The Journal of Biological Chemistry, vol. 272, No. 34, pp. 21201-21206 (1997).

Pigott et al., "The Use of a Novel Discovery Platform to Identify Peptide-Grafted Antibodies that Activate GLP-1 Receptor Signaling," retrieved from the Internet: URL: http://www.innovativetargeting.com/wp-content/uploads/2013/12/Pigott-et-alAntibody-Engineering-2013.pdf, Retrieved on Dec. 8, 2016.

* cited by examiner

A.

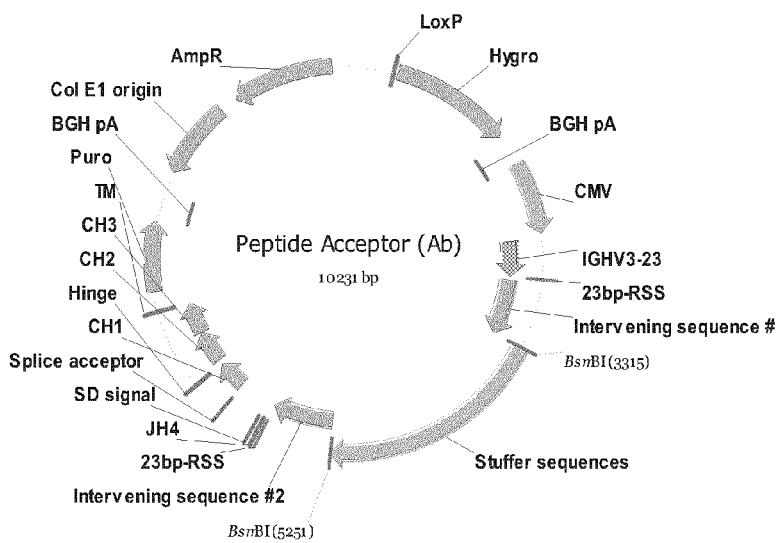

B.

ctaaattgtaagcgttaatattttgttaaaattcgcgttaaattttgttaaatcagctcattttttaaccaataggccgaaatcggcaaaatccc
ttataaatcaaaagaatagaccgagatagggttgagtggccgctacagggcgctcccattcgccattcaggctgcgcaactgttggga
agggcgtttcggtgcgggcctcttcgctattacgccagctggcgaaagggggatgtgctgcaaggcgattaagttgggtaacgccag
ggttttcccagtcacgacgttgtaaaacgacggccagtgagcgcgacgtaatacgactcactatagggcgaattggcggaaggccgt
caaggcctaggcgcgcctgaataacttcgtatagcatacattatagcaatttatcgaaaaagcctgaactcaccgcgacatccgtggag
aaattcctcatcgaaaaattcgactccgtgtccgatctcatgcagctgtccgagggcgaggagagtagagcattctcattcgatgtggg
cgggagaggctacgtgctgagagtgaactcttgtgccgacggcttctacaaggaccgatacgtctaccggcattttgcttccgccgctc
tgcctattccagaagtcctggacattggggagtttagcgagtccctcacttactgtattagccggcgagcccagggagtgacactccag
gatctgcctgaaactgaactgcctgctgtgctccagcctgtcgctgaggcaatggatgctattgctgctgccgatctgagtcagactagc
ggattcggcccatttggaccccagggcattggccagtacacaacatggcgagacttcatctgtgctatcgccgatcctcacgtgtacca
ttggcagactgtgatggacgatactgtgtctgcttctgtggcacaggcactcgacgaactcatgctgtgggctgaggactgtcctgaagt
gagacatctggtccatgccgattttggctccaacaatgtgctcaccgataacgggagaatcactgccgtgatcgactggagcgaggca
atgtttggcgattcccagtacgaagtggccaacatcttcttttggcggccttggctggcttgtatggaacagcagacccggtactttgaac
ggcgccaccctgagctggctgggagtcctagactgagagcctacatgctccgaattggcctggatcagctctaccagtcactggtgga
tggcaatttcgacgatgctgcttgggcacaggggcgctgtgatgctattgtccgatccggcgctggaactgtggggagaacacagatc
gctaggagatccgctgctgtctggaccgatggatgtgtggaagtgctggccgatagtggaaaccggaggccttcaacccgaccccg
ggcaaaggagtaatgaccgtttaaacccgctgatcagcctcgactgtgccttctagttgccagccatctgttgtttgcccctcccccgtgc
cttccttgaccctggaaggtgccactcccactgtcctttcctaataaaatgaggaaattgcatcgcattgtctgagtaggtgtcattctattct
ggggggtggggtggggcaggacagcaaggggaggattgggaagacaatagcaggcatgctggggatgcggtgggctctatgg
ggatcccgcgttgacattgattattgactagttattaatagtaatcaattacggggtcattagttcatagcccatatatggagttccgcgttac
ataacttacggtaaatggcccgcctggctgaccgcccaacgacccccgcccattgacgtcaataatgacgtatgttcccatagtaacgc
caatagggactttccattgacgtcaatgggtggagtatttacggtaaactgcccacttggcagtacatcaagtgtatcatatgccaagtac

Fig. 1 gccccctattgacgtcaatgacggtaaatggcccgcctggcattatgcccagtacatgaccttatgggactttcctacttggcagtacatc
tacgtattagtcatcgctattaccatggtgatgcggttttggcagtacatcaatgggcgtggatagcggtttgactcacggggatttccaa
gtctccaccccattgacgtcaatgggagtttgttttggcaccaaaatcaacgggactttccaaaatgtcgtaacaactccgccccattgac
gcaaatgggcggtaggcgtgtacggtgggaggtctatataagcagagctctctggctaactagagaacccactgcttactgctcgacg
atctgatcaagagacaggataaggagccgccaccatggagtttggctgagctggcttttcttgtggctatttaaaaggtgtccagtgt
gaagtgcagctgctggaaagcggcggaggcctggtgcagcctggcggcagcctgagactgtcttgcgccgccagcggcttcaccctt
cagcagctacgccatgagctgggtccgccaggcccctggcaagggactcgaatgggtgtccgccatcagcggcagcggcggcag
cacctactacgccgacagcgtgaagggccggttcaccatcagccgggacaacagcaagaacaccctgtacctgcagatgaacagc
ctgcgggccgaggacaccgccgtatattactgtgcgaaagacacagtggtagtactccactgtctgggtgtacaaaaacctccctgca
cgcctctctaacctcacaattctgtggcggccgcgccgccaccatgattgaacaagatggattgcacgcaggttctccggccgcttgg
gtggagaggctattcggctatgactgggcacaacagacaatcggctgtctgatgccgccgtgttccggctgtcagcgcaggggcgc
ccggttcttttttgtcaagaccgacctgtccggtgccctgaatgaactgcaggacgaggcagcgcggctatcgtggctggccacgacg
ggcgttccttgcgcagctgtgctcgacgttgtcactgaagcgggaagggactggctgctattgggcgaagtgccggggcaggatctc
ctgtcatctcaccttgctcctgccgagaaagtatccatcatggctgatgcaatgcggcggctgcatacgcttgatccggctacctgccca
ttcgaccaccaagcgaaacatcgcatcgagcgagcacgtactcggatggaagccggtcttgtcgatcaggtgagtacaggaggtgg
agagtacgcgtaacacttaagcgtctctccaagatccttttaacccatcacatatacctgccgttcactattatttagtgaaatgagatatta
tgatattctgaattgtgattaaaaaggcaactttatgcccatgcaacagaaactataaaaaatacagagaatgaaaagaaacagataga
tttttagttctttaggcccgtagtctgcaaatcctttatgattttctatcaaacaaaagaggaaaatagaccagttgcaatccaaacgaga
gtctaatagaatgaggtcgaaaagtaaatcgcgcgggtttgttactgataaagcaggcaagacctaaaatgtgtaaagggcaaagtgta
tactttggcgtcaccccttacatatttaggtctttttttattgtgcgtaactaacttgccatcttcaaacaggagggctggaagaagcagac
cgctaacacagtacataaaaaaggagacatgaacgatgaacatcaaaaagtttgcaaaacaagcaacagtattaacctttactaccgca
ctgctggcaggaggcgcaactcaagcgtttgcgaaagaaacgaaccaaaagccatataaggaaacatacggcatttcccatattaca
cgccatgatatgctgcaaatccctgaacagcaaaaaaatgaaaaatatcaagttcctgagttcgattcgtccacaattaaaaatatctcttc
tgcaaaaggcctggacgtttgggacagctggccattacaaaacgctgacggcactgtcgcaaactatcacggctaccacatcgtctttg
cattagccggagatcctaaaaatgcggatgacacatcgatttacatgttctatcaaaaagtcggcgaaacttctattgacagctggaaaa
acgctggccgcgtctttaaagacagcgacaaattcgatgcaaatgattctatcctaaaagaccaaacacaagaatggtcaggttcagcc
acatttacatctgacggaaaaatccgtttattctacactgatttctccggtaaacattacggcaaacaaacactgacaactgcacaagttaa
cgtatcagcatcagacagctctttgaacatcaacggtgtagaggattataaatcaatctttgacggtgacggaaaaacgtatcaaaatgt
acagcagttcatcgatgaaggcaactacagctcaggcgacaaccatacgctgagagatcctcactacgtagaagataaaggccacaa
atacttagtatttgaagcaaacactggaactgaagatggctaccaaggcgaagaatcttatttaacaaagcatactatggcaaaagcac
atcattcttccgtcaagaaagtcaaaaacttctgcaaagcgataaaaaacgcacggctgagttagcaaacggcgctctcggtatgattg
agctaaacgatgattacacactgaaaaaagtgatgaaaccgctgattgcatctaacacagtaacagatgaaattgaacgcgcgaacgt
cttaaaaatgaacggcaaatggtatctgttcactgactcccgcgcggatcaaaaatgacgattgacggcattacgtctaacgatatttacatg
cttggttatgtttctaattctttaactggcccatacaagccgctgaacaaaactggccttgtgttaaaaatggatcttgatcctaacgatgtaa
cctttacttactcacacttcgctgtacctcaagcgaaaggaaacaatgtcgtgattacaagctatatgacaaacagaggattctacgcag
acaaacaatcaacgtttgcgcctagcttcctgctgaacatcaaaggcaagaaaacatctgttgtcaaagacagcatccttgaacaagga
caattaacagttaacaaataaaaacgcaaaagaaaatgccgattatggtgcactctcagtacaatctgggtaagagacgtccggaggc
cagcccttctcatgttcagagaacatggttaactggtaagtcatgtcgtcccacaggatgatctggacgaagagcatcaggggctcgc
gccagccgaactgttcgccaggctcaaggcgcgcatgcccgacggcgaggatctcgtcgtgacccatggcgatgcctgcttgccga
atatcatggtggaaaatggccgcttttctggattcatcgactgtggccggctgggtgtggcggaccgctatcaggacatagcgttggct
acccgtgatattgctgaagagcttggcggcgaatggctgaccgcttcctcgtgctttacggtatcgccgctcccgattcgcagcgcat
cgccttctatcgccttcttgacgagttcttctgagtcgactgcaggagtcccactgcacccccctcccagtcttctctgtccaggcaccag
gccaggtatctggggtgtgcagccggcctgggtctggcctgaggccacaagcccggggtctgtgtggctgggacagggacgcc
ggctgcctctgctctgtgcttgggccatgtgacccattcgagtgtcctgcacgggcacaggttttgtacacccagacagtggagtacta
ccactgtgactactttgactactggggccagggaaccctggtcaccgtgtcctcaggtaagatggctttccttctgcctccttctctggg
cccagcgtcctctgtcctggagctgggagataatgtccgggggctccttggtctgcgctgggcaaagggtgggcagagtcatgcttgt
gctggggacaaaatgaccttgggacacggggctggctgccacggccggcccgggacagtcggagagtcaggttgctagcgaacct cgcggacagttaagaacccaggggcctctgcgccctgggcccagctctgtcccacaccgcggtcacatggcaccacctctcttgcag
cctccaccaagggcccatcggtcttccccctggcaccctcctccaagagcacctctgggggcacagcggccctgggctgcctggtca
aggactacttccccgaaccggtgacggtgtcgtggaactcaggcgccctgaccagcggcgtgcataccttcccggctgtcctacagt
cctcaggactctactccctcagcagcgtggtgaccgtgccctccagcagcttgggcacccagacctacatctgcaacgtgaatcacaa
gcccagcaacaccaaggtggacaagaaagttgagcccaaatcttgtgacaaaactcacacatgcccaccgtgcccagcacctgaact
cctggggggaccgtcagtcttcctcttcccccaaaacccaaggacaccctcatgatctctagaacccctgaggtcacatgcgtggtg
gtggacgtgagccacgaagaccctgaggtcaagttcaactggtacgtggacggcgtggaggtgcataatgccaagacaaagccgc
gggaggagcagtacaacagcacgtaccgtgtggtcagcgtcctcaccgtcctgcaccaggactggctgaatggcaaggagtacaag
tgcaaggtgtccaacaaagcctccagcccccatcgagaaaaccatctccaaagccaaagggcagccccgagaaccacaggtgt
acaccctgcccccatcccgggatgagctgaccaagaaccaggtcagcctgacctgcctggtcaaaggcttctatcccagcgacatcg
ccgtggagtgggagagcaatgggcagccggagaacaactacaagaccacgcctcccgtgctggactccgacggctccttcttcctct
acagcaagctcaccgtggacaagtctagatggcagcaggggaacgtcttctcatgctccgtgatgcatgaggctctgcacaaccacta
cacgcagaagagcctctccctgtctccgggcaaactggctctcattgtcctgggcggcgtggctggcctgctgctgtttattgggctgg
gcatcttcttttgtgtccggtgtcggcataggaggcgccaaggaggtggcggatctggaggggaggatctggagggggctcagga
tcaggggaggatctggaggcggatcaactgagtacaaacccactgtgaggctcgctactagagatgatgtgcctagagctgtccga
actctggctgctgccttcgccgattaccctgccactcgccataccgtcgatcccgatcgccacattgaacgagtcaccgaactccagga
gctgtttctcactagagtcgggctggatattggcaaagtctgggtggccgatgacggagccgctgtcgctgtgtggactacacctgagt
ctgtggaggctggcgccgtgtttgctgaaattggacctcggatggctgaactgtctggatctcgactggctgcccagcagcagatgga
gggactgctggcaccccatagaccaaaggaacctgcctggtttctggcaactgtgggagtgtcacccgatcatcagggcaaaggact
gggatctgccgtggtgctccctggcgtggaggccgctgaacgagctggcgtccccgcttttctcgaaacttctgcccccgaaatctc
cctttctacgaacgactgggattcactgtcaccgccgatgtcgaagtgcctgaggggcctagaacatggtgtatgacccggaaacccg
gagcttaaccgtttaaacccgctgatcagcctcgactgtgccttctagttgccagccatctgttgtttgcccctcccccgtgccttccttga
ccctggaaggtgccactcccactgtcctttcctaataaaatgaggaaattgcatcgcattgtctgagtaggtgtcattctattctggggggt
ggggtggggcaggacagcaagggggaggattgggaagacaatagcaggcatgctggggatgcggtgggctctatggctcgagtt
aattaactggcctcatgggccttccgctcactgcccgctttccagtcgggaaacctgtcgtgccagctgcattaacatggtcatagctgtt
tccttgcgtattgggcgctctccgcttcctcgctcactgactcgctgcgctcggtcgttcgggtaaagcctggggtgcctaatgagcaaa
aggccagcaaaaggccaggaaccgtaaaaaggccgcgttgctggcgtttttccataggctccgcccccctgacgagcatcacaaaa
atcgacgctcaagtcagaggtggcgaaacccgacaggactataaagataccaggcgtttccccctggaagctccctcgtgcgctctc
ctgttccgaccctgccgcttaccggatacctgtccgcctttctcccttcgggaagcgtggcgctttctcatagctcacgctgtaggtatctc
agttcggtgtaggtcgttcgctccaagctgggctgtgtgcacgaaccccccgttcagcccgaccgctgcgccttatccggtaactatcg
tcttgagtccaacccggtaagacacgacttatcgccactggcagcagccactggtaacaggattagcagagcgaggtatgtaggcgg
tgctacagagttcttgaagtggtggcctaactacggctacactagaagaacagtatttggtatctgcgctctgctgaagccagttaccttc
ggaaaaagagttggtagctcttgatccggcaaacaaaccaccgctggtagcggtggtttttttgtttgcaagcagcagattacgcgcag
aaaaaaaggatctcaagaagatcctttgatcttttctacggggtctgacgctcagtggaacgaaaactcacgttaagggattttggtcatg
agattatcaaaaaggatcttcacctagatccttttaaattaaaaatgaagttttaaatcaatctaaagtatatatgagtaaacttggtctgaca
gttaccaatgcttaatcagtgaggcacctatctcagcgatctgtctatttcgttcatccatagttgcctgactccccgtcgtgtagataacta
cgatacgggagggcttaccatctggccccagtgctgcaatgataccgcgagaaccacgctcaccggctccagatttatcagcaataaa
ccagccagccggaagggccgagcgcagaagtggtcctgcaactttatccgcctccatccagtctattaattgttgccgggaagctaga
gtaagtagttcgccagttaatagtttgcgcaacgttgttgccattgctacaggcatcgtggtgtcacgctcgtcgtttggtatggcttcattc
agctccggttcccaacgatcaaggcgagttacatgatcccccatgttgtgcaaaaaagcggttagctccttcggtcctccgatcgttgtc
agaagtaagttggccgcagtgttatcactcatggttatggcagcactgcataattctcttactgtcatgccatccgtaagatgcttttctgtg
actggtgagtactcaaccaagtcattctgagaatagtgtatgcggcgaccgagttgctcttgcccggcgtcaatacgggataataccgc
gccacatagcagaactttaaaagtgctcatcattggaaaacgttcttcggggcgaaaactctcaaggatcttaccgctgttgagatccag
ttcgatgtaacccactcgtgcacccaactgatcttcagcatcttttactttcaccagcgtttctgggtgagcaaaaacaggaaggcaaaat
gccgcaaaaaagggaataagggcgacacggaaatgttgaatactcatactcttcctttttcaatattattgaagcatttatcagggttattgt
ctcatgagcggatacatatttgaatgtatttagaaaaataaacaaataggggttccgcgcacatttccccgaaaagtgccac (10231
bp)

[SEQ ID NO:28]

Fig. 1 (con.)

```
                                          Fibronectin type III 10
                                               RGD
   -3     Y  H  H  V  E  T  C  V  C  C  H  W  P  V  R  Q  P  R  G  D  K  Q  Q  A  N  F  H
   -2     I  P  S  R  G  D  L  C  M  L  S  L  A  V  E  T  A  P  R  R  Q  A  A  S  Q  F  P
   -1     Y  T  I  T  W  R  P  V  Y  A  V  T  G  R  G  D  S  P  A  E  T  S  S  K  P  I  S
    1  TATACCATCA CGTGGAGACC TGTGTATGCT GTCACTGGCC GTGGAGACAG CCCCGCGGAG ACAAGCAGCA AGCCAATTTC CATT
       ATATGGTAGT GCACCTCTGG ACACATACGA CAGTGACCGG CACCTCTGTC GGGGCGCCTC TGTTCGTCGT TCGGTTAAAG GTAA
```

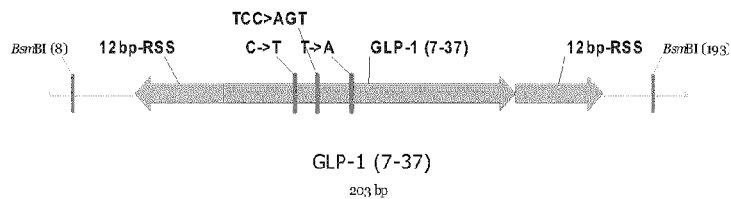

GLP-1 (7-37)
203 bp

B.

cgtctctccaagtgcaaagggacaggaggttttgttaagggctgtatcactgtg**catgccgagggcacctttaccagtgacgtgagt
agctacctagaaggccaggccgccaaagagtttatcgcctggctcgtgaagggcagaggc**cacagtgatacagcccttaacaa
aaaccctactgcaacctggcggtaagagacg
[SEQ ID NO:36]

C.

HAEGTFTSDVSSYLEGQAAKEFIAWLVKGRG    [SEQ ID NO:38]

D.

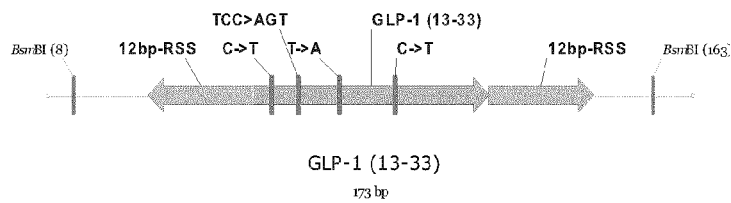

GLP-1 (13-33)
173 bp

E.

cgtctctccaagtgcaaagggacaggaggttttgttaagggctgtatcactgtg**accagtgacgtgagtagctacctagaaggcca
ggccgctaaagagtttatcgcctggctcgtg**cacagtgatacagcccttaacaaaaaccctactgcaacctggcggtaagagacg
[SEQ ID NO:37]

F.

TSDVSSYLEGQAAKEFIAWLV    [SEQ ID NO:39]

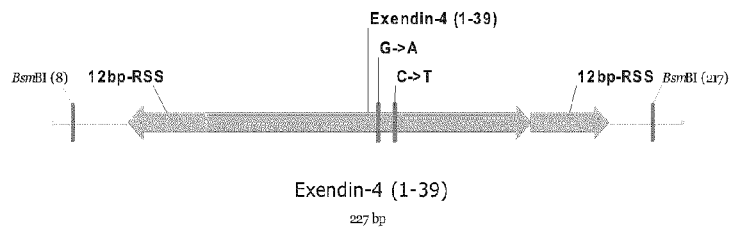

Exendin-4 (1-39)
227 bp

B.

cgtctctccaagtgcaaagggacaggaggttttgttaagggctgtatcactgtg**catggcgagggcaccttcaccagcgacctgag
caagcagatggaagaggaagccgtgcggctattcattgagtggctgaagaatggcggccctagctctggcgcccctcctcctt**
ctcacagtgatacagcccttaacaaaaaccctactgcaacctggcggtaagagacg
[SEQ ID NO:40]

C.

HGEGTFTSDLSKQMEEEAVRLFIEWLKNGGPSSGAPPPS   [SEQ ID NO:43]

D.

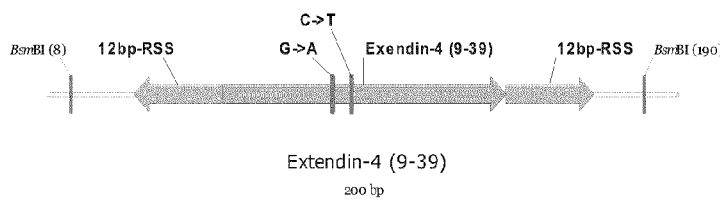

Extendin-4 (9-39)
200 bp

E.

cgtctctccaagtgcaaagggacaggaggttttgttaagggctgtatcactgtg**ctgagcaagcagatggaagaggaagccgtgc
ggctattcattgagtggctgaagaatggcggccctagctctggcgcccctcctccttct**cacagtgatacagcccttaacaaaaac
ccctactgcaacctggcggtaagagacg
[SEQ ID NO:41]

F.

LSKQMEEEAVRLFIEWLKNGGPSSGAPPPS   [SEQ ID NO:44]

Fig. 4

G.
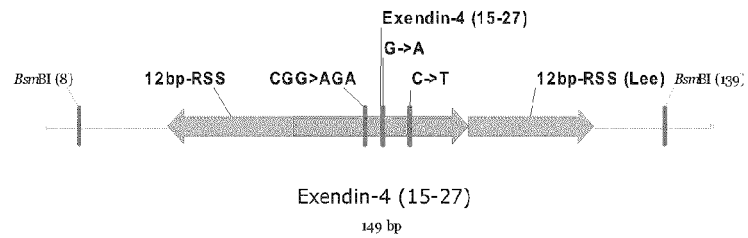
Exendin-4 (15-27)
149 bp
H.
cgtctctccaagtgcaaagggacaggaggtttttgttaagggctgtatcactgtg**gaagaggaagccgtgagactattcattgagtg
gctgaag**cacagtgatacagcccttaacaaaaaccccctactgcaacctggcggtaagagacg
[SEQ ID NO:42]
I.
EEEAVRLFIEWLK    [SEQ ID NO:45]
Fig. 4 (con.)

A.

```
                                        IL-8
   A    K    E    L    R    C    Q    C    I    K    T    Y    S    K    P    F    H    P    K    F    I    K    E    L    R
TGCTA AAGAACTTAG ATGTCAGTGC ATAAAGACAT ACTCCAAACC TTTCCACCCC AAATTTATCA AAGAACTGAG A
ACGAT TTCTTGAATC TACAGTCACG TATTTCTGTA TGAGGTTTGG AAAGGTGGGG TTTAAATAGT TTCTTGACTC T
```

B.

AAAGAACTTAGATGTCAGTGCATAAAGACATACTCTAAACCTTTCCACCCTAAAT
TTATCAAA
[SEQ ID NO:12]

C.

```
                                                         CXCL1
                                    Binding domain                                      Stop (TGA)
           Stop (TGA)                                                                 Stop (TGA)
      A    T    E    L    R    C    Q    C    L    Q    T    L    Q    G    I    H    P    K    N    I    Q    S    V
CGTGGC CACTGAACTGCGCTGC CAGTGCTTGCAGACCC TGCAGGGAATTCACCC CAAGAACATCCAAAGT GTGAACGTGAAGTCCC
GCACCG GTGACTTGACGCGACG GTCACGAACGTCTGGG ACGTCCCTTAAGTGGG GTTCTTGTAGGTTTCA CACTTGCACTTCAGGG
                                                  Stop (TGA)
```

D.

GCCACTGAACTGCGCTGCCAGTGCTTGCAGACCCTGCAGGGAATTCACCCCAAG
AACATCCAAAGTGTG
[SEQ ID NO:49]

E.

```
                   Stop (TGA)
        Stop (TAG)                          Stop (TAA)
     A    R    *    F    L    P    E    I    *
     C    *    V    I    S    S    G    N    L
     L    L    G    D    F    F    R    K    S    K
  TGCCCTGCT GGTGATTTCT TCCGGAAATC TAAAGAGAAG
  ACGGGACGA CCACTAAAGA AGGCCTTTAG ATTTCTCTTC
       Stop (TAG)                      Stop (TAG)
```

Fig. 5

```
ErbB1    C P P L M L Y N P T T Y Q M D V N P E G K Y S F G A T C V  268
ErbB2    C P A L V T Y N T D T F E S M P N P E G R Y T F G A S C V  275
ErbB3    C P Q P L V Y N K L T F Q L E P N P H T K Y Q Y G G V C V  268
ErbB4    C P Q T F V Y N P T T F Q L E M N F N A K Y T Y G A F C V  265
```

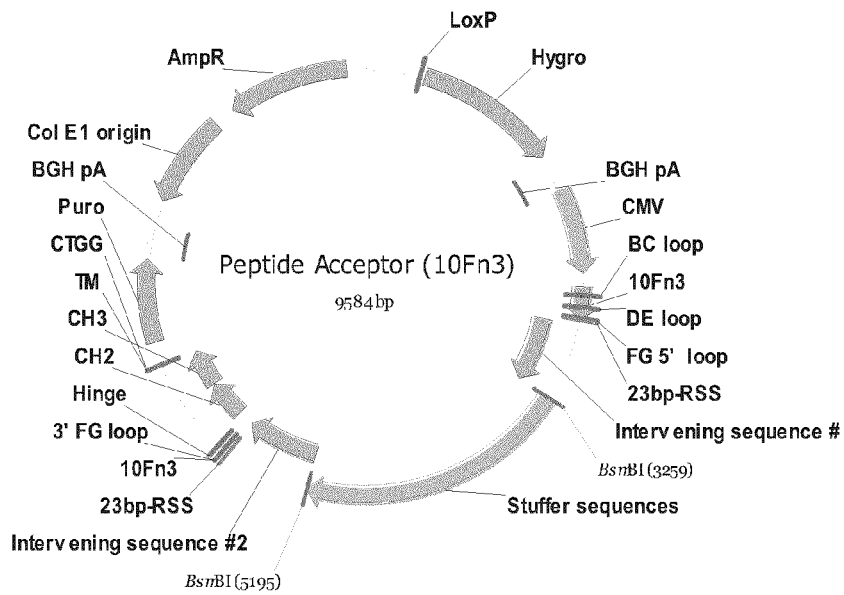

B.

ctaaattgtaagcgttaatattttgttaaaattcgcgttaaattttgttaaatcagctcatttttaaccaataggccgaaatcggcaaaatccc
ttataaatcaaaagaatagaccgagatagggttgagtggccgctacagggcgctcccattcgccattcaggctgcgcaactgttgggga
agggcgtttcggtgcgggcctcttcgctattacgccagctggcgaaaggggggatgtgctgcaaggcgattaagttgggtaacgccag
ggttttcccagtcacgacgttgtaaaacgacggccagtgagcgcgacgtaatacgactcactatagggcgaattggcggaaggccgt
caaggcctaggcgcgcctgaataacttcgtatagcatacattatagcaatttatcgaaaaagcctgaactcaccgcgacatccgtggag
aaattcctcatcgaaaaattcgactccgtgtccgatctcatgcagctgtccgagggcgaggagagtagagcattctcattcgatgtggg
cgggagaggctacgtgctgagagtgaactcttgtgccgacggcttctacaaggaccgatacgtctaccggcatttttgcttccgccgctc
tgcctattccagaagtcctggacattggggagtttagcgagtccctcacttactgtattagccggcgagcccagggagtgacactccag
gatctgcctgaaactgaactgcctgctgtgctccagcctgtcgctgaggcaatggatgctattgctgctgccgatctgagtcagactagc
ggattcggcccatttggaccccagggcattggccagtacacaacatggcgagacttcatctgtgctatcgccgatcctcacgtgtacca
ttggcagactgtgatggacgatactgtgtctgcttctgtggcacaggcactcgacgaactcatgctgtgggctgaggactgtcctgaagt
gagacatctggtccatgccgattttggctccaacaatgtgctcaccgataacgggagaatcactgccgtgatcgactggagcgaggca
atgtttggcgattcccagtacgaagtggccaacatcttctttttggcggccttggctggcttgtatggaacagcagacccggtactttgaac
ggcgccaccctgagctggctgggagtcctagactgagagcctacatgctccgaattggcctggatcagctctaccagtcactggtgga
tggcaatttcgacgatgctgcttgggcacaggggcgctgtgatgctattgtccgatccggcgctggaactgtggggagaacacagatc
gctaggagatccgctgctgtctggaccgatggatgtgtggaagtgctggccgatagtggaaaccggaggccttcaacccgaccccg
ggcaaaggagtaatgaccgttttaaacccgctgatcagcctcgactgtgccttctagttgccagccatctgttgtttgcccctcccccgtgc
cttccttgaccctggaaggtgccactcccactgtccttttcctaataaaatgaggaaattgcatcgcattgtctgagtaggtgtcattctattct
gggggggtggggtggggcaggacagcaaggggggaggattgggaagacaatagcaggcatgctggggatgcggtgggctctatgg
ggatcccgcgttgacattgattattgactagttattaatagtaatcaattacggggtcattagttcatagcccatatatggagttccgcgttac
ataacttacggtaaatggcccgcctggctgaccgcccaacgaccccgcccattgacgtcaataatgacgtatgttcccatagtaacgc

FIG. 7 caatagggactttccattgacgtcaatgggtggagtatttacggtaaactgcccacttggcagtacatcaagtgtatcatatgccaagtac
gcccccattgacgtcaatgacggtaaatggcccgcctggcattatgcccagtacatgaccttatgggactttcctacttggcagtacatc
tacgtattagtcatcgctattaccatggtgatgcggttttggcagtacatcaatgggcgtggatagcggtttgactcacggggatttccaa
gtctccacccattgacgtcaatgggagtttgttttggcaccaaaatcaacgggactttccaaaatgtcgtaacaactccgccccattgac
gcaaatgggcggtaggcgtgtacggtggaggtctatataagcagagctctctggctaactagagaacccactgcttactgctcgacg
atctgatcaagagacaggataaggagccgccaccatggagtttgggctgagctggcttttcttgtggctatttaaaaggtgtccagtgt
tccgatgtgcccagggacctggaagtggtggccgccacacctaccagcctgctgatctcttgggatgcccctgccgtgaccgtgcgg
tactacagaatcacctacggcgagacaggcggcaacagccccgtgcaggagtttacagtgcccggcagcaagagcaccgccacca
tctctggactgaagcccggcgtggactacaccatcaccgtgtacgccgtgacaggcagaggcgatagccacagtggtagtactccac
tgtctgggtgtacaaaaacctccctgcacgcctctctaacctcacaattctgtggcggccgcgccgccaccatgattgaacaagatgga
ttgcacgcaggttctccggccgcttgggtggagaggctattcggctatgactgggcacaacagacaatcggctgtctgatgccgccg
tgttccggctgtcagcgcaggggcgcccggttcttttttgtcaagaccgacctgtccggtgccctgaatgaactgcaggacgaggcagc
gcggctatcgtggctggccacgacgggcgttccttgcgcagctgtgctcgacgttgtcactgaagcgggaagggactggctgctattg
ggcgaagtgccggggcaggatctcctgtcatctcaccttgctcctgccgagaaagtatccatcatggctgatgcaatgcggcggctgc
atacgcttgatccggctacctgcccattcgaccaccaagcgaaacatcgcatcgagcgagcacgtactcggatggaagccggtcttgt
cgatcaggtgagtacaggaggtggagagtacgcgtaacacttaagcgtctctccaagatccttttaacccatcacatatacctgccgtt
cactattatttagtgaaatgagatatttatgatattttctgaattgtgattaaaaaggcaactttatgcccatgcaacagaaactataaaaaata
cagagaatgaaaagaaacagatagatttttagttctttaggcccgtagtctgcaaatcctttatgattttctatcaaacaaaagaggaaaa
tagaccagttgcaatccaaacgagagtctaatagaatgaggtcgaaaagtaaatcgcgcgggtttgttactgataaagcaggcaagac
ctaaaatgtgtaaagggcaaagtgtatactttggcgtcacccccttacatatttaggtcttttttttattgtgcgtaactaacttgccatcttcaaa
caggagggctggaagaagcagaccgctaacacagtacataaaaaaggagacatgaacgatgaacatcaaaaagtttgcaaaacaa
gcaacagtattaacctttactaccgcactgctggcaggaggcgcaactcaagcgtttgcgaaagaaacgaaccaaaagccatataag
gaaacatacggcatttcccatattacacgccatgatatgctgcaaatccctgaacagcaaaaaaatgaaaaatatcaagttcctgagttc
gattcgtccacaattaaaaatatctcttctgcaaaaggcctggacgtttgggacagctggccattacaaaacgctgacggcactgtcgca
aactatcacggctaccacatcgtctttgcattagccggagatcctaaaaatgcggatgacacatcgatttacatgttctatcaaaaagtcg
gcgaaacttctattgacagctggaaaaacgctggccgcgtctttaaagacagcgacaaattcgatgcaaatgattctatcctaaaagac
caaacacaagaatggtcaggttcagccacatttacatctgacggaaaaatccgtttattctacactgatttctccggtaaacattacggca
aacaaacactgacaactgcacaagttaacgtatcagcatcagacagctctttgaacatcaacggtgtagaggattataaatcaatcttga
cggtgacggaaaaacgtatcaaaatgtacagcagttcatcgatgaaggcaactacagctcaggcgacaaccatacgctgagagatcc
tcactacgtagaagataaaggccacaaatacttagtatttgaagcaaacactggaactgaagatggctaccaaggcgaagaatctttatt
taacaaagcatactatggcaaaagcacatcattcttccgtcaagaaagtcaaaaaactctgcaaagcgataaaaaacgcacggctgagt
tagcaaacggcgctctcggtatgattgagctaaacgatgattacacactgaaaaaagtgatgaaaccgctgattgcatctaacacagta
acagatgaaattgaacgcgcgaacgtctttaaaatgaacggcaaatggtatctgttcactgactcccgcggatcaaaaatgacgattga
cggcattacgtctaacgatatttacatgcttggttatgtttctaattctttaactggcccatacaagccgctgaacaaaactggccttgtgtta
aaaatggatcttgatcctaacgatgtaacctttacttactcacacttcgctgtacctcaagcgaaaggaaacaatgtcgtgattacaagcta
tatgacaaacagaggattctacgcagacaaacaatcaacgtttgcgcctagcttcctgctgaacatcaaaggcaagaaaacatctgttgt
caaagacagcatccttgaacaaggacaattaacagttaacaaataaaaacgcaaaagaaaatgccgattatggtgcactctcagtaca
atctgggtaagagacgtccggaggccagcccttctcatgttcagagaacatggttaactggttaagtcatgtcgtcccacaggatgatct
ggacgaagagcatcaggggctcgcgccagccgaactgttcgccaggctcaaggcgcgcatgcccgacggcgaggatctcgtcgt
gacccatggcgatgcctgcttgccgaatatcatggtggaaaatggccgcttttctggattcatcgactgtggccggctgggtgtggcgg
accgctatcaggacatagcgttggctacccgtgatattgctgaagagcttggcggcgaatgggctgaccgcttcctcgtgctttacggt
atcgccgctcccgattcgcagcgcatcgccttctatcgccttcttgacgagttcttctgagtcgactgcaggagtcccactgcaccccc
tcccagtcttctctgtccaggcaccaggccaggtatctggggtgtgcagccggcctgggtctggcctgaggccacaagcccggggt
ctgtgtggctggggacagggacgccggctgcctctgctctgtgcttgggcatgtgacccattcgagtgtcctgcacgggcacaggtt
tttgtacacccagacagtggagtactaccactgtgcctgccagcagcaagcccatcagcatcaactaccggaccggtaccgagccca
aatcttgtgacaaaactcacacatgcccaccgtgcccagcacctgaactcctgggggaccgtcagtcttcctcttccccccaaaaccc
aaggacaccctcatgatctctagaacccctgaggtcacatgcgtggtggtggacgtgagccacgaagaccctgaggtcaagttcaact ggtacgtggacggcgtggaggtgcataatgccaagacaaagccgcgggaggagcagtacaacagcacgtaccgtgtggtcagcgt
cctcaccgtcctgcaccaggactggctgaatggcaaggagtacaagtgcaaggtgtccaacaaagccctcccagcccccatcgaga
aaaccatctccaaagccaaagggcagccccgagaaccacaggtgtacaccctgcccccatcccgggatgagctgaccaagaacca
ggtcagcctgacctgcctggtcaaaggcttctatcccagcgacatcgccgtggagtgggagagcaatgggcagccggagaacaact
acaagaccacgcctcccgtgctggactccgacggctccttcttcctctacagcaagctcaccgtggacaagtctagatggcagcagg
ggaacgtcttctcatgctccgtgatgcatgaggctctgcacaaccactacacgcagaagagcctctccctgtctccgggcaaactggct
ctcattgtcctgggcggcgtggctggcctgctgctgtttattgggctgggcatcttcttttgtgtccggtgtcggcataggaggcgccaag
gaggtggcggatctggagggggaggatctggaggggggctcaggatcaggggggaggatctggaggcggatcaactgagtacaaac
ccactgtgaggctcgctactagagatgatgtgcctagagctgtccgaactctggctgctgccttcgccgattaccctgccactcgccata
ccgtcgatcccgatcgccacattgaacgagtcaccgaactccaggagctgtttctcactagagtcgggctggatattggcaaagtctgg
gtggccgatgacggagccgctgtcgctgtgtggactacacctgagtctgtggaggctggcgccgtgtttgctgaaattggacctcgga
tggctgaactgtctggatctcgactggctgcccagcagcagatggagggactgctggcaccccatagaccaaaggaacctgcctggt
ttctggcaactgtgggagtgtcacccgatcatcagggcaaaggactgggatctgccgtggtgctccctggcgtggaggccgctgaac
gagctggcgtccccgcttttctcgaaacttctgccccccgaaatctcccttctacgaacgactgggattcactgtcaccgccgatgtcg
aagtgcctgaggggcctagaacatggtgtatgacccggaaacccggagcttaaccgtttaaaccccgctgatcagcctcgactgtgcct
tctagttgccagccatctgttgtttgccccctcccccgtgccttccttgaccctggaaggtgccactcccactgtcctttcctaataaaatgag
gaaattgcatcgcattgtctgagtaggtgtcattctattctgggggggtggggtggggcaggacagcaaggggggaggattgggaagac
aatagcaggcatgctggggatgcggtgggctctatggctcgagttaattaactggcctcatgggccttccgctcactgcccgctttcca
gtcgggaaacctgtcgtgccagctgcattaacatggtcatagctgtttccttgcgtattgggcgctctccgcttcctcgctcactgactcg
ctgcgctcggtcgttcgggtaaagcctggggtgcctaatgagcaaaaggccagcaaaaggccaggaaccgtaaaaaggccgcgtt
gctggcgtttttccataggctccgcccccctgacgagcatcacaaaaatcgacgctcaagtcagaggtggcgaaacccgacaggact
ataaagataccaggcgtttccccctggaagctccctcgtgcgctctcctgttccgaccctgccgcttaccggatacctgtccgcctttctc
ccttcgggaagcgtggcgctttctcatagctcacgctgtaggtatctcagttcggtgtaggtcgttcgctccaagctgggctgtgtgcac
gaaccccccgttcagcccgaccgctgcgccttatccggtaactatcgtcttgagtccaacccggtaagacacgacttatcgccactggc
agcagccactggtaacaggattagcagagcgaggtatgtaggcggtgctacagagttcttgaagtggtggcctaactacggctacact
agaagaacagtatttggtatctgcgctctgctgaagccagttaccttcggaaaaagagttggtagctcttgatccggcaaacaaaccac
cgctggtagcggtggtttttttgtttgcaagcagcagattacgcgcagaaaaaaaggatctcaagaagatcctttgatcttttctacgggggt
ctgacgctcagtggaacgaaaactcacgttaagggattttggtcatgagattatcaaaaaggatcttcacctagatcctttaaattaaaaa
tgaagttttaaatcaatctaaagtatatatgagtaaacttggtctgacagttaccaatgcttaatcagtgaggcacctatctcagcgatctgt
ctatttcgttcatccatagttgcctgactccccgtcgtgtagataactacgatacgggagggcttaccatctggccccagtgctgcaatga
taccgcgagaaccacgctcaccggctccagatttatcagcaataaaccagccagccggaagggccgagcgcagaagtggtcctgc
aactttatccgcctccatccagtctattaattgttgccgggaagctagagtaagtagttcgccagttaatagtttgcgcaacgttgttgccat
tgctacaggcatcgtggtgtcacgctcgtcgtttggtatggcttcattcagctccggttcccaacgatcaaggcgagttacatgatcccc
atgttgtgcaaaaaagcggttagctccttcggtcctccgatcgttgtcagaagtaagttggccgcagtgttatcactcatggttatggcag
cactgcataattctcttactgtcatgccatccgtaagatgcttttctgtgactggtgagtactcaaccaagtcattctgagaatagtgtatgc
ggcgaccgagttgctcttgcccggcgtcaatacggataataccgcgccacatagcagaactttaaaagtgctcatcattggaaaacgt
tcttcggggcgaaaactctcaaggatcttaccgctgttgagatccagttcgatgtaacccactcgtgcacccaactgatcttcagcatcttt
tactttcaccagcgtttctgggtgagcaaaaacaggaaggcaaatgccgcaaaaaagggaataagggcgacacggaaatgttgaat
actcatactcttcctttttcaatattattgaagcatttatcagggttattgtctcatgagcggatacatatttgaatgtatttagaaaaataaaca
aataggggttccgcgcacatttccccgaaaagtgccac (9584 bp)

[SEQ ID NO:63]

FIG. 7 (con.)

A.

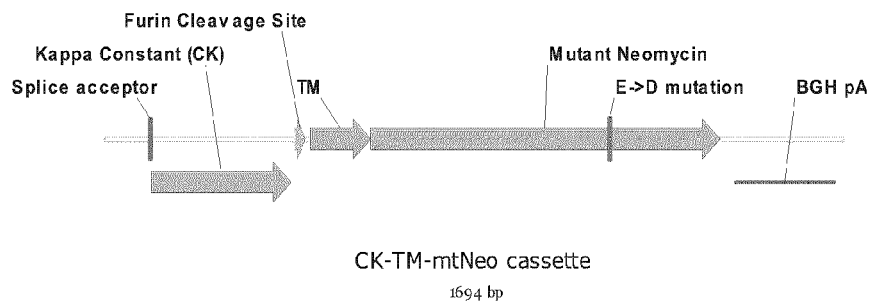

CK-TM-mtNeo cassette
1694 bp

B.

aattcttctgtctgtccctaacatgccctgtgattatccgcaaacaacacacccaagggcagaactttgttacttaaacaccatcctgtttgc
ttctttcctcaggaactgtggctgcaccatctgtcttcatcttcccgccatctgatgagcagttgaaaagcggaacagccagcgttgtgtg
cctgctgaataacttctatcccagagaggccaaagtacagtggaaggtggataacgccctccaatcgggtaactcccaggagagtgtc
acagagcaggacagcaaggacagcacctacagcctcagcagcaccctgacgctgagcaaagcagactacgagaaacacaaagtc
tacgcctgcgaagtcacccatcagggcctgagcagccccgtcacaaagagcttcaacaggggagagtgtggcggcggc**agctccc
ggcaccgccgagccctg**ggcggcggcagcgacgtcccgtcaaatattgcaaaaattatcatcggcccccctcatctttgtctttctcttct
ccgttgtgattggaagtatttatctattcctgagaaagaggcagccagatgggccgctgggaccgctttacgcttctggaagcgctattg
aacaagatggattgcacgcaggttctccggccgcttgggtggagaggctattcggctatgactgggcacaacagacaatcggctgct
ctgatgccgccgtgttccggctgtcagcgcaggggcgcccggttcttttttgtcaagaccgacctgtccggtgccctgaatgaactgcag
gacgaggcagcgcggctatcgtggctggccacgacgggcgttccttgcgcagctgtgctcgacgttgtcactgaagcgggaaggga
ctggctgctattgggcgaagtgccggggcaggatctcctgtcatctcaccttgctcctgccgagaaagtatccatcatggctgatgcaat
gcggcggctgcatacgcttgatccggctacctgcccattcgaccaccaagcgaaacatcgcatcgagcgagcacgtactcggatgg
aagccggtcttgtcgatcaggatgatctggacgaagagcatcaggggctcgcgccagccgaactgttcgccaggctcaaggcgcgc
atgcccgacggcgatgatctcgtcgtgacccatggcgatgcctgcttgccgaatatcatggtggaaaatggccgcttttctggattcatc
gactgtggccggctgggtgtggcggaccgctatcaggacatagcgttggctacccgtgatattgctgaagagcttggcggcgaatgg
gctgaccgcttcctcgtgctttacggtatcgccgctcccgattcgcagcgcatcgccttctatcgccttcttgacgagttcttctgatctaga
gggcccgtttaaacccgctgatcagcctcgactgtgccttctagttgccagccatctgttgtttgcccctcccccgtgccttccttgaccct
ggaaggtgccactcccactgtcctttcctaataaaatgaggaaattgcatcgcattgtctgagtaggtgtcattctattctggggggtggg
gtggggcaggacagcaagggggaggattgggaagacaatagcaggcatgctggggatgcggtgggctctatggcttctgaggcg
gctgcagttatg

[SEQ ID NO:64]

FIG. 9

A.
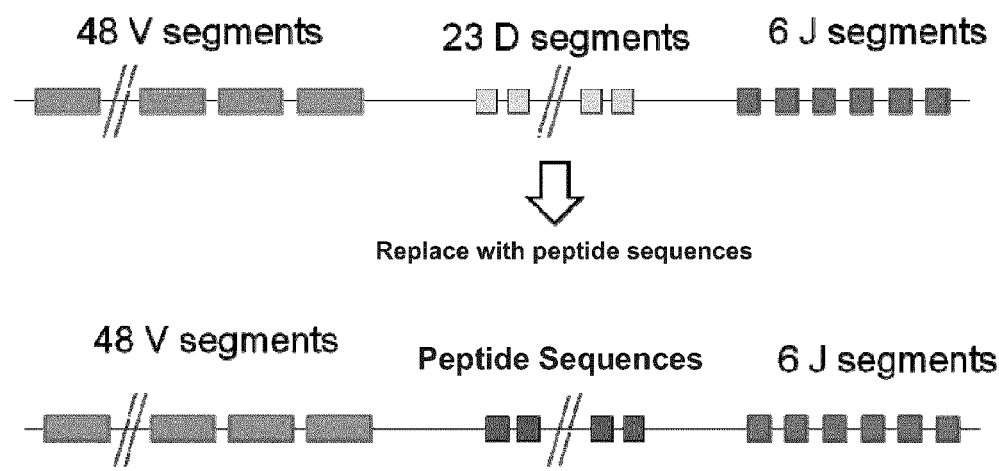
B.
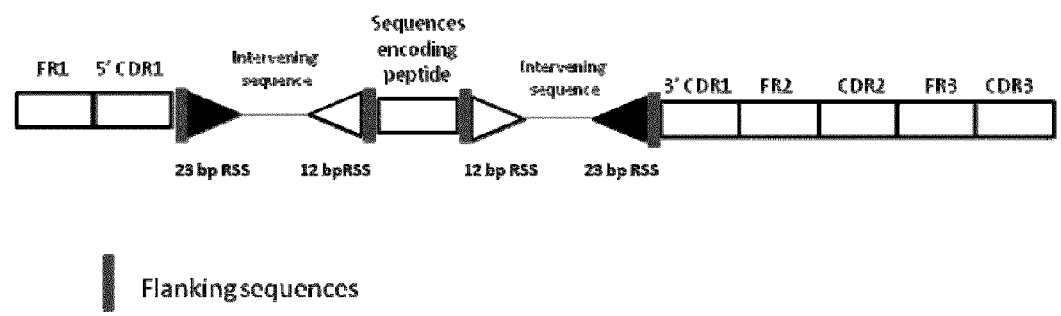
FIG. 10

A.

| 9 mer | 5' 12 bp RSS 12 bp spacer | 7 mer | 5' Flank | Peptide | 3' Flank | 7 mer | 3' 12bp RSS 12 bp spacer | 9 mer |
|---|---|---|---|---|---|---|---|---|
| GGTTTTTGT | TAAGGGCTGTAT | CACTGTG | NNKNNNKNNKNNK | anti TpoR | NNKNNKNNKNNK | CACAGTG | CTCCAGGGCTGA | ACAAAAACC |

B.

| 9 mer | 5' 12 bp RSS 12 bp spacer | 7 mer | 5' Flank | Peptide | 3' Flank | 7 mer | 3' 12bp RSS 12 bp spacer | 9 mer |
|---|---|---|---|---|---|---|---|---|
| GGTTTTTGT | TAAGGGCTGTAT | CACTGTG | NNKNNK | | NNKNNK | CACAGTG | CTCCAGGGCTGA | ACAAAAACC |

| Peptide |
|---|
| GLP1 7-37 |
| GLP1 13-33 |
| Exendin4 1-39 |
| Exendin4 9-39 |
| Exendin4 15-27 |

C.

| | Peptide |
|---|---|
| Anti TPOR | ATCGAGGGCCCTACCCTGAGACAGTGGCTGGCCGCTAGAGCT |
| GLP1 7-37 | CATGCCGAGGGCCACCTTTACCTCCGACGTGTCCTCATATCTGGAAGGCCAAGCCGCCAAAGAGTTTATCGCCTGGCTAGTAAAA |
| GLP1 13-33 | ACCTCCGACGTGTCCTCATATCTGGAAGGCCACGCCGCCAAACAATGGAAGAAGCCGTCCGGCTGTTCATCGAATGCTA |
| Exendin4 1-39 | CATGGCGAGGGCACCTTCACCTCCGACCTGTCCAAACAATGGAAGAAGAACCGTCCGGCTGTTCATCGAATGCTG |
| Exendin4 9-39 | GACCTGTCCAAACAATGGAAGAAGAACCGTCCGGCTGTTCATCGAATGGCTGAAAATGGCGGGCCCTTCCTGG |
| Exendin4 15-27 | GAAGAAGAAGCCGTCCGGCTGTTCATCGAATGGCTGAAA |

FIG. 11

A.
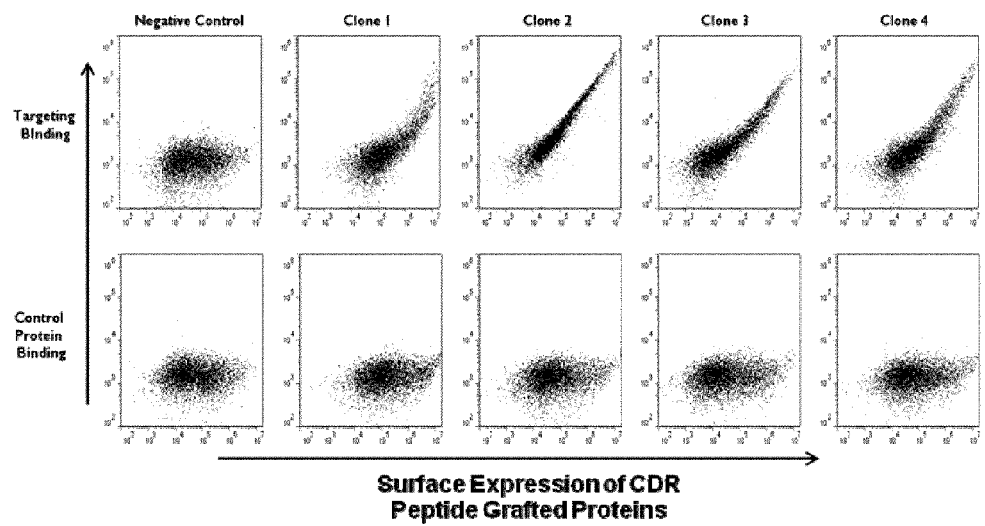
B.
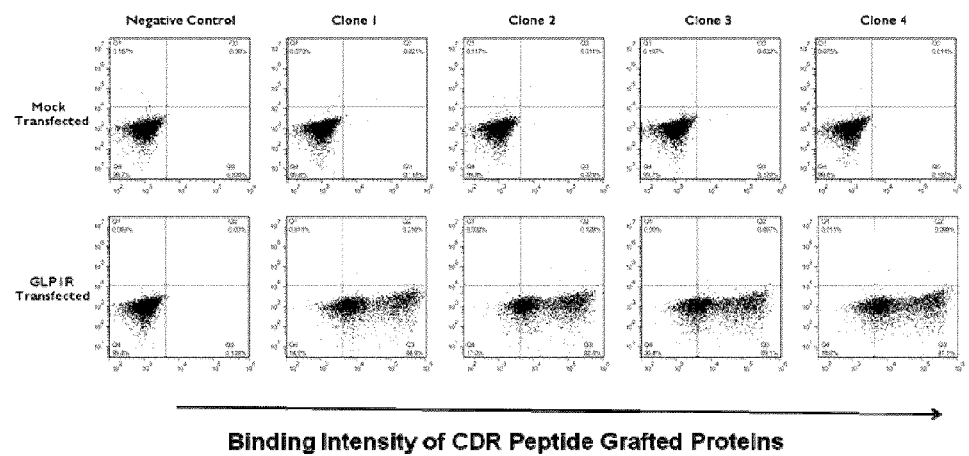
FIG. 12

SEQUENCE LISTING

<160> NUMBER OF SEQ ID NOS: 94

<210> SEQ ID NO 1
<211> LENGTH: 12

```
<212> TYPE: DNA
<213> ORGANISM: Artificial Sequence
<220> FEATURE:
<223> OTHER INFORMATION: RSS spacer sequence

<400> SEQUENCE: 1
atacagacct ta                                                          12

<210> SEQ ID NO 2
<211> LENGTH: 12
<212> TYPE: DNA
<213> ORGANISM: Artificial Sequence
<220> FEATURE:
<223> OTHER INFORMATION: RSS spacer sequence

<400> SEQUENCE: 2
ctacagactg ga                                                          12

<210> SEQ ID NO 3
<211> LENGTH: 12
<212> TYPE: DNA
<213> ORGANISM: Artificial Sequence
<220> FEATURE:
<223> OTHER INFORMATION: RSS spacer sequence

<400> SEQUENCE: 3
ctccagggct ga                                                          12

<210> SEQ ID NO 4
<211> LENGTH: 12
<212> TYPE: DNA
<213> ORGANISM: Artificial Sequence
<220> FEATURE:
<223> OTHER INFORMATION: RSS spacer sequence

<400> SEQUENCE: 4
gtacagacca at                                                          12

<210> SEQ ID NO 5
<211> LENGTH: 23
<212> TYPE: DNA
<213> ORGANISM: Artificial Sequence
<220> FEATURE:
<223> OTHER INFORMATION: RSS spacer sequence

<400> SEQUENCE: 5
gtagtactcc actgtctggc tgt                                              23

<210> SEQ ID NO 6
<211> LENGTH: 23
<212> TYPE: DNA
<213> ORGANISM: Artificial Sequence
<220> FEATURE:
<223> OTHER INFORMATION: RSS spacer sequence

<400> SEQUENCE: 6
ttgcaaccac atcctgagtg tgt                                              23

<210> SEQ ID NO 7
<211> LENGTH: 23
<212> TYPE: DNA
<213> ORGANISM: Artificial Sequence
<220> FEATURE:
<223> OTHER INFORMATION: RSS spacer sequence

<400> SEQUENCE: 7
```
acggagataa aggaggaagc agg                                                    23

<210> SEQ ID NO 8
<211> LENGTH: 23
<212> TYPE: DNA
<213> ORGANISM: Artificial Sequence
<220> FEATURE:
<223> OTHER INFORMATION: RSS spacer sequence

<400> SEQUENCE: 8
gccgggcccc gcggcccggc ggc                                                    23

<210> SEQ ID NO 9
<211> LENGTH: 27
<212> TYPE: PRT
<213> ORGANISM: Artificial Sequence
<220> FEATURE:
<223> OTHER INFORMATION: Modified fibronectin sequence

<400> SEQUENCE: 9

Tyr His His Val Glu Thr Cys Val Cys Cys His Trp Pro Trp Arg Gln
1               5                   10                  15

Pro Arg Gly Asp Lys Gln Gln Ala Asn Phe His
            20                  25

<210> SEQ ID NO 10
<211> LENGTH: 27
<212> TYPE: PRT
<213> ORGANISM: Artificial Sequence
<220> FEATURE:
<223> OTHER INFORMATION: Modified fibronectin sequence

<400> SEQUENCE: 10

Ile Pro Ser Arg Gly Asp Leu Cys Met Leu Ser Leu Ala Val Glu Thr
1               5                   10                  15

Ala Pro Arg Arg Gln Ala Ala Ser Gln Phe Pro
            20                  25

<210> SEQ ID NO 11
<211> LENGTH: 28
<212> TYPE: PRT
<213> ORGANISM: Artificial Sequence
<220> FEATURE:
<223> OTHER INFORMATION: Modified fibronectin sequence

<400> SEQUENCE: 11

Tyr Thr Ile Thr Trp Arg Pro Val Tyr Ala Val Thr Gly Arg Gly Asp
1               5                   10                  15

Ser Pro Ala Glu Thr Ser Ser Lys Pro Ile Ser Ile
            20                  25

<210> SEQ ID NO 12
<211> LENGTH: 63
<212> TYPE: DNA
<213> ORGANISM: Artificial Sequence
<220> FEATURE:
<223> OTHER INFORMATION: IL-8 nucleotide sequence for peptide grafting

<400> SEQUENCE: 12
aaagaactta gatgtcagtg cataaagaca tactctaaac ctttccaccc taaatttatc          60
aaa                                                                        63

<210> SEQ ID NO 13
<211> LENGTH: 29

<212> TYPE: PRT
<213> ORGANISM: Artificial Sequence
<220> FEATURE:
<223> OTHER INFORMATION: ErbB receptor dimerization arm

<400> SEQUENCE: 13

Cys Pro Pro Leu Met Leu Tyr Asn Pro Thr Thr Tyr Gln Met Asp Val
1               5                   10                  15

Asn Pro Glu Gly Lys Tyr Ser Phe Gly Ala Thr Cys Val
            20                  25

<210> SEQ ID NO 14
<211> LENGTH: 29
<212> TYPE: PRT
<213> ORGANISM: Artificial Sequence
<220> FEATURE:
<223> OTHER INFORMATION: ErbB receptor dimerization arm

<400> SEQUENCE: 14

Cys Pro Ala Leu Val Thr Tyr Asn Thr Asp Thr Phe Glu Ser Met Pro
1               5                   10                  15

Asn Pro Glu Gly Arg Tyr Thr Phe Gly Ala Ser Cys Val
            20                  25

<210> SEQ ID NO 15
<211> LENGTH: 29
<212> TYPE: PRT
<213> ORGANISM: Artificial Sequence
<220> FEATURE:
<223> OTHER INFORMATION: ErbB receptor dimerization arm

<400> SEQUENCE: 15

Cys Pro Gln Pro Leu Val Tyr Asn Lys Leu Thr Phe Gln Leu Glu Pro
1               5                   10                  15

Asn Pro His Thr Lys Tyr Gln Tyr Gly Gly Val Cys Val
            20                  25

<210> SEQ ID NO 16
<211> LENGTH: 29
<212> TYPE: PRT
<213> ORGANISM: Artificial Sequence
<220> FEATURE:
<223> OTHER INFORMATION: ErbB receptor dimerization arm

<400> SEQUENCE: 16

Cys Pro Gln Thr Phe Val Tyr Asn Pro Thr Thr Phe Gln Leu Glu Met
1               5                   10                  15

Asn Phe Asn Ala Lys Tyr Thr Tyr Gly Ala Phe Cys Val
            20                  25

<210> SEQ ID NO 17
<211> LENGTH: 28
<212> TYPE: DNA
<213> ORGANISM: Artificial sequence
<220> FEATURE:
<223> OTHER INFORMATION: 5' 12bp RSS

<400> SEQUENCE: 17
ggtttttgtt aagggctgta tcactgtg                                      28

<210> SEQ ID NO 18
<211> LENGTH: 28
<212> TYPE: DNA
<213> ORGANISM: Artificial sequence
<220> FEATURE:

<223> OTHER INFORMATION: 3' 12bp RSS

<400> SEQUENCE: 18
cacagtgctc cagggctgaa caaaaacc					28

<210> SEQ ID NO 19
<211> LENGTH: 32
<212> TYPE: PRT
<213> ORGANISM: Artificial sequences
<220> FEATURE:
<223> OTHER INFORMATION: Anti-TPO receptor peptide plus flanking
      sequences

<400> SEQUENCE: 19

Ala Arg Asp Leu Val Asp Ile Glu Gly Pro Thr Leu Arg Gln Trp Leu
1               5                   10                  15
Ala Ala Arg Ala His Gly Arg Glu Tyr Tyr Tyr Tyr Tyr Met Asp Val
            20                  25                  30

<210> SEQ ID NO 20
<211> LENGTH: 32
<212> TYPE: PRT
<213> ORGANISM: Artificial sequences
<220> FEATURE:
<223> OTHER INFORMATION: Anti-TPO receptor peptide plus flanking
      sequences

<400> SEQUENCE: 20

Ala Arg Asp Pro Thr Leu Trp Leu Ile Glu Gly Pro Thr Leu Arg Gln
1               5                   10                  15
Trp Leu Ala Ala Arg Ala Glu Tyr Tyr Tyr Tyr Tyr Met Asp Val
            20                  25                  30

<210> SEQ ID NO 21
<211> LENGTH: 26
<212> TYPE: PRT
<213> ORGANISM: Artificial sequences
<220> FEATURE:
<223> OTHER INFORMATION: Anti-TPO receptor peptide plus flanking
      sequences

<400> SEQUENCE: 21

Ala Gly Pro Leu Arg Ile Glu Gly Pro Thr Leu Arg Gln Trp Leu Ala
1               5                   10                  15
Ala Arg Ala Ser Leu Tyr Tyr Met Asp Val
            20                  25

<210> SEQ ID NO 22
<211> LENGTH: 32
<212> TYPE: PRT
<213> ORGANISM: Artificial sequences
<220> FEATURE:
<223> OTHER INFORMATION: Anti-TPO receptor peptide plus flanking
      sequences

<400> SEQUENCE: 22

Ala Arg Ala Lys Ser Ser Gln Ile Glu Gly Pro Thr Leu Arg Gln Trp
1               5                   10                  15
Leu Ala Ala Arg Ala Glu Leu Arg Leu Gln His Tyr Tyr Met Asp Val
            20                  25                  30

<210> SEQ ID NO 23
<211> LENGTH: 28
<212> TYPE: PRT
<213> ORGANISM: Artificial sequences -continued

```
<220> FEATURE:
<223> OTHER INFORMATION: Anti-TPO receptor peptide plus flanking
      sequences

<400> SEQUENCE: 23

Ala Arg Lys Pro Gln Ala Ile Glu Gly Pro Thr Leu Arg Gln Trp Leu
1               5                   10                  15

Ala Ala Arg Ala Leu Gly Asn Tyr Tyr Met Asp Val
            20                  25

<210> SEQ ID NO 24
<211> LENGTH: 30
<212> TYPE: PRT
<213> ORGANISM: Artificial sequences
<220> FEATURE:
<223> OTHER INFORMATION: Anti-TPO receptor peptide plus flanking
      sequences

<400> SEQUENCE: 24

Ala Arg Thr Leu Arg Ile Glu Gly Pro Thr Leu Arg Gln Trp Leu Ala
1               5                   10                  15

Ala Arg Ala Pro Ala Ala Tyr Tyr Tyr Tyr Tyr Met Asp Val
            20                  25                  30

<210> SEQ ID NO 25
<211> LENGTH: 31
<212> TYPE: PRT
<213> ORGANISM: Artificial sequences
<220> FEATURE:
<223> OTHER INFORMATION: Anti-TPO receptor peptide plus flanking
      sequences

<400> SEQUENCE: 25

Ala Ser Cys Arg Ser Ile Glu Gly Pro Thr Leu Arg Gln Trp Leu Ala
1               5                   10                  15

Ala Arg Ala Cys Leu Asp Leu Ile Gly Tyr Tyr Tyr Met Asp Val
            20                  25                  30

<210> SEQ ID NO 26
<211> LENGTH: 418
<212> TYPE: DNA
<213> ORGANISM: Artificial sequences
<220> FEATURE:
<223> OTHER INFORMATION: Anti-TPO receptor peptide plus flanking
      sequences

<400> SEQUENCE: 26
caggtgcagc tggtgcagtc tggcgccgaa gtgaagaaac cggcagcag cgtgaaggtg      60 tcctgcaagg ccagcggcgg caccttcagc agctacgcca tcagctgggt ccgccaggct    120
cctggacagg gactggaatg gatgggcggc atcatcccca tcttcggcac cgccaactac    180
gcccagaaat tccagggcag agtgaccatc accgccgacg agagcaccag caccgcctac    240
atggaactga gcagccttcg aagcgaggac accgctgtgt attactgtgc gagagatctt    300
gttgatatcg agggccctac cctgagacag tggctggccg ctagagctca tgggcgggag    360
tactactact actacatgga cgtctggggc aaagggacca cggtcaccgt gtcctcag      418

<210> SEQ ID NO 27
<211> LENGTH: 418
<212> TYPE: DNA
<213> ORGANISM: Artificial sequences
<220> FEATURE:
<223> OTHER INFORMATION: Anti-TPO receptor peptide plus flanking
      sequences
```

<400> SEQUENCE: 27

```
caggtgcagc tggtgcagtc tggcgccgaa gtgaagaaac ccggcagcag cgtgaaggtg    60
tcctgcaagg ccagcggcgg caccttcagc agctacgcca tcagctgggt ccgccaggct   120
cctggacagg gactggaatg gatgggcggc atcatcccca tcttcggcac cgccaactac   180
gcccagaaat tccagggcag agtgaccatc accgccgacg agagccacag caccgcctac   240
atggaactga gcagccttcg aagcgaggac accgctgtgt attactgtgc gagagatcct   300
actctgtggc tgatcgaggg ccctaccctg agacagtggc tggccgctcg agctgagtac   360
tactactact actacatgga cgtctggggc aaagggacca cggtcaccgt gtcctcag    418
```

<210> SEQ ID NO 28
<211> LENGTH: 10231
<212> TYPE: DNA
<213> ORGANISM: Artificial Sequence
<220> FEATURE:
<223> OTHER INFORMATION: Peptide grafting acceptor vector

<400> SEQUENCE: 28

```
ctaaattgta agcgttaata ttttgttaaa attcgcgtta aatttttgtt aaatcagctc    60
attttttaac caataggccg aaatcggcaa aatcccttat aaatcaaaag aatagaccga   120
gatagggttg agtggccgct acagggcgct cccattcgcc attcaggctg cgcaactgtt   180
gggaagggcg tttcggtgcg ggcctcttcg ctattacgcc agctggcgaa aggggatgt   240
gctgcaaggc gattaagttg ggtaacgcca gggttttccc agtcacgacg ttgtaaaacg   300
acggccagtg agcgcgacgt aatacgactc actatagggc gaattggcgg aaggccgtca   360
aggcctaggc gcgcctgaat aacttcgtat agcatacatt atagcaattt atcgaaaaag   420
cctgaactca ccgcgacatc cgtggagaaa ttcctcatcg aaaaattcga ctccgtgtcc   480
gatctcatgc agctgtccga gggcgaggag agtagagcat tctcattcga gtgggcggg   540
agaggctacg tgctgagagt gaactcttgt gccgacggct tctacaagga ccgatacgtc   600
taccggcatt tgcttccgc cgctctgcct attccagaag tcctggacat tggggagttt   660
agcgagtccc tcacttactg tattagccgg cgagcccagg gagtgacact ccaggatctg   720
cctgaaactg aactgcctgc tgtgctccag cctgtcgctg aggcaatgga tgctattgct   780
gctgccgatc tgagtcagac tagcggattc ggcccatttg accccaggg cattggccag   840
tacacaacat ggcgagactt catctgtgct atcgccgatc ctcacgtgta ccattggcag   900
actgtgatgg acgatactgt gtctgcttct gtggcacagg cactcgacga actcatgctg   960
tgggctgagg actgtcctga agtgagacat ctggtccatg ccgatttttg ctccaacaat  1020
gtgctcaccg ataacgggag aatcactgcc gtgatcgact ggagcgaggc aatgtttggc  1080
gattcccagt acgaagtggc caacatcttc ttttgcggc cttggctggc ttgtatggaa  1140
cagcagaccc ggtactttga acggcgccac cctgagctgg ctgggagtcc tagactgaga  1200
gcctacatgc tccgaattgg cctggatcag ctctaccagt cactggtgga tggcaatttc  1260
gacgatgctg cttgggcaca ggggcgctgt gatgctattg tccgatccgg cgctggaact  1320
gtggggagaa cacagatcgc taggagatcc gctgctgtct ggaccgatgg atgtgtggaa  1380
gtgctggccg atagtggaaa ccggaggcct tcaacccgac cccgggcaaa ggagtaatga  1440
ccgtttaaac ccgctgatca gcctcgactg tgccttctag ttgccagcca tctgttgttt  1500
gcccctcccc cgtgccttcc ttgaccctgg aaggtgccac tcccactgtc ctttcctaat  1560
```

```
aaaatgagga aattgcatcg cattgtctga gtaggtgtca ttctattctg gggggtgggg      1620
tggggcagga cagcaagggg gaggattggg aagacaatag caggcatgct ggggatgcgg      1680
tgggctctat ggggatcccg cgttgacatt gattattgac tagttattaa tagtaatcaa      1740
ttacggggtc attagttcat agcccatata tggagttccg cgttacataa cttacggtaa      1800
atggcccgcc tggctgaccg cccaacgacc cccgcccatt gacgtcaata atgacgtatg      1860
ttcccatagt aacgccaata gggactttcc attgacgtca atgggtggag tatttacggt      1920
aaactgccca cttggcagta catcaagtgt atcatatgcc aagtacgccc cctattgacg      1980
tcaatgacgg taaatggccc gcctggcatt atgcccagta catgacctta tgggactttc      2040
ctacttggca gtacatctac gtattagtca tcgctattac catggtgatg cggttttggc      2100
agtacatcaa tgggcgtgga tagcggtttg actcacgggg atttccaagt ctccacccca      2160
ttgacgtcaa tgggagtttg ttttggcacc aaaatcaacg ggactttcca aaatgtcgta      2220
acaactccgc cccattgacg caaatgggcg gtaggcgtgt acggtgggag gtctatataa      2280
gcagagctct ctggctaact agagaaccca ctgcttactg ctcgacgatc tgatcaagag      2340
acaggataag gagccgccac catggagttt ggctgagct ggcttttttct tgtggctatt      2400 ttaaaggtg tccagtgtga agtgcagctg ctggaaagcg gcggaggcct ggtgcagcct      2460
ggcggcagcc tgagactgtc ttgcgccgcc agcggcttca ccttcagcag ctacgccatg      2520
agctgggtcc gccaggcccc tggcaaggga ctcgaatggg tgtccgccat cagcggcagc      2580
ggcggcagca cctactacgc cgacagcgtg aagggccggt tcaccatcag ccgggacaac      2640
agcaagaaca ccctgtacct gcagatgaac agcctgcggg ccgaggacac cgccgtatat      2700
tactgtgcga agacacagt ggtagtactc cactgtctgg gtgtacaaaa acctccctgc      2760
acgcctctct aacctcacaa ttctgtggcg gccgcgccgc caccatgatt gaacaagatg      2820
gattgcacgc aggttctccg gccgcttggg tggagaggct attcggctat gactgggcac      2880
aacagacaat cggctgctct gatgccgccg tgttccggct gtcagcgcag gggcgcccgg      2940 ttcttttgt caagaccgac ctgtccggtg ccctgaatga actgcaggac gaggcagcgc      3000
ggctatcgtg gctggccacg acgggcgttc cttgcgcagc tgtgctcgac gttgtcactg      3060
aagcgggaag ggactggctg ctattgggcg aagtgccggg gcaggatctc ctgtcatctc      3120
accttgctcc tgccgagaaa gtatccatca tggctgatgc aatgcggcgg ctgcatacgc      3180
ttgatccggc tacctgccca ttcgaccacc aagcgaaaca tcgcatcgag cgagcacgta      3240
ctcggatgga agccggtctt gtcgatcagg tgagtacagg aggtggagag tacgcgtaac      3300
acttaagcgt ctctccaaga tccttttttaa cccatcacat atacctgccg ttcactatta      3360
tttagtgaaa tgagatatta tgatattttc tgaattgtga ttaaaaaggc aactttatgc      3420
ccatgcaaca gaaactataa aaatacaga gaatgaaaag aaacagatag atttttttagt      3480 tctttaggcc cgtagtctgc aaatccttt atgatttctct atcaaacaaa agaggaaaat      3540
agaccagttg caatccaaac gagagtctaa tagaatgagg tcgaaaagta aatcgcgcgg      3600
gtttgttact gataaagcag gcaagaccta aaatgtgtaa agggcaaagt gtatactttg      3660
gcgtcacccc ttcatatttt taggtctttt tttattgtgc gtaactaact tgccatcttc      3720
aaacaggagg gctggaagaa gcagaccgct aacacagtac ataaaaaagg agacatgaac      3780
gatgaacatc aaaaagtttg caaaacaagc aacagtatta acctttacta ccgcactgct      3840
ggcaggaggc gcaactcaag cgtttgcgaa agaaacgaac caaaagccat ataaggaaac      3900
atacggcatt tcccatatta cacgccatga tatgctgcaa atccctgaac agcaaaaaaa      3960
```

```
tgaaaaatat caagttcctg agttcgattc gtccacaatt aaaaatatct cttctgcaaa   4020
aggcctggac gtttgggaca gctggccatt acaaaacgct gacggcactg tcgcaaacta   4080
tcacggctac cacatcgtct ttgcattagc cggagatcct aaaaatgcgg atgacacatc   4140
gatttacatg ttctatcaaa aagtcggcga aacttctatt gacagctgga aaaacgctgg   4200
ccgcgtcttt aaagacagcg acaaattcga tgcaaatgat tctatcctaa agaccaaac   4260 acaagaatgg tcaggttcag ccacatttac atctgacgga aaaatccgtt tattctacac   4320
tgatttctcc ggtaaacatt acggcaaaca aacactgaca actgcacaag ttaacgtatc   4380
agcatcagac agctctttga acatcaacgg tgtagaggat tataaatcaa tctttgacgg   4440
tgacggaaaa acgtatcaaa atgtacagca gttcatcgat gaaggcaact acagctcagg   4500
cgacaaccat acgctgagag atcctcacta cgtagaagat aaaggccaca aatacttagt   4560
atttgaagca aacactggaa ctgaagatgg ctaccaaggc gaagaatctt tatttaacaa   4620
agcatactat ggcaaaagca catcattctt ccgtcaagaa agtcaaaaac ttctgcaaag   4680
cgataaaaaa cgcacggctg agttagcaaa cggcgctctc ggtatgattg agctaaacga   4740
tgattacaca ctgaaaaaag tgatgaaacc gctgattgca tctaacacag taacagatga   4800
aattgaacgc gcgaacgtct ttaaaatgaa cggcaaatgg tatctgttca ctgactcccg   4860
cggatcaaaa atgacgattg acggcattac gtctaacgat atttacatgc ttggttatgt   4920
ttctaattct ttaactggcc catacaagcc gctgaacaaa actggccttg tgttaaaaat   4980
ggatcttgat cctaacgatg taacctttac ttactcacac ttcgctgtac ctcaagcgaa   5040
aggaaacaat gtcgtgatta caagctatat gacaaacaga ggattctacg cagacaaaca   5100
atcaacgttt gcgcctagct tcctgctgaa catcaaaggc aagaaaacat ctgttgtcaa   5160
agacagcatc cttgaacaag gacaattaac agttaacaaa taaaaacgca aagaaaatg   5220 ccgattatgg tgcactctca gtacaatctg ggtaagagac gtccggaggc cagcccttct   5280
catgttcaga gaacatggtt aactggttaa gtcatgtcgt cccacaggat gatctggacg   5340
aagagcatca ggggctcgcg ccagccgaac tgttcgccag gctcaaggcg cgcatgcccg   5400
acggcgagga tctcgtcgtg acccatggcg atgcctgctt gccgaatatc atggtggaaa   5460
atggccgctt ttctggattc atcgactgtg gccggctggg tgtggcggac cgctatcagg   5520
acatagcgtt ggctacccgt gatattgctg aagagcttgg cggcgaatgg gctgaccgct   5580
tcctcgtgct ttacggtatc gccgctcccg attcgcagcg catcgccttc tatcgccttc   5640
ttgacgagtt cttctgagtc gactgcagga gtcccactgc accccctcc cagtcttctc   5700 tgtccaggca ccaggccagg tatctggggt gtgcagccgg cctgggtctg gcctgaggcc   5760
acaagcccgg gggtctgtgt ggctgggac agggacgccg gctgcctctg ctctgtgctt   5820
gggccatgtg acccattcga gtgtcctgca cgggcacagg ttttgtaca cccagacagt   5880 ggagtactac cactgtgact actttgacta ctggggccag gaaccctgg tcaccgtgtc   5940 ctcaggtaag atggctttcc ttctgcctcc tttctctggg cccagcgtcc tctgtcctgg   6000
agctgggaga taatgtccgg gggctccttg gtctgcgctg gcaaagggt gggcagagtc   6060 atgcttgtgc tggggacaaa atgaccttgg gacacgggg tggctgccac ggccggcccg   6120
ggacagtcgg agagtcaggt tgctagcgaa cctcgcggac agttaagaac ccaggggcct   6180
ctgcgccctg ggcccagctc tgtcccacac gcggtcaca tggcaccacc tctcttgcag   6240
cctccaccaa gggcccatcg gtcttccccc tggcacccctc ctccaagagc acctctgggg   6300
```

```
gcacagcggc cctgggctgc ctggtcaagg actacttccc cgaaccggtg acggtgtcgt    6360
ggaactcagg cgccctgacc agcggcgtgc ataccttccc ggctgtccta cagtcctcag    6420
gactctactc cctcagcagc gtggtgaccg tgccctccag cagcttgggc acccagacct    6480
acatctgcaa cgtgaatcac aagcccagca acaccaaggt ggacaagaaa gttgagccca    6540
aatcttgtga caaaactcac acatgcccac cgtgcccagc acctgaactc ctggggggac    6600
cgtcagtctt cctcttcccc ccaaaaccca aggacaccct catgatctct agaacccctg    6660
aggtcacatg cgtggtggtg gacgtgagcc acgaagaccc tgaggtcaag ttcaactggt    6720
acgtggacgg cgtggaggtg cataatgcca agacaaagcc gcgggaggag cagtacaaca    6780
gcacgtaccg tgtggtcagc gtcctcaccg tcctgcacca ggactggctg aatggcaagg    6840
agtacaagtg caaggtgtcc aacaaagccc tcccagcccc catcgagaaa accatctcca    6900
aagccaaagg gcagccccga gaaccacagg tgtacaccct gcccccatcc cgggatgagc    6960
tgaccaagaa ccaggtcagc ctgacctgcc tggtcaaagg cttctatccc agcgacatcg    7020
ccgtggagtg ggagagcaat gggcagccgg agaacaacta caagaccacg cctcccgtgc    7080
tggactccga cggctccttc ttcctctaca gcaagctcac cgtggacaag tctagatggc    7140 agcagggaa cgtcttctca tgctccgtga tgcatgagc tctgcacaac cactacacgc    7200
agaagagcct ctccctgtct ccgggcaaac tggctctcat tgtcctgggc ggcgtggctg    7260
gcctgctgct gtttattggg ctgggcatct tcttttgtgt ccggtgtcgg cataggaggc    7320
gccaaggagg tggcggatct ggaggggag gatctggagg gggctcagga tcaggggag    7380 gatctggagg cggatcaact gagtacaaac ccactgtgag gctcgctact agagatgatg    7440
tgcctagagc tgtccgaact ctggctgctg ccttcgccga ttaccctgcc actcgccata    7500
ccgtcgatcc cgatcgccac attgaacgag tcaccgaact ccaggagctg tttctcacta    7560
gagtcgggct ggatattggc aaagtctggg tggccgatga cggagccgct gtcgctgtgt    7620
ggactacacc tgagtctgtg gaggctggcg ccgtgtttgc tgaaattgga cctcggatgg    7680
ctgaactgtc tggatctcga ctggctgccc agcagcagat ggagggactg ctggcacccc    7740
atagaccaaa ggaacctgcc tggtttctgg caactgtggg agtgtcaccc gatcatcagg    7800
gcaaaggact gggatctgcc gtggtgctcc ctggcgtgga ggccgctgaa cgagctggcg    7860
tccccgcttt tctcgaaact ctgcccccc gaaatctccc tttctacgaa cgactgggat    7920
tcactgtcac cgccgatgtc gaagtgcctg aggggcctag aacatggtgt atgacccgga    7980
aacccggagc ttaaccgttt aaacccgctg atcagcctcg actgtgcctt ctagttgcca    8040
gccatctgtt gtttgcccct cccccgtgcc ttccttgacc ctggaaggtg ccactcccac    8100
tgtcctttcc taataaaatg aggaaattgc atcgcattgt ctgagtaggt gtcattctat    8160 tctgggggt ggggtggggc aggacagcaa ggggaggat tggaagaca atagcaggca    8220 tgctggggat gcggtgggct ctatggctcg agttaattaa ctggcctcat ggccttccg    8280 ctcactgccc gctttccagt cgggaaacct gtcgtgccag ctgcattaac atggtcatag    8340
ctgtttcctt gcgtattggg cgctctccgc ttcctcgctc actgactcgc tgcgctcggt    8400
cgttcgggta agcctggggg tgcctaatga gcaaaaggcc agcaaaaggc caggaaccgt    8460
aaaaaggccg cgttgctggc gttttccat aggctccgcc ccctgacga gcatcacaaa    8520 aatcgacgct caagtcagag gtggcgaaac ccgacaggac tataaagata ccaggcgttt    8580 cccccctggaa gctccctcgt gcgctctcct gttccgaccc tgccgcttac cggatacctg    8640
tccgcctttc tcccttcggg aagcgtggcg ctttctcata gctcacgctg taggtatctc    8700
```

```
agttcggtgt aggtcgttcg ctccaagctg ggctgtgtgc acgaaccccc cgttcagccc    8760
gaccgctgcg ccttatccgg taactatcgt cttgagtcca acccggtaag acacgactta    8820
tcgccactgg cagcagccac tggtaacagg attagcagag cgaggtatgt aggcggtgct    8880
acagagttct tgaagtggtg gcctaactac ggctacacta agaacagtt atttggtatc     8940 tgcgctctgc tgaagccagt taccttcgga aaaagagttg gtagctcttg atccggcaaa    9000
caaaccaccg ctggtagcgg tggtttttt gtttgcaagc agcagattac gcgcagaaaa     9060
aaaggatctc aagaagatcc tttgatcttt tctacggggt ctgacgctca gtggaacgaa    9120
aactcacgtt aagggatttt ggtcatgaga ttatcaaaaa ggatcttcac ctagatcctt    9180
ttaaattaaa aatgaagttt taaatcaatc taaagtatat atgagtaaac ttggtctgac    9240
agttaccaat gcttaatcag tgaggcacct atctcagcga tctgtctatt tcgttcatcc    9300
atagttgcct gactccccgt cgtgtagata actacgatac gggagggctt accatctggc    9360
cccagtgctg caatgatacc gcgagaacca cgctcaccgg ctccagattt atcagcaata    9420
aaccagccag ccggaagggc cgagcgcaga agtggtcctg caactttatc cgcctccatc    9480
cagtctatta attgttgccg ggaagctaga gtaagtagtt cgccagttaa tagtttcgc     9540 aacgttgttg ccattgctac aggcatcgtg gtgtcacgct cgtcgtttgg tatggcttca    9600
ttcagctccg gttcccaacg atcaaggcga gttacatgat cccccatgtt gtgcaaaaaa    9660
gcggttagct ccttcggtcc tccgatcgtt gtcagaagta agttggccgc agtgttatca    9720
ctcatggtta tggcagcact gcataattct cttactgtca tgccatccgt aagatgcttt    9780
tctgtgactg gtgagtactc aaccaagtca ttctgagaat agtgtatgcg gcgaccgagt    9840
tgctcttgcc cggcgtcaat acgggataat accgcgccac atagcagaac tttaaaagtg    9900
ctcatcattg gaaaacgttc ttcggggcga aaactctcaa ggatcttacc gctgttgaga    9960
tccagttcga tgtaacccac tcgtgcaccc aactgatctt cagcatcttt tactttcacc   10020
agcgtttctg ggtgagcaaa aacaggaagg caaaatgccg caaaaaaggg aataagggcg   10080
acacggaaat gttgaatact catactcttc cttttcaat attattgaag catttatcag    10140
ggttattgtc tcatgagcgg atacatattt gaatgtattt agaaaaataa acaaataggg   10200
gttccgcgca catttccccg aaaagtgcca c                                  10231
```

<210> SEQ ID NO 29
<211> LENGTH: 179
<212> TYPE: DNA
<213> ORGANISM: Artificial Sequence
<220> FEATURE:
<223> OTHER INFORMATION: RGD peptide #1 plus flanking sequences

<400> SEQUENCE: 29

```
cgtctctcca agtgcaaagg acaggaggt ttttgttaag ggctgtatca ctgtgtatac      60
catcactgtg tatgctgtca ctggccgtgg agacagcccc gcaagcagca agccaatttc    120
cattcacagt gatacagccc ttaacaaaaa cccctactgc aacctggcgg taagagacg     179
```

<210> SEQ ID NO 30
<211> LENGTH: 69
<212> TYPE: DNA
<213> ORGANISM: Artificial Sequence
<220> FEATURE:
<223> OTHER INFORMATION: RGD peptide #1

<400> SEQUENCE: 30

```
tataccatca ctgtgtatgc tgtcactggc cgtggagaca gccccgcaag cagcaagcca    60
atttccatt                                                           69
```

<210> SEQ ID NO 31
<211> LENGTH: 23
<212> TYPE: PRT
<213> ORGANISM: Artificial Sequence
<220> FEATURE:
<223> OTHER INFORMATION: RGD peptide #1

<400> SEQUENCE: 31

Tyr Thr Ile Thr Val Tyr Ala Val Thr Gly Arg Gly Asp Ser Pro Ala
1               5                   10                  15

Ser Ser Lys Pro Ile Ser Ile
            20

<210> SEQ ID NO 32
<211> LENGTH: 149
<212> TYPE: DNA
<213> ORGANISM: Artificial Sequence
<220> FEATURE:
<223> OTHER INFORMATION: RGD peptide #2 plus flanking sequences

<400> SEQUENCE: 32

```
cgtctctcca agtgcaaagg gacaggaggt ttttgttaag ggctgtatca ctgtgtatgc    60
tgtcactggc cgtggagaca gccccgcaag cagccacagt gatacagccc ttaacaaaaa    120
cccctactgc aacctggcgg taagagacg                                     149
```

<210> SEQ ID NO 33
<211> LENGTH: 39
<212> TYPE: DNA
<213> ORGANISM: Artificial Sequence
<220> FEATURE:
<223> OTHER INFORMATION: RGD peptide #2

<400> SEQUENCE: 33

```
tatgctgtca ctggccgtgg agacagcccc gcaagcagc                           39
```

<210> SEQ ID NO 34
<211> LENGTH: 13
<212> TYPE: PRT
<213> ORGANISM: Artificial Sequence
<220> FEATURE:
<223> OTHER INFORMATION: RGD peptide #2

<400> SEQUENCE: 34

Tyr Ala Val Thr Gly Arg Gly Asp Ser Pro Ala Ser Ser
1               5                   10

<210> SEQ ID NO 35
<211> LENGTH: 84
<212> TYPE: DNA
<213> ORGANISM: Artificial Sequence
<220> FEATURE:
<223> OTHER INFORMATION: Modified fibronectin

<400> SEQUENCE: 35

```
tataccatca cgtggagacc tgtgtatgct gtcactggcc gtggagacag ccccgcggag    60
acaagcagca agccaatttc catt                                          84
```

<210> SEQ ID NO 36
<211> LENGTH: 203
<212> TYPE: DNA

<213> ORGANISM: Artificial Sequence
<220> FEATURE:
<223> OTHER INFORMATION: GLP-1 peptide grafting cassette

<400> SEQUENCE: 36
cgtctctcca agtgcaaagg gacaggaggt ttttgttaag ggctgtatca ctgtgcatgc 60
cgagggcacc tttaccagtg acgtgagtag ctacctagaa ggccaggccg ccaaagagtt 120
tatcgcctgg ctcgtgaagg gcagaggcca cagtgataca gcccttaaca aaaaccccta 180
ctgcaacctg gcggtaagag acg 203

<210> SEQ ID NO 37
<211> LENGTH: 173
<212> TYPE: DNA
<213> ORGANISM: Artificial Sequence
<220> FEATURE:
<223> OTHER INFORMATION: GLP-1 peptide grafting cassette

<400> SEQUENCE: 37
cgtctctcca agtgcaaagg gacaggaggt ttttgttaag ggctgtatca ctgtgaccag 60
tgacgtgagt agctacctag aaggccaggc cgctaaagag tttatcgcct ggctcgtgca 120
cagtgataca gcccttaaca aaaaccccta ctgcaacctg gcggtaagag acg 173

<210> SEQ ID NO 38
<211> LENGTH: 31
<212> TYPE: PRT
<213> ORGANISM: Artificial Sequence
<220> FEATURE:
<223> OTHER INFORMATION: GLP-1 peptide grafting cassette

<400> SEQUENCE: 38

His Ala Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 39
<211> LENGTH: 21
<212> TYPE: PRT
<213> ORGANISM: Artificial Sequence
<220> FEATURE:
<223> OTHER INFORMATION: GLP-1 peptide grafting cassette

<400> SEQUENCE: 39

Thr Ser Asp Val Ser Ser Tyr Leu Glu Gly Gln Ala Ala Lys Glu Phe
1 5 10 15

Ile Ala Trp Leu Val
20

<210> SEQ ID NO 40
<211> LENGTH: 227
<212> TYPE: DNA
<213> ORGANISM: Artificial Sequence
<220> FEATURE:
<223> OTHER INFORMATION: Exendin-4 peptide grafting cassette

<400> SEQUENCE: 40
cgtctctcca agtgcaaagg gacaggaggt ttttgttaag ggctgtatca ctgtgcatgg 60
cgagggcacc ttcaccagcg acctgagcaa gcagatggaa gaggaagccg tgcggctatt 120
cattgagtgg ctgaagaatg gcggccctag ctctggcgcc cctcctcctt ctcacagtga 180
tacagccctt aacaaaaacc cctactgcaa cctggcggta agagacg 227

<210> SEQ ID NO 41
<211> LENGTH: 200
<212> TYPE: DNA
<213> ORGANISM: Artificial Sequence
<220> FEATURE:
<223> OTHER INFORMATION: Exendin-4 peptide grafting cassette

<400> SEQUENCE: 41

```
cgtctctcca agtgcaaagg gacaggaggt ttttgttaag ggctgtatca ctgtgctgag     60
caagcagatg gaagaggaag ccgtgcggct attcattgag tggctgaaga atggcggccc    120
tagctctggc gcccctcctc cttctcacag tgatacagcc cttaacaaaa acccctactg    180
caacctggcg gtaagagacg                                                200
```

<210> SEQ ID NO 42
<211> LENGTH: 149
<212> TYPE: DNA
<213> ORGANISM: Artificial Sequence
<220> FEATURE:
<223> OTHER INFORMATION: Exendin-4 peptide grafting cassette

<400> SEQUENCE: 42

```
cgtctctcca agtgcaaagg gacaggaggt ttttgttaag ggctgtatca ctgtggaaga     60
ggaagccgtg agactattca ttgagtggct gaagcacagt gatacagccc ttaacaaaaa    120
cccctactgc aacctggcgg taagagacg                                      149
```

<210> SEQ ID NO 43
<211> LENGTH: 39
<212> TYPE: PRT
<213> ORGANISM: Artificial Sequence
<220> FEATURE:
<223> OTHER INFORMATION: Exendin-4 peptide grafting cassette

<400> SEQUENCE: 43

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 44
<211> LENGTH: 30
<212> TYPE: PRT
<213> ORGANISM: Artificial Sequence
<220> FEATURE:
<223> OTHER INFORMATION: Exendin-4 peptide grafting cassette

<400> SEQUENCE: 44

```
Leu Ser Lys Gln Met Glu Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30
```

<210> SEQ ID NO 45
<211> LENGTH: 13
<212> TYPE: PRT
<213> ORGANISM: Artificial Sequence
<220> FEATURE:
<223> OTHER INFORMATION: Exendin-4 peptide grafting cassette

<400> SEQUENCE: 45

Glu Glu Glu Ala Val Arg Leu Phe Ile Glu Trp Leu Lys
1               5                   10

<210> SEQ ID NO 46
<211> LENGTH: 75
<212> TYPE: DNA
<213> ORGANISM: Artificial sequence
<220> FEATURE:
<223> OTHER INFORMATION: IL-8 peptide

<400> SEQUENCE: 46
gctaaagaac ttagatgtca gtgcataaag acatactcca aacctttcca ccccaaattt      60
atcaaagaac tgaga                                                       75

<210> SEQ ID NO 47
<211> LENGTH: 25
<212> TYPE: PRT
<213> ORGANISM: Artificial sequence
<220> FEATURE:
<223> OTHER INFORMATION: IL-8 peptide

<400> SEQUENCE: 47

Ala Lys Glu Leu Arg Cys Gln Cys Ile Lys Thr Tyr Ser Lys Pro Phe
1               5                   10                  15

His Pro Lys Phe Ile Lys Glu Leu Arg
            20                  25

<210> SEQ ID NO 48
<211> LENGTH: 23
<212> TYPE: PRT
<213> ORGANISM: Artificial sequence
<220> FEATURE:
<223> OTHER INFORMATION: Gro-alpha peptide

<400> SEQUENCE: 48

Ala Thr Glu Leu Arg Cys Gln Cys Leu Gln Thr Leu Gln Gly Ile His
1               5                   10                  15

Pro Lys Asn Ile Gln Ser Val
            20

<210> SEQ ID NO 49
<211> LENGTH: 69
<212> TYPE: DNA
<213> ORGANISM: Artificial sequence
<220> FEATURE:
<223> OTHER INFORMATION: Gro-alpha peptide

<400> SEQUENCE: 49
gccactgaac tgcgctgcca gtgcttgcag accctgcagg gaattcaccc caagaacatc      60
caaagtgtg                                                              69

<210> SEQ ID NO 50
<211> LENGTH: 30
<212> TYPE: DNA
<213> ORGANISM: Artificial sequence
<220> FEATURE:
<223> OTHER INFORMATION: LL-37 peptide

<400> SEQUENCE: 50
ctgctaggtg atttcttccg gaaatctaaa                                       30

<210> SEQ ID NO 51
<211> LENGTH: 84

```
<212> TYPE: DNA
<213> ORGANISM: Artificial sequence
<220> FEATURE:
<223> OTHER INFORMATION: ErbB2 peptide #1

<400> SEQUENCE: 51
tgcccagccc tggtaaccta caacacagac acgtttgagt ccatgcccaa tcccgagggc    60
cggtatacat tcggcgccag ctgt                                          84

<210> SEQ ID NO 52
<211> LENGTH: 28
<212> TYPE: PRT
<213> ORGANISM: Artificial sequence
<220> FEATURE:
<223> OTHER INFORMATION: ErbB2 peptide #1

<400> SEQUENCE: 52

Cys Pro Ala Leu Val Thr Tyr Asn Thr Asp Thr Phe Glu Ser Met Pro
1               5                   10                  15

Asn Pro Glu Gly Arg Tyr Thr Phe Gly Ala Ser Cys
            20                  25

<210> SEQ ID NO 53
<211> LENGTH: 96
<212> TYPE: DNA
<213> ORGANISM: Artificial sequence
<220> FEATURE:
<223> OTHER INFORMATION: ErbB2 peptide #2

<400> SEQUENCE: 53
ctgcactgcc cagccctggt aacctacaac acagacacgt ttgagtccat gcccaatccc    60
gagggccggt atacattcgg cgccagctgt gtgact                             96

<210> SEQ ID NO 54
<211> LENGTH: 32
<212> TYPE: PRT
<213> ORGANISM: Artificial sequence
<220> FEATURE:
<223> OTHER INFORMATION: ErbB2 peptide #2

<400> SEQUENCE: 54

Leu His Cys Pro Ala Leu Val Thr Tyr Asn Thr Asp Thr Phe Glu Ser
1               5                   10                  15

Met Pro Asn Pro Glu Gly Arg Tyr Thr Phe Gly Ala Ser Cys Val Thr
            20                  25                  30

<210> SEQ ID NO 55
<211> LENGTH: 84
<212> TYPE: DNA
<213> ORGANISM: Artificial sequence
<220> FEATURE:
<223> OTHER INFORMATION: ErbB2 peptide #3

<400> SEQUENCE: 55 tgcccccac tcatgctcta caaccccacc acgtaccaga tggatgtgaa ccccgagggc     60
aaatacagct tggtgccac ctgc                                           84

<210> SEQ ID NO 56
<211> LENGTH: 28
<212> TYPE: PRT
<213> ORGANISM: Artificial sequence
<220> FEATURE:
<223> OTHER INFORMATION: ErbB2 peptide #3
```

-continued

```
<400> SEQUENCE: 56

Cys Pro Pro Leu Met Leu Tyr Asn Pro Thr Thr Tyr Gln Met Asp Val
1               5                   10                  15

Asn Pro Glu Gly Lys Tyr Ser Phe Gly Ala Thr Cys
            20                  25

<210> SEQ ID NO 57
<211> LENGTH: 108
<212> TYPE: DNA
<213> ORGANISM: Artificial sequence
<220> FEATURE:
<223> OTHER INFORMATION: ErbB2 peptide #4

<400> SEQUENCE: 57
tgtgcccact acattgacgg cccccactgc gtgaagacct gcccggcagg agtcatgggt    60
gaaaacaaca ccctggtctg aagtacgca acgccggcc atgtgtgc                 108

<210> SEQ ID NO 58
<211> LENGTH: 36
<212> TYPE: PRT
<213> ORGANISM: Artificial sequence
<220> FEATURE:
<223> OTHER INFORMATION: ErbB2 peptide #4

<400> SEQUENCE: 58

Cys Ala His Tyr Ile Asp Gly Pro His Cys Val Lys Thr Cys Pro Ala
1               5                   10                  15

Gly Val Met Gly Glu Asn Asn Thr Leu Val Trp Lys Tyr Ala Asp Ala
            20                  25                  30

Gly His Val Cys
        35

<210> SEQ ID NO 59
<211> LENGTH: 30
<212> TYPE: DNA
<213> ORGANISM: Artificial sequence
<220> FEATURE:
<223> OTHER INFORMATION: ErbB2 peptide #5

<400> SEQUENCE: 59
tgtgcccact acattgacgg cccccactgc                                    30

<210> SEQ ID NO 60
<211> LENGTH: 10
<212> TYPE: PRT
<213> ORGANISM: Artificial sequence
<220> FEATURE:
<223> OTHER INFORMATION: ErbB2 peptide #5

<400> SEQUENCE: 60

Cys Ala His Tyr Ile Asp Gly Pro His Cys
1               5                   10

<210> SEQ ID NO 61
<211> LENGTH: 69
<212> TYPE: DNA
<213> ORGANISM: Artificial sequence
<220> FEATURE:
<223> OTHER INFORMATION: ErbB2 peptide #6

<400> SEQUENCE: 61
tgcccggcag gagtcatggg agaaaataac accctagtct ggaagtacgc agacgccggc    60
catgtgtgc                                                          69
```

<210> SEQ ID NO 62
<211> LENGTH: 23
<212> TYPE: PRT
<213> ORGANISM: Artificial sequence
<220> FEATURE:
<223> OTHER INFORMATION: ErbB2 peptide #6

<400> SEQUENCE: 62

Cys Pro Ala Gly Val Met Gly Glu Asn Asn Thr Leu Val Trp Lys Tyr
1               5                   10                  15

Ala Asp Ala Gly His Val Cys
            20

<210> SEQ ID NO 63
<211> LENGTH: 9584
<212> TYPE: DNA
<213> ORGANISM: Artificial Sequence
<220> FEATURE:
<223> OTHER INFORMATION: Peptide grafting vector

<400> SEQUENCE: 63

| | | | |
|---|---|---|---|
| ctaaattgta agcgttaata ttttgttaaa attcgcgtta aatttttgtt aaatcagctc | 60 |
| attttttaac caataggccg aaatcggcaa atcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa aggggggatgt | 240 |
| gctgcaaggc gattaagttg ggtaacgcca gggttttccc agtcacgacg ttgtaaaacg | 300 |
| acggccagtg agcgcgacgt aatacgactc actatagggc gaattggcgg aaggccgtca | 360 |
| aggcctaggc gcgcctgaat aacttcgtat agcatacatt atagcaattt atcgaaaaag | 420 |
| cctgaactca ccgcgacatc cgtggagaaa ttcctcatcg aaaaattcga ctccgtgtcc | 480 |
| gatctcatgc agctgtccga gggcgaggag agtagagcat tctcattcga gtgggcggg | 540 |
| agaggctacg tgctgagagt gaactcttgt gccgacggct tctacaagga ccgatacgtc | 600 |
| taccggcatt ttgcttccgc cgctctgcct attccagaag tcctggacat tggggagttt | 660 |
| agcgagtccc tcacttactg tattagccgg cgagcccagg gagtgacact ccaggatctg | 720 |
| cctgaaactg aactgcctgc tgtgctccag cctgtcgctg aggcaatgga tgctattgct | 780 |
| gctgccgatc tgagtcagac tagcggattc ggcccatttg acccccaggg cattggccag | 840 |
| tacacaacat ggcgagactt catctgtgct atcgccgatc ctcacgtgta ccattggcag | 900 |
| actgtgatgg acgatactgt gtctgcttct gtggcacagg cactcgacga actcatgctg | 960 |
| tgggctgagg actgtcctga agtgagacat ctggtccatg ccgattttgg ctccaacaat | 1020 |
| gtgctcaccg ataacgggag aatcactgcc gtgatcgact ggagcgaggc aatgtttggc | 1080 |
| gattcccagt acgaagtggc caacatcttc ttttggcggc cttggctggc ttgtatggaa | 1140 |
| cagcagaccc ggtactttga acggcgccac cctgagctgg ctgggagtcc tagactgaga | 1200 |
| gcctacatgc tccgaattgg cctggatcag ctctaccagt cactggtgga tggcaatttc | 1260 |
| gacgatgctg cttgggcaca ggggcgctgt gatgctattg tccgatccgg cgctggaact | 1320 |
| gtggggagaa cacagatcgc taggagatcc gctgctgtct ggaccgatgg atgtgtggaa | 1380 |
| gtgctggccg atagtggaaa ccggaggcct tcaacccgac ccgggcaaa ggagtaatga | 1440 |
| ccgtttaaac ccgctgatca gcctcgactg tgccttctag ttgccagcca tctgttgttt | 1500 |
| gcccctcccc cgtgccttcc ttgaccctgg aaggtgccac tcccactgtc ctttcctaat | 1560 |

```
aaaatgagga aattgcatcg cattgtctga gtaggtgtca ttctattctg gggggtgggg    1620
tggggcagga cagcaagggg gaggattggg aagacaatag caggcatgct ggggatgcgg    1680
tgggctctat ggggatcccg cgttgacatt gattattgac tagttattaa tagtaatcaa    1740
ttacggggtc attagttcat agcccatata tggagttccg cgttacataa cttacggtaa    1800
atggcccgcc tggctgaccg cccaacgacc cccgcccatt gacgtcaata atgacgtatg    1860
ttcccatagt aacgccaata gggactttcc attgacgtca atgggtggag tatttacggt    1920
aaactgccca cttggcagta catcaagtgt atcatatgcc aagtacgccc cctattgacg    1980
tcaatgacgg taaatggccc gcctggcatt atgcccagta catgacctta tgggactttc    2040
ctacttggca gtacatctac gtattagtca tcgctattac catggtgatg cggttttggc    2100
agtacatcaa tgggcgtgga tagcggtttg actcacgggg atttccaagt ctccacccca    2160
ttgacgtcaa tgggagtttg ttttggcacc aaaatcaacg ggactttcca aaatgtcgta    2220
acaactccgc cccattgacg caaatgggcg gtaggcgtgt acggtgggag gtctatataa    2280
gcagagctct ctggctaact agagaaccca ctgcttactg ctcgacgatc tgatcaagag    2340
acaggataag gagccgccac catggagttt ggctgagct ggcttttct tgtggctatt    2400 ttaaaaggtg tccagtgttc cgatgtgccc agggacctgg aagtggtggc cgccacacct    2460
accagcctgc tgatctcttg ggatgcccct gccgtgaccg tgcggtacta cagaatcacc    2520
tacggcgaga caggcggcaa cagccccgtg caggagttta cagtgcccgg cagcaagagc    2580
accgccacca tctctggact gaagcccggc gtggactaca ccatcaccgt gtacgccgtg    2640
acaggcagag gcgatagcca cagtggtagt actccactgt ctgggtgtac aaaaacctcc    2700
ctgcacgcct ctctaacctc acaattctgt ggcggccgcg ccgccaccat gattgaacaa    2760 gatgattgc acgcaggttc tccggccgct tgggtggaga ggctattcgg ctatgactgg    2820
gcacaacaga caatcggctg ctctgatgcc gccgtgttcc ggctgtcagc gcaggggcgc    2880
ccggttcttt ttgtcaagac cgacctgtcc ggtgccctga tgaactgca ggacgaggca    2940 gcgcggctat cgtggctggc cacgacgggc gttccttgcg cagctgtgct cgacgttgtc    3000
actgaagcgg gaagggactg gctgctattg ggcgaagtgc cggggcagga tctcctgtca    3060
tctcaccttg ctcctgccga gaaagtatcc atcatggctg atgcaatgcg gcggctgcat    3120
acgcttgatc cggctacctg cccattcgac caccaagcga acatcgcat cgagcgagca    3180 cgtactcgga tggaagccgg tcttgtcgat caggtgagta caggaggtgg agagtacgcg    3240
taacacttaa gcgtctctcc aagatccttt ttaacccatc acatatacct gccgttcact    3300
attatttagt gaaatgagat attatgatat tttctgaatt gtgattaaaa aggcaacttt    3360
atgcccatgc aacagaaact ataaaaaata cagagaatga aaagaaacag atagatttt    3420 tagttcttta ggcccgtagt ctgcaaatcc ttttatgatt ttctatcaaa caaaagagga    3480
aaatagacca gttgcaatcc aaacgagagt ctaatagaat gaggtcgaaa agtaaatcgc    3540
gcgggtttgt tactgataaa gcaggcaaga cctaaaatgt gtaaagggca aagtgtatac    3600
tttggcgtca ccccttacat atttaggtc tttttttatt gtgcgtaact aacttgccat    3660
cttcaaacag gagggctgga agaagcagac cgctaacaca gtacataaaa aaggagacat    3720
gaacgatgaa catcaaaaag tttgcaaaac aagcaacagt attaacctt actaccgcac    3780 tgctggcagg aggcgcaact caagcgtttg cgaaagaaac gaaccaaaag ccatataagg    3840
aaacatacgg catttcccat attacacgcc atgatatgct gcaaatccct gaacagcaaa    3900
aaaatgaaaa atatcaagtt cctgagttcg attcgtccac aattaaaaat atctcttctg    3960
```

```
caaaaggcct ggacgtttgg gacagctggc cattacaaaa cgctgacggc actgtcgcaa      4020
actatcacgg ctaccacatc gtctttgcat tagccggaga tcctaaaaat gcggatgaca      4080
catcgattta catgttctat caaaaagtcg gcgaaacttc tattgacagc tggaaaaacg      4140
ctggccgcgt ctttaaagac agcgacaaat tcgatgcaaa tgattctatc ctaaaagacc      4200
aaacacaaga atggtcaggt tcagccacat ttacatctga cggaaaaatc cgtttattct      4260
acactgattt ctccggtaaa cattacggca aacaaacact gacaactgca caagttaacg      4320
tatcagcatc agacagctct ttgaacatca acggtgtaga ggattataaa tcaatctttg      4380
acggtgacgg aaaaacgtat caaaatgtac agcagttcat cgatgaaggc aactacagct      4440
caggcgacaa ccatacgctg agagatcctc actacgtaga agataaaggc cacaaatact      4500
tagtatttga agcaaacact ggaactgaag atggctacca aggcgaagaa tctttattta      4560
acaaagcata ctatggcaaa agcacatcat tcttccgtca agaaagtcaa aaacttctgc      4620
aaagcgataa aaaacgcacg gctgagttag caaacggcgc tctcggtatg attgagctaa      4680
acgatgatta cacactgaaa aaagtgatga accgctgat tgcatctaac acagtaacag      4740
atgaaattga acgcgcgaac gtcttttaaaa tgaacggcaa atggtatctg ttcactgact      4800
cccgcggatc aaaaatgacg attgacggca ttacgtctaa cgatatttac atgcttggtt      4860
atgtttctaa ttcttttaact ggcccataca agccgctgaa caaaactggc cttgtgttaa      4920
aaatggatct tgatcctaac gatgtaacct ttacttactc acacttcgct gtacctcaag      4980
cgaaaggaaa caatgtcgtg attacaagct atatgacaaa cagaggattc tacgcagaca      5040
aacaatcaac gtttgcgcct agcttcctgc tgaacatcaa aggcaagaaa acatctgttg      5100
tcaaagacag catccttgaa caaggacaat taacagttaa caaataaaaa cgcaaaagaa      5160
aatgccgatt atggtgcact ctcagtacaa tctgggtaag agacgtccgg aggccagccc      5220
ttctcatgtt cagagaacat ggttaactgg ttaagtcatg tcgtcccaca ggatgatctg      5280
gacgaagagc atcaggggct cgcgccagcc gaactgttcg ccaggctcaa ggcgcgcatg      5340
cccgacggcg aggatctcgt cgtgacccat ggcgatgcct gcttgccgaa tatcatggtg      5400
gaaaatggcc gcttttctgg attcatcgac tgtggccggc tgggtgtggc ggaccgctat      5460
caggacatag cgttggctac ccgtgatatt gctgaagagc ttggcggcga atgggctgac      5520
cgcttcctcg tgctttacgg tatcgccgct cccgattcgc agcgcatcgc cttctatcgc      5580
cttcttgacg agttcttctg agtcgactgc aggagtccca ctgcaccccc ctcccagtct      5640
tctctgtcca ggcaccaggc caggtatctg ggtgtgcag ccggcctggg tctggcctga      5700
ggccacaagc ccgggggtct gtgtggctgg ggacagggac gccggctgcc tctgctctgt      5760
gcttgggcca tgtgacccat tcgagtgtcc tgcacgggca caggttttg tacacccaga      5820 cagtggagta ctaccactgt gcctgccagc agcaagccca tcagcatcaa ctaccggacc      5880
ggtaccgagc ccaaatcttg tgacaaaact cacacatgcc caccgtgccc agcacctgaa      5940
ctcctggggg gaccgtcagt cttcctcttc cccccaaaac ccaaggacac cctcatgatc      6000
tctagaaccc ctgaggtcac atgcgtggtg gtggacgtga gccacgaaga ccctgaggtc      6060
aagttcaact ggtacgtgga cggcgtggag gtgcataatg ccaagacaaa gccgcgggag      6120
gagcagtaca acagcacgta ccgtgtggtc agcgtcctca ccgtcctgca ccaggactgg      6180
ctgaatggca aggagtacaa gtgcaaggtg tccaacaaag ccctcccagc ccccatcgag      6240
aaaaccatct ccaaagccaa agggcagccc cgagaaccac aggtgtacac cctgccccca      6300
```

-continued

```
tcccgggatg agctgaccaa gaaccaggtc agcctgacct gcctggtcaa aggcttctat    6360
cccagcgaca tcgccgtgga gtgggagagc aatgggcagc cggagaacaa ctacaagacc    6420
acgcctcccg tgctggactc cgacggctcc ttcttcctct acagcaagct caccgtggac    6480
aagtctagat ggcagcaggg gaacgtcttc tcatgctccg tgatgcatga ggctctgcac    6540
aaccactaca cgcagaagag cctctccctg tctccgggca aactggctct cattgtcctg    6600
ggcggcgtgg ctggcctgct gctgtttatt gggctgggca tcttcttttg tgtccggtgt    6660
cggcatagga ggcgccaagg aggtggcgga tctggagggg gaggatctgg aggggctca    6720 ggatcagggg gaggatctgg aggcggatca actgagtaca acccactgt gaggctcgct    6780 actagagatg atgtgcctag agctgtccga actctggctg ctgccttcgc cgattaccct    6840
gccactcgcc ataccgtcga tcccgatcgc acattgaac gagtcaccga actccaggag    6900
ctgtttctca ctagagtcgg gctggatatt ggcaaagtct gggtggccga tgacggagcc    6960
gctgtcgctg tgtggactac acctgagtct gtggaggctg gcgccgtgtt tgctgaaatt    7020
ggacctcgga tggctgaact gtctggatct cgactggctg cccagcagca gatggaggga    7080
ctgctggcac cccatagacc aaaggaacct gcctggtttc tggcaactgt gggagtgtca    7140
cccgatcatc agggcaaagg actgggatct gccgtggtgc tccctggcgt ggaggccgct    7200
gaacgagctg gcgtccccgc ttttctcgaa acttctgccc cccgaaatct cccttttctac    7260 gaacgactgg gattcactgt caccgccgat gtcgaagtgc tgaggggcc tagaacatgg    7320 tgtatgaccc ggaaacccgg agcttaaccg tttaaaccccg ctgatcagcc tcgactgtgc    7380
cttctagttg ccagccatct gttgtttgcc cctcccccgt gccttccttg accctggaag    7440
gtgccactcc cactgtcctt tcctaataaa atgaggaaat tgcatcgcat tgtctgagta    7500
ggtgtcattc tattctgggg ggtggggtgg ggcaggacag caaggggag gattgggaag    7560 acaatagcag gcatgctggg gatgcggtgg gctctatggc tcgagttaat taactggcct    7620
catgggcctt ccgctcactg cccgctttcc agtcggaaa cctgtcgtgc cagctgcatt    7680
aacatggtca tagctgtttc cttgcgtatt gggcgctctc cgcttcctcg ctcactgact    7740
cgctgcgctc ggtcgttcgg gtaaagcctg ggtgcctaa tgagcaaaag gccagcaaaa    7800
ggccaggaac cgtaaaaagg ccgcgttgct ggcgtttttc cataggctcc gccccctga    7860 cgagcatcac aaaaatcgac gctcaagtca gaggtggcga acccgacag gactataaag    7920 ataccaggcg tttccccctg gaagctccct cgtgcgctct cctgttccga ccctgccgct    7980
taccggatac ctgtccgcct ttctcccttc gggaagcgtg gcgctttctc atagctcacg    8040
ctgtaggtat ctcagttcgg tgtaggtcgt tcgctccaag ctgggctgtg tgcacgaacc    8100
ccccgttcag cccgaccgct gcgccttatc cggtaactat cgtcttgagt ccaacccggt    8160
aagacacgac ttatcgccac tggcagcagc cactggtaac aggattagca gagcgaggta    8220
tgtaggcggt gctacagagt tcttgaagtg gtggcctaac tacggctaca ctagaagaac    8280
agtatttggt atctgcgctc tgctgaagcc agttaccttc ggaaaaagag ttggtagctc    8340
ttgatccggc aaacaaacca ccgctggtag cggtggtttt tttgtttgca agcagcagat    8400
tacgcgcaga aaaaaggat ctcaagaaga tcctttgatc ttttctacgg ggtctgacgc    8460
tcagtggaac gaaaactcac gttaagggat tttggtcatg agattatcaa aaaggatctt    8520
cacctagatc cttttaaatt aaaaatgaag ttttaaatca atctaaagta tatatgagta    8580
aacttggtct gacagttacc aatgcttaat cagtgaggca cctatctcag cgatctgtct    8640
atttcgttca tccatagttg cctgactccc cgtcgtgtag ataactacga tacgggaggg    8700
```

```
cttaccatct ggccccagtg ctgcaatgat accgcgagaa ccacgctcac cggctccaga    8760
tttatcagca ataaaccagc cagccggaag ggccgagcgc agaagtggtc ctgcaacttt    8820
atccgcctcc atccagtcta ttaattgttg ccgggaagct agagtaagta gttcgccagt    8880
taatagtttg cgcaacgttg ttgccattgc tacaggcatc gtggtgtcac gctcgtcgtt    8940
tggtatggct tcattcagct ccggttccca acgatcaagg cgagttacat gatccccat    9000 gttgtgcaaa aaagcggtta gctccttcgg tcctccgatc gttgtcagaa gtaagttggc    9060
cgcagtgtta tcactcatgg ttatggcagc actgcataat tctcttactg tcatgccatc    9120
cgtaagatgc ttttctgtga ctggtgagta ctcaaccaag tcattctgag aatagtgtat    9180
gcggcgaccg agttgctctt gcccggcgtc aatacgggat aataccgcgc cacatagcag    9240
aactttaaaa gtgctcatca ttggaaaacg ttcttcgggg cgaaaactct caaggatctt    9300
accgctgttg agatccagtt cgatgtaacc cactcgtgca cccaactgat cttcagcatc    9360
ttttactttc accagcgttt ctgggtgagc aaaaacagga aggcaaaatg ccgcaaaaaa    9420
gggaataagg gcgacacgga aatgttgaat actcatactc ttcctttttc aatattattg    9480
aagcatttat cagggttatt gtctcatgag cggatacata tttgaatgta tttagaaaaa    9540
taaacaaata ggggttccgc gcacatttcc ccgaaaagtg ccac                     9584
```

<210> SEQ ID NO 64
<211> LENGTH: 1694
<212> TYPE: DNA
<213> ORGANISM: Artificial sequence
<220> FEATURE:
<223> OTHER INFORMATION: Ig kappa cassette

<400> SEQUENCE: 64

```
aattcttctg tctgtcccta acatgccctg tgattatccg caaacaacac acccaagggc      60
agaactttgt tacttaaaca ccatcctgtt tgcttctttc ctcaggaact gtggctgcac     120
catctgtctt catcttcccg ccatctgatg agcagttgaa aagcggaaca gccagcgttg     180
tgtgcctgct gaataacttc tatcccagag aggccaaagt acagtggaag gtggataacg     240
ccctccaatc gggtaactcc caggagagtg tcacagagca ggacagcaag gacagcacct     300
acagcctcag cagcaccctg acgctgagca agcagacta cgagaaacac aaagtctacg     360
cctgcgaagt cacccatcag ggcctgagca gccccgtcac aaagagcttc aacagggag     420 agtgtggcgg cggcagctcc cggcaccgcc gagccctggg cggcggcagc gacgtcccgt     480
caaatattgc aaaaattatc atcggccccc tcatctttgt ctttctcttc tccgttgtga     540
ttggaagtat ttatctattc ctgagaaaga ggcagccaga tgggccgctg ggaccgcttt     600
acgcttctgg aagcgctatt gaacaagatg gattgcacgc aggttctccg gccgcttggg     660
tggagaggct attcggctat gactgggcac aacagacaat cggctgctct gatgccgccg     720 tgttccggc gtcagcgcag gggcgcccgg ttcttttgt caagaccgac ctgtccggtg     780
ccctgaatga actgcaggac gaggcagcgc ggctatcgtg gctggccacg acgggcgttc     840
cttgcgcagc tgtgctcgac gttgtcactg aagcgggaag ggactggctg ctattgggcg     900
aagtgccggg gcaggatctc ctgtcatctc accttgctcc tgccgagaaa gtatccatca     960
tggctgatgc aatgcggcgg ctgcatacgc ttgatccggc tacctgccca ttcgaccacc    1020
aagcgaaaca tcgcatcgag cgagcacgta ctcggatgga agccggtctt gtcgatcagg    1080
atgatctgga cgaagagcat caggggctcg cgccagccga actgttcgcc aggctcaagg    1140
```

```
cgcgcatgcc cgacggcgat gatctcgtcg tgacccatgg cgatgcctgc ttgccgaata    1200
tcatggtgga aaatggccgc ttttctggat tcatcgactg tggccggctg ggtgtggcgg    1260
accgctatca ggacatagcg ttggctaccc gtgatattgc tgaagagctt ggcggcgaat    1320
gggctgaccg cttcctcgtg ctttacggta tcgccgctcc cgattcgcag cgcatcgcct    1380
tctatcgcct tcttgacgag ttcttctgat ctagagggcc cgtttaaacc cgctgatcag    1440
cctcgactgt gccttctagt tgccagccat ctgttgtttg cccctccccc gtgccttcct    1500
tgaccctgga aggtgccact cccactgtcc tttcctaata aaatgaggaa attgcatcgc    1560
attgtctgag taggtgtcat tctattctgg ggggtgggt ggggcaggac agcaaggggg     1620
aggattggga agacaatagc aggcatgctg gggatgcggt gggctctatg cttctgagg     1680 cggctgcagt tatg                                                      1694
```

```
<210> SEQ ID NO 65
<211> LENGTH: 42
<212> TYPE: DNA
<213> ORGANISM: Artificial sequence
<220> FEATURE:
<223> OTHER INFORMATION: Anti-TPO peptide

<400> SEQUENCE: 65
atcgagggcc ctaccctgag acagtggctg gccgctagag ct                        42
```

```
<210> SEQ ID NO 66
<211> LENGTH: 93
<212> TYPE: DNA
<213> ORGANISM: Artificial sequence
<220> FEATURE:
<223> OTHER INFORMATION: Anti-GLP1 receptor peptide

<400> SEQUENCE: 66
catgccgagg gcacctttac ctccgacgtg tcctcatatc tggaaggcca agccgccaaa    60
gagtttatcg cctggctagt aaaaggaagg ggc                                  93
```

```
<210> SEQ ID NO 67
<211> LENGTH: 63
<212> TYPE: DNA
<213> ORGANISM: Artificial sequence
<220> FEATURE:
<223> OTHER INFORMATION: Anti-GLP1 receptor peptide

<400> SEQUENCE: 67
acctccgacg tgtcctcata tctggaaggc caagccgcca agagtttat cgcctggcta    60 gta                                                                   63
```

```
<210> SEQ ID NO 68
<211> LENGTH: 117
<212> TYPE: DNA
<213> ORGANISM: Artificial sequence
<220> FEATURE:
<223> OTHER INFORMATION: Anti-GLP1 receptor exendin-4 peptide

<400> SEQUENCE: 68
catggcgagg gcaccttcac ctccgacctg tccaaacaaa tggaagaaga agccgtccgg    60
ctgttcatcg aatggctgaa aaatggcggc ccttcctctg gcgcccctcc tccttct      117
```

```
<210> SEQ ID NO 69
<211> LENGTH: 93
<212> TYPE: DNA
<213> ORGANISM: Artificial sequence
```

```
<220> FEATURE:
<223> OTHER INFORMATION: Anti-GLP1 receptor exendin-4 peptide

<400> SEQUENCE: 69
gacctgtcca aacaaatgga agaagaagcc gtccggctgt tcatcgaatg gctgaaaaat    60
ggcggccctt cctctggcgc ccctcctcct tct                                 93

<210> SEQ ID NO 70
<211> LENGTH: 39
<212> TYPE: DNA
<213> ORGANISM: Artificial sequence
<220> FEATURE:
<223> OTHER INFORMATION: Anti-GLP1 receptor exendin-4 peptide

<400> SEQUENCE: 70
gaagaagaag ccgtccggct gttcatcgaa tggctgaaa                           39

<210> SEQ ID NO 71
<211> LENGTH: 14
<212> TYPE: PRT
<213> ORGANISM: Artificial sequence
<220> FEATURE:
<223> OTHER INFORMATION: Anti-TPO receptor peptide

<400> SEQUENCE: 71

Ile Glu Gly Pro Thr Leu Arg Gln Trp Leu Ala Ala Arg Ala
1               5                   10

<210> SEQ ID NO 72
<211> LENGTH: 53
<212> TYPE: PRT
<213> ORGANISM: Artificial Sequence
<220> FEATURE:
<223> OTHER INFORMATION: Anti-GLP-1 Receptor Exendin-4 Peptides

<400> SEQUENCE: 72

Ala Arg Arg Ala Ser Ser Val His Gly Glu Gly Thr Phe Thr Ser Asp
1               5                   10                  15

Leu Ser Lys Gln Met Glu Glu Glu Ala Val Arg Leu Phe Ile Glu Trp
            20                  25                  30

Leu Lys Asn Gly Gly Pro Ser Ser Gly Ala Pro Pro Pro Ser Asp Gly
        35                  40                  45

Ser Trp Phe Asp Pro
    50

<210> SEQ ID NO 73
<211> LENGTH: 48
<212> TYPE: PRT
<213> ORGANISM: Artificial Sequence
<220> FEATURE:
<223> OTHER INFORMATION: Anti-GLP-1 Receptor Exendin-4 Peptides

<400> SEQUENCE: 73

Ala Ser Thr His Gly Glu Gly Thr Phe Thr Ser Asp Leu Ser Lys Gln
1               5                   10                  15

Met Glu Glu Glu Ala Val Arg Leu Phe Ile Glu Trp Leu Lys Asn Gly
            20                  25                  30

Gly Pro Ser Ser Gly Ala Pro Pro Pro Ser Asp Trp Tyr Phe Asp Leu
        35                  40                  45

<210> SEQ ID NO 74
<211> LENGTH: 48
<212> TYPE: PRT
```

```
<213> ORGANISM: Artificial Sequence
<220> FEATURE:
<223> OTHER INFORMATION: Anti-GLP-1 Receptor Exendin-4 Peptides

<400> SEQUENCE: 74

Ala His Gly Glu Gly Thr Phe Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser Ser Met Leu Asp Ala Phe Asp Ile
        35                  40                  45

<210> SEQ ID NO 75
<211> LENGTH: 49
<212> TYPE: PRT
<213> ORGANISM: Artificial Sequence
<220> FEATURE:
<223> OTHER INFORMATION: Anti-GLP-1 Receptor Exendin-4 Peptides

<400> SEQUENCE: 75

Ala Arg Glu Leu His Gly Glu Gly Thr Phe Thr Ser Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Pro Pro Ser Asp Asp Ala Phe Asp
        35                  40                  45

Ile

<210> SEQ ID NO 76
<211> LENGTH: 50
<212> TYPE: PRT
<213> ORGANISM: Artificial Sequence
<220> FEATURE:
<223> OTHER INFORMATION: Anti-GLP-1 Receptor Exendin-4 Peptides

<400> SEQUENCE: 76

Thr Ser Phe His Gly Glu Gly Thr Phe Thr Ser Asp Leu Ser Lys Gln
1               5                   10                  15

Met Glu Glu Glu Ala Val Arg Leu Phe Ile Glu Trp Leu Lys Asn Gly
            20                  25                  30

Gly Pro Ser Ser Gly Ala Pro Pro Pro Ser Gln Thr Leu Glu Tyr Phe
        35                  40                  45

Gln His
    50

<210> SEQ ID NO 77
<211> LENGTH: 52
<212> TYPE: PRT
<213> ORGANISM: Artificial Sequence
<220> FEATURE:
<223> OTHER INFORMATION: Anti-GLP-1 Receptor Exendin-4 Peptides

<400> SEQUENCE: 77

Ala Arg Asp Gly His Gly Glu Gly Thr Phe Thr Ser Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Pro Pro Ser Trp Trp Pro Pro Asp
        35                  40                  45

Ala Phe Asp Ile
    50
```

<210> SEQ ID NO 78
<211> LENGTH: 48
<212> TYPE: PRT
<213> ORGANISM: Artificial Sequence
<220> FEATURE:
<223> OTHER INFORMATION: Anti-GLP-1 Receptor Exendin-4 Peptides

<400> SEQUENCE: 78

Ala Thr Asp Gly Glu Gly Thr Phe Thr Ser Asp Leu Ser Lys Gln Met
1               5                   10                  15

Glu Glu Glu Ala Val Arg Leu Phe Ile Glu Trp Leu Lys Asn Gly Gly
            20                  25                  30

Pro Ser Ser Gly Ala Pro Pro Ser Met Tyr Asp Ala Phe Asp Ile
        35                  40                  45

<210> SEQ ID NO 79
<211> LENGTH: 50
<212> TYPE: PRT
<213> ORGANISM: Artificial Sequence
<220> FEATURE:
<223> OTHER INFORMATION: Anti-GLP-1 Receptor Exendin-4 Peptides

<400> SEQUENCE: 79

Ala Arg Leu His Gly Glu Gly Thr Phe Thr Ser Asp Leu Ser Lys Gln
1               5                   10                  15

Met Glu Glu Glu Ala Val Arg Leu Phe Ile Glu Trp Leu Lys Asn Gly
            20                  25                  30

Gly Pro Ser Ser Gly Ala Pro Pro Ser Leu Ala Asn Asn Trp Phe
        35                  40                  45

Asp Pro
    50

<210> SEQ ID NO 80
<211> LENGTH: 40
<212> TYPE: PRT
<213> ORGANISM: Artificial Sequence
<220> FEATURE:
<223> OTHER INFORMATION: Anti-GLP-1 Receptor Exendin-4 Peptides

<400> SEQUENCE: 80

Ala Arg Asp His Leu Ser Lys Gln Met Glu Glu Glu Ala Val Arg Leu
1               5                   10                  15

Phe Ile Glu Trp Leu Lys Asn Gly Gly Pro Ser Ser Gly Ala Pro Pro
            20                  25                  30

Pro Ser Tyr Trp Tyr Phe Asp Leu
        35                  40

<210> SEQ ID NO 81
<211> LENGTH: 400
<212> TYPE: DNA
<213> ORGANISM: Artificial sequences
<220> FEATURE:
<223> OTHER INFORMATION: Anti-TPO receptor peptide plus flanking
      sequences

<400> SEQUENCE: 81
caggtgcagc tggtgcagtc tggcgccgaa gtgaagaaac ccggcagcag cgtgaaggtg      60
tcctgcaagg ccagcggcgg caccttcagc agctacgcca tcagctgggt ccgccaggct     120
cctggacagg gactggaatg gatgggcggc atcatcccca tcttcggcac cgccaactac     180
gcccagaaat tccagggcag agtgaccatc accgccgacg agagcaccag caccgcctac     240

-continued

```
atggaactga gcagccttcg aagcgaggac accgctgtgt attactgtgc ggggcctctg    300
cggatcgagg gccctaccct gagacagtgg ctggccgcta gcttccct atactacatg     360 gacgtctggg gcaaagggac cacggtcacc gtgtcctcag                          400
```

<210> SEQ ID NO 82
<211> LENGTH: 418
<212> TYPE: DNA
<213> ORGANISM: Artificial sequences
<220> FEATURE:
<223> OTHER INFORMATION: Anti-TPO receptor peptide plus flanking sequences

<400> SEQUENCE: 82

```
caggtgcagc tggtgcagtc tggcgccgaa gtgaagaaac ccggcagcag cgtgaaggtg     60
tcctgcaagg ccagcggcgg caccttcagc agctacgcca tcagctgggt ccgccaggct    120
cctggacagg gactggaatg gatgggcggc atcatcccca tcttcggcac cgccaactac    180
gcccagaaat tccagggcag agtgaccatc accgccgacg agagcaccag caccgcctac    240
atggaactga gcagccttcg aagcgaggac accgctgtgt attactgtgc gagagcaaag    300
agtagtcaga tcgagggccc taccctgaga cagtggctgg ccgctagagc tgagctgagg    360
ctgcaacact actacatgga cgtctggggc aaagggacca cggtcaccgt gtcctcag     418
```

<210> SEQ ID NO 83
<211> LENGTH: 406
<212> TYPE: DNA
<213> ORGANISM: Artificial sequences
<220> FEATURE:
<223> OTHER INFORMATION: Anti-TPO receptor peptide plus flanking sequences

<400> SEQUENCE: 83

```
caggtgcagc tggtgcagtc tggcgccgaa gtgaagaaac ccggcagcag cgtgaaggtg     60
tcctgcaagg ccagcggcgg caccttcagc agctacgcca tcagctgggt ccgccaggct    120
cctggacagg gactggaatg gatgggcggc atcatcccca tcttcggcac cgccaaatac    180
gcccagaaat tccagggcag agtgaccatc accgccgacg agagcaccag caccgcctac    240
atggaactga gcagccttcg aagcgaggac accgctgtgt attactgtgc gaggaagccg    300
caggctatcg agggccctac cctgagacag tggctggccg ctagagctct gggaaactac    360
tacatggacg tctggggcaa agggaccacg gtcaccgtgt cctcag                   406
```

<210> SEQ ID NO 84
<211> LENGTH: 412
<212> TYPE: DNA
<213> ORGANISM: Artificial sequences
<220> FEATURE:
<223> OTHER INFORMATION: Anti-TPO receptor peptide plus flanking sequences

<400> SEQUENCE: 84

```
caggtgcagc tggtgcagtc tggcgccgaa gtgaagaaac ccggcagcag cgtgaaggtg     60
tcctgcaagg ccagcggcgg caccttcagc agctacgcca tcagctgggt ccgccaggct    120
cctggacagg gactggaatg gatgggcggc atcatcccca tcttcggcac cgccaactac    180
gcccagaaat tccagggcag agtgaccatc accgccgacg agagcaccag caccgcctac    240
atggaactga gcagccttcg aagcgaggac accgctgtgt attactgtgc gagaacgttg    300
cgtatcgagg gccctaccct gagacagtgg ctggccgcta gctccggc ggcctactac     360
```
tactactaca tggacgtctg gggcaaaggg accacggtca ccgtgtcctc ag        412

<210> SEQ ID NO 85
<211> LENGTH: 415
<212> TYPE: DNA
<213> ORGANISM: Artificial sequences
<220> FEATURE:
<223> OTHER INFORMATION: Anti-TPO receptor peptide plus flanking
      sequences

<400> SEQUENCE: 85
caggtgcagc tggtgcagtc tggcgccgaa gtgaagaaac ccggcagcag cgtgaaggtg        60
tcctgcaagg ccagcggcgg caccttcagc agctacgcca tcagctgggt ccgccaggct       120
cctggacagg gactggaatg gatgggcggc atcatcccca tcttcggcac cgccaactac       180
gcccagaaat tccagggcag agtgaccatc accgccgacg agagcaccag caccgcctac       240
atggaactga gcagccttcg aagcgaggac accgctgtgt attactgtgc gagttgtagg       300
tctatcgagg gccctaccct gagacagtgg ctggccgctc gagcttgtct ggatctgatc       360
gggtactact acatggacgt ctggggcaaa gggaccacgg tcaccgtgtc ctcag            415

<210> SEQ ID NO 86
<211> LENGTH: 481
<212> TYPE: DNA
<213> ORGANISM: Artificial Sequence
<220> FEATURE:
<223> OTHER INFORMATION: Anti-GLP-1 Receptor Exendin-4 Peptides

<400> SEQUENCE: 86
caggtgcagc tggtgcagtc tggcgccgaa gtgaagaaac ccggcagcag cgtgaaggtg        60
tcctgcaagg ccagcggcgg caccttcagc agctacgcca tcagctgggt ccgccaggct       120
cctggacagg gactggaatg gatgggcggc atcatcccca tcttcggcac cgccaactac       180
gcccagaaat tccagggcag agtgaccatc accgccgacg agagcaccag caccgcctac       240
atggaactga gcagccttcg aagcgaggac accgctgtgt attactgtgc gagacgggcc       300
tctagtgtgc atggcgaggg caccttcacc tccgacctgt ccaaacaaat ggaagaagaa       360
gccgtccggc tgttcatcga atggctgaaa aatggcggcc cttcctctgg cgcccctcct       420
ccttctgatg gaagctggtt cgaccctggg gccagggaa cctggtcac cgtgtcctca       480 g                                                                        481

<210> SEQ ID NO 87
<211> LENGTH: 466
<212> TYPE: DNA
<213> ORGANISM: Artificial Sequence
<220> FEATURE:
<223> OTHER INFORMATION: Anti-GLP-1 Receptor Exendin-4 Peptides

<400> SEQUENCE: 87
caggtgcagc tggtgcagtc tggcgccgaa gtgaagaaac ccggcagcag cgtgaaggtg        60
tcctgcaagg ccagcggcgg caccttcagc agctacgcca tcagctgggt ccgccaggct       120
cctggacagg gactggaatg gatgggcggc atcatcccca tcttcggcac cgccaactac       180
gcccagaaat tccagggcag agtgaccatc accgccgacg agagcaccag caccgcctac       240
atggaactga gcagccttcg aagcgaggac accgctgtgt attactgtgc gagtactcat       300
ggcgagggca ccttcacctc cgacctgtcc aaacaaatgg aagaagaagc cgtccggctg       360
ttcatcgaat ggctgaaaaa tggcggccct tcctctggcg cccctcctcc ttctgactgg       420
tacttcgatc tctggggccg tggcaccctg gtcactgtgt cctcag        466

<210> SEQ ID NO 88
<211> LENGTH: 466
<212> TYPE: DNA
<213> ORGANISM: Artificial Sequence
<220> FEATURE:
<223> OTHER INFORMATION: Anti-GLP-1 Receptor Exendin-4 Peptides

<400> SEQUENCE: 88
gaagtgcagc tggtggaaag cggcggaggc ctggtgcagc ctggcggcag cctgagactg        60
tcttgcgccg ccagcggctt caccttcagc agctacgcca tgcactgggt ccgccaggcc       120
cctggcaagg gactggaata cgtgtccgcc atcagctcga acggcggcag cacctactac       180
gccaacagcg tgaagggccg gttcaccatc agccgggaca cgccaagaa cagcctgtac        240
ctgcagatga acagcctgcg ggccgaggac accgccgtgt attactgtgc gcatggcgag       300
ggcaccttca cctccgacct gtccaaacaa atggaagaag aagccgtccg gctgttcatc       360
gaatggctga aaaatggcgg cccttcctct ggcgcccctc ctccttctag tatgctcgat       420
gcttttgata tctggggcca aggacaatg gtcaccgtgt cctcag                       466

<210> SEQ ID NO 89
<211> LENGTH: 469
<212> TYPE: DNA
<213> ORGANISM: Artificial Sequence
<220> FEATURE:
<223> OTHER INFORMATION: Anti-GLP-1 Receptor Exendin-4 Peptides

<400> SEQUENCE: 89
gaagtgcagc tggtggaaag cggcggaggc ctggtgcagc ctggcggcag cctgagactg        60
tcttgcgccg ccagcggctt caccttcagc agctacgcca tgcactgggt ccgccaggcc       120
cctggcaagg gactggaata cgtgtccgcc atcagctcga acggcggcag cacctactac       180
gccaacagcg tgaagggccg gttcaccatc agccgggaca cagcaagaa cacccctgtac       240
ctgcagatgg gcagcctgcg ggccgaggat atggccgtgt attactgtgc gagagagctg       300
catggcgagg gcaccttcac ctccgacctg tccaaacaaa tggaagaaga agccgtccgg       360
ctgttcatcg aatggctgaa aaatggcggc cttcctctg gcgcccctcc tccttctgat        420
gatgcttttg atatctgggg ccaagggaca atggtcaccg tgtcctcag                   469

<210> SEQ ID NO 90
<211> LENGTH: 478
<212> TYPE: DNA
<213> ORGANISM: Artificial Sequence
<220> FEATURE:
<223> OTHER INFORMATION: Anti-GLP-1 Receptor Exendin-4 Peptides

<400> SEQUENCE: 90
gaagtgcagc tggtggaaag cggcggaggc ctggtgcagc ctggcggcag cctgaaactg        60
agctgcgccg ccagcggctt cacctttagc ggcagcgcca tgcactgggt ccgccaggcc       120
tctggcaagg gactggaatg ggtcggacgg attcgaagca aggccaacag ctacgccacc       180
gcctacgccg cctccgtgaa gggccggttc accatcagcc gggacgacag caagaacacc       240
gcctacctgc agatgaacag cctgaaaacc gaggacaccg ccgtgtatta ctgtactagt       300
tttcatggcg agggcacctt cacctccgac ctgtccaaac aaatggaaga agaagccgtc       360
cggctgttca tcgaatggct gaaaaatggc ggcccttcct ctggcgcccc tcctccttct       420
cagacgctgg aatacttcca gcactggggc cagggcaccc tggtcaccgt gtcctcag    478

<210> SEQ ID NO 91
<211> LENGTH: 478
<212> TYPE: DNA
<213> ORGANISM: Artificial Sequence
<220> FEATURE:
<223> OTHER INFORMATION: Anti-GLP-1 Receptor Exendin-4 Peptides

<400> SEQUENCE: 91
caggtgcagc tggtgcagtc tggcgccgaa gtgaagaaac cggcagcag cgtgaaggtg    60 tcctgcaagg ccagcggcgg caccttcagc agctacgcca tcagctgggt ccgccaggct    120
cctggacagg gactggaatg gatgggcggc atcatcccca tcttcggcac cgccaactac    180
gcccagaaat tccagggcag agtgaccatc accgccgacg agagcaccag caccgcctac    240
atggaactga gcagccttcg aagcgaggac accgctgtgt attactgtgc gagagatggt    300
catggcgagg gcaccttcac ctccgacctg tccaaacaaa tggaagaaga agccgtccgg    360
ctgttcatcg aatggctgaa aaatggcggc ccttcctctg gcgcccctcc tccttcttgg    420
tggccacccg atgcttttga tatctggggc caagggacaa tggtcaccgt gtcctcag    478

<210> SEQ ID NO 92
<211> LENGTH: 466
<212> TYPE: DNA
<213> ORGANISM: Artificial Sequence
<220> FEATURE:
<223> OTHER INFORMATION: Anti-GLP-1 Receptor Exendin-4 Peptides

<400> SEQUENCE: 92
gaagtgcagc tggtgcagtc tggcgccgaa gtgaagaaac ctggcgccac cgtgaagatc    60
agctgcaagg tgtccggcta caccttcacc gactactaca tgcactgggt gcagcaggcc    120
cctggcaagg gactggaatg gatgggcctg gtcgatcccg aggacggcga gacaatctac    180
gccgagaagt tccagggcag agtgaccatc accgccgaca ccagcaccga caccgcctac    240
atggaactga gcagcctgcg gagcgaggac accgctgtgt attactgtgc aacagatggc    300 gagggcaccct tcacctccga cctgtccaaa caaatggaag aagaagccgt ccggctgttc    360
atcgaatggc tgaaaaatgg cggccctttcc tctggcgccc ctcctccttc tatgtatgat    420
gcttttgata tctggggcca agggacaatg gtcaccgtgt cctcag    466

<210> SEQ ID NO 93
<211> LENGTH: 472
<212> TYPE: DNA
<213> ORGANISM: Artificial Sequence
<220> FEATURE:
<223> OTHER INFORMATION: Anti-GLP-1 Receptor Exendin-4 Peptides

<400> SEQUENCE: 93
caggtgcagc tggtgcagtc tggcgccgaa gtgaagaaac cggcagcag cgtgaaggtg    60 tcctgcaagg ccagcggcgg caccttcagc agctacgcca tcagctgggt ccgccaggct    120
cctggacagg gactggaatg gatgggcggc atcatcccca tcttcggcac cgccaactac    180
gcccagaaat tccagggcag agtgaccatc accgccgacg agagcaccag caccgcctac    240
atggaactga gcagccttcg aagcgaggac accgctgtgt attactgtgc gcggcttcat    300
ggcgagggca ccttcacctc cgacctgtcc aaacaaatgg aagaagaagc cgtccggctg    360
ttcatcgaat ggctgaaaaa tggcggccct tcctctggcg ccctcctcc ttctttggcg    420 aacaactggt tcgacccctg gggccaggga accctggtca ccgtgtcctc ag    472

<210> SEQ ID NO 94
<211> LENGTH: 442
<212> TYPE: DNA
<213> ORGANISM: Artificial Sequence
<220> FEATURE:
<223> OTHER INFORMATION: Anti-GLP-1 Receptor Exendin-4 Peptides

<400> SEQUENCE: 94

```
gaagtgcagc tggtggaaag cggaggcgga gtggttcgac ctggcggaag cctgagactg      60
tcttgcgccg ccagcggctt cacctttgac gactacggca tgagctgggt ccgccaggcc     120
cctggcaagg gactggaatg ggtgtccggc atcaactgga acggcggcag caccggctac     180
gccgacagcg tgaagggccg gttcaccatc agccgggaca acgccaagaa cagcctgtac     240
ctgcagatga acagcctgcg ggccgaggac accgccttgt atcactgtgc gagagatcac     300
ctgtccaaac aaatggaaga agaagccgtc cggctgttca tcgaatggct gaaaaatggc     360
ggcccttcct ctggcgcccc tcctccttct tactggtact tcgatctctg gggccgtggc     420
accctggtca ctgtgtcctc ag                                              442
```

GENERATING TARGETED SEQUENCE DIVERSITY IN FUSION PROTEINS

CROSS-REFERENCE TO RELATED APPLICATIONS

This is the U.S. National Stage of International Application No. PCT/CA2013/050204, filed Mar. 14, 2013, which claims the benefit of U.S. Provisional Patent Application No. 61/610,797, filed Mar. 14, 2012, and also U.S. Provisional Patent Application No. 61/731,988 filed Nov. 30, 2012, the disclosures of which are hereby incorporated by reference in their entireties.

INCORPORATION OF SEQUENCE LISTING

A sequence listing contained in the file named "Sequence_listing_ST25_PCT_CA2013_050204.txt" which is 65,564 bytes (measured in MS-Windows) and comprising 94 nucleotide sequences, created on Sep. 11, 2014, is electronically filed herewith and is incorporated by reference in its entirety.

FIELD OF THE INVENTION

The present invention relates to the field of protein engineering and, in particular, to methods of generating optimized fusion proteins.

BACKGROUND OF THE INVENTION

A number of successful protein therapeutics are recombinant fusion proteins consisting of two proteins or protein domains fused together through a linker, or a protein scaffold into which one or more domains from a second protein have been grafted. Typically, such fusion proteins are designed to leverage beneficial properties of each member of the fusion.

For example, cytokines or growth factors have been fused with the Fc portion of IgG1 or immunotoxin and expressed as single polypeptides with dual biological activities. Examples of therapeutic fusion proteins that have been developed using cytokines or growth factors and the Fc portion of IgG1 include Enbrel® (TNF-RIFs-IgG1), Ontak® (IL-2/diphtheria toxin), Orencia® (CTLA-4/Fc-IgG1) and Amevive® (LFA-3/Fc-IgG1).

Protein engineering has been used extensively to introduce novel binding specificities into protein scaffolds. Both rational and combinatorial approaches have been used with a variety of structurally diverse scaffolds (see Binz et al., 2005, *Nature Biotechnology,* 23(10):1257-1268; Nygren & Skerra (2004, *J Immunol. Methods,* 290:3-28) and Gebauer & Skerra (2009, *Curr. Op. Chem. Biol.,* 13:245-255). Antibodies are perhaps the best studied of all protein scaffolds and affinity transfer by loop swapping has become routine. The technique of loop swapping was first described by Jones et al. (1986, *Nature* 321(6069):522-525), who substituted the CDRs from the heavy chain variable region of a mouse antibody, which binds to the hapten 4-hydroxy-3-nitrophenacetyl caproic acid (NP-cap), for the corresponding CDRs of a human myeloma antibody. It is now quite common to transfer the complementarity determining region (CDR) loops from a non-human antibody to the scaffold of a human antibody to increase its therapeutic potential (Jones et al., 1986, ibid; Riechmann et al., 1988, *Nature* 332(6162):323-327; Verhoeyen et al., 1988, *Science* 239(4847):1534-1536).

Affinity transfer by CDR replacement has also been successful with non-immunoglobulin scaffolds. Nicaise et al. (2004, *Protein Sci* 13(7):1882-1891) grafted the CDR3 of a lysozyme-specific camel antibody onto neocarzinostatin (NCS). Novel binding properties have also been generated by transferring CDR-like loops from proteins other than antibodies, for example, van den Beucken et al. (2001, *J Mol Biol* 310(3):591-601) made a $V_L$ library with a constant CDR3-like sequence from the protein CLTA-4, and selected variants with specificity for its receptor B7.1 and demonstrated that the flanking conformational context is important in maintaining functional binding properties of the transferred domain. Several non-antibody scaffolds are also being evaluated for use as potential therapeutics including fibronectin (Hackel et al., 2008, *J Mol Biol* 381(5):1238-1252; Lipovsek et al., 2007, *J Mol Biol* 368(4):1024-1041), lipocalins, avimers, adnectins and ankyrins. Zeytun et al. (2003, *Nat Biotechnol* 21(12):1473-1479), introduced diverse CDR-H3 sequences into four surface loops of an optimised GFP scaffold to create "fluorobodies."

Various methods have been used to introduce diversity into these scaffolds including error prone PCR approaches, degenerate oligo or peptide synthesis or a variety of DNA/CDR shuffling and CDR walking strategies (Bernath et al., 2005, *J Mol Biol* 345(5):1015-1026; Nord et al., 1997, *Nat Biotechnol* 15(8):772-777; Colas et al., 1996, *Nature* 380 (6574):548-550).

The first report of peptide being placed into the CDR of an antibody was by Sallazzo (1990). Placing peptides into a CDR of antibody and maintaining peptide function is often compromised because the peptide is no longer unconstrained or is constrained in an inappropriate confirmation. Successful insertion of RGD peptides into the CDR3 of the antibody heavy chain has been reported (Zanetti et al., 1993, *EMBO J,* 12(11):4375-4384). Simon et al. (2005, *Arch Biochem Biophys,* 440(2):148-157) describes the insertion of the somatostatin peptide into the CDRs of the kappa light chain using PCR mediated gene splicing by overlap extension. The points of insertion were identified through alignment of kappa light chain variable region amino acid sequences and X-ray crystal structures. The authors confirmed that somatostatin peptides inserted into the predicted regions of kappa CDR-1 and CDR-2 were able to bind to membranes containing somatostatin receptor 5.

A TPO agonist antibody has also been described that utilized insertion of two copies of an active peptide into CDR loops of an antibody fragment (Fab) (Frederickson et al., 2006, *PNAS USA,* 103(39):14307-14312). The group reported that the amino acids flanking the peptide required optimization for proper presentation of the peptide in the context of the antibody scaffold. Using phage display, two amino acids on either side of the peptide were randomized and inserted in to CDR3 of the heavy chain and subsequent panning identified binders. Several of the identified binders also showed agonist activity.

V(D)J recombination is the process responsible of the assembly of antibody gene segments (V, D and J; or V and J in the case of the light chain) and as part of the assembly process creates the CDR3 of the respective antibody chain. V(D)J recombination can be considered conceptually as a segment shuffler for antibodies, i.e. it brings together the different VH segments, D segments and JH segments to create an antibody (similarly V(D)J recombination at the light chain assembles different combinations of light chain V and J segments at either the kappa or lambda locus). The recombination event results in large chromosomal deletions in order to bring the required segments together. V(D)J recombination is targeted by the presence of specific DNA sequences called the recombination signal sequences (RSSs). The recombination reaction involves the recombination proteins RAG-1 and RAG-2 and follows a 12/23 rule where an RSS with a 23 bp spacer is paired only with an RSS with 12 bp spacer and adjacent sequences are subsequently joined by double-stranded break repair proteins.

U.S. Pat. No. 8,012,714 describes compositions and methods for generating sequence diversity in the CDR3 region of de novo generated immunoglobulins in vitro. The methods comprise constructing nucleic acid molecules that comprise polynucleotide sequences encoding immunoglobulin V, D, J and C regions, together with recombination signal sequences (RSS), and subsequently introducing these nucleic acid molecules into suitable recombination-competent host cells.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide methods and compositions for generating targeted sequence diversity in fusion proteins. One aspect of the invention relates to a method of generating variants of a fusion protein comprising the steps of: providing a first nucleic acid sequence comprising a first coding sequence encoding a first portion of the fusion protein and further comprising a first recombination signal sequence (RSS); providing a second nucleic acid sequence comprising a second coding sequence encoding a second portion of the fusion protein and further comprising a second RSS capable of functional recombination with the first RSS; introducing the first and second nucleic acid sequence into a recombination-competent host cell, and culturing the host cell in vitro under conditions allowing (a) recombination of the first and second RSS to generate a chimeric polynucleotide comprising the first and second coding sequences and (b) expression of the chimeric polynucleotide, thereby generating variants of the fusion protein.

Certain embodiments of the invention relate to a method as described above in which the second nucleic acid sequence further comprises a third RSS and the method further comprises the steps of: providing a third nucleic acid sequence comprising a third coding sequence encoding a third portion of the fusion protein and further comprising a fourth RSS capable of functional recombination with the third RSS, and introducing the third nucleic acid sequence into the recombination-competent host cell, and in which culturing the host cell further allows for recombination of the third and fourth RSS and the chimeric polynucleotide comprises the first, second and third coding sequences.

Another aspect of the invention relates to a polynucleotide comprising a first nucleic acid sequence comprising a first coding sequence encoding a first portion of a fusion protein and further comprising a first recombination signal sequence (RSS) and a second nucleic acid sequence comprising a second coding sequence encoding a second portion of the fusion protein and further comprising a second RSS capable of functional recombination with the first RSS.

Certain embodiments of the invention relate to a polynucleotide as described above in which the second nucleic acid sequence further comprises a third RSS and the polynucleotide further comprises a third nucleic acid sequence comprising a third coding sequence encoding a third portion of the fusion protein and further comprising a fourth RSS capable of functional recombination with the third RSS.

Another aspect of the invention relates to an isolated host cell comprising a polynucleotide as described herein.

Another aspect of the invention relates to a variant fusion protein produced by the methods described herein.

Another aspect of the invention relates to a peptide-grafted immunoglobulin comprising an immunoglobulin scaffold and a heterologous polypeptide inserted into at least one CDR of the immunoglobulin scaffold, wherein the heterologous polypeptide comprises a peptide sequence capable of binding to a GPCR, an upstream flanking sequence comprising between about 1 and about 20 amino acids and a downstream flanking sequence comprising between about 1 and about 20 amino acids.

BRIEF DESCRIPTION OF THE DRAWINGS

These and other features of the invention will become more apparent in the following detailed description in which reference is made to the appended drawings.

FIG. 1 presents (A) a schematic representation of a peptide grafting acceptor vector to generate antibody variants, and (B) the nucleotide sequence of the vector [SEQ ID NO:28].

FIG. 2 presents a modified fibronectin sequence [SEQ ID NO:35] that includes an RGD peptide encoding sequence in all three reading frames [SEQ ID NOs:9-11].

FIG. 3 presents (A) a schematic representation of a cassette for insertion into the fusion protein grafting acceptor vector shown in FIG. 1(A) that includes amino acids 7-37 of GLP-1, (B) the nucleotide sequence [SEQ ID NO:36] with coding sequence in bold and (C) the amino acid sequence [SEQ ID NO:38] of the cassette shown in (A), (D) a schematic representation of a cassette that includes amino acids 13-33 of GLP-1, (E) the nucleotide sequence [SEQ ID NO:37] with coding sequence in bold and (F) the amino acid sequence [SEQ ID NO:39] of the cassette shown in (D).

FIG. 4 presents (A) a schematic representation of a cassette for insertion into the fusion protein grafting acceptor vector shown in FIG. 1(A) that includes amino acids 1-39 of exendin-4, (B) the nucleotide sequence [SEQ ID NO:40] and (C) the amino acid sequence [SEQ ID NO:43] of the cassette shown in (A), (D) a schematic representation of a cassette that includes amino acids 9-39 of exendin-4, (E) the nucleotide sequence [SEQ ID NO:41] and (F) the amino acid sequence [SEQ ID NO:44] of the cassette shown in (D), (G) a schematic representation of a cassette that includes amino acids 15-27 of exendin-4, (H) the nucleotide sequence [SEQ ID NO:42] and (F) the amino acid sequence [SEQ ID NO:45] of the cassette shown in (G).

FIG. 5 presents (A) the IL-8 nucleotide and amino acid sequences [SEQ ID NOs:46 and 47, respectively], (B) the IL-8 nucleotide sequence for peptide grafting [SEQ ID NO:12], (C) the amino acid and nucleotide sequences of the binding domain of Gro-alpha [SEQ ID NOs:48 and 49, respectively], (D) the nucleotide sequence of Gro-alpha for peptide grafting [SEQ ID NO:49], and (E) the nucleotide sequence of LL-37 with a silent substitution of (G>A) that places a stop codon in reading frame #2 [SEQ ID NO:50].

FIG. 6 presents an alignment of the amino acid sequences of the receptor dimerization arm for various ErbB proteins [SEQ ID NOs:13-16].

FIG. 7 presents (A) a schematic representation of an acceptor vector for grafting peptides into the 10Fn3 loop, and (B) the nucleotide sequence of the vector [SEQ ID NO:63].

FIG. 9 presents (A) a schematic representation of a cassette for generating in-frame selection of a secreted protein (shown is Ig Kappa) showing from constant region to poly(A), and (B) the nucleotide sequence of the cassette [SEQ ID NO:64] with the furin cleavage site in bold.

FIG. 10 presents (A) a schematic overview of a method of grafting peptides in accordance with one embodiment of the invention in which immunoglobulin D segments are replaced with peptide sequences, and (B) a schematic of a recombination substrate for grafting peptides in accordance with another embodiment of the invention in which peptide sequences are grafted into other CDRs of immunoglobulin heavy or light chains.

FIG. 11 presents (A) a cassette comprising a 5' RSS [SEQ ID NO:17], 5' and 3' flanking sequences and a 3' RSS [SEQ ID NO:18] for peptide grafting of an anti-TPO receptor peptide (encoded by nucleotide sequence [SEQ ID NO:65]), (B) a cassette comprising a 5' RSS [SEQ ID NO:17], 5' and 3' flanking sequences and a 3' RSS [SEQ ID NO:18] for peptide grafting of an anti-GLP-1 receptor peptide, and (C) nucleotide sequences encoding exemplary anti-GLP-1 receptor peptides [SEQ ID NOs:66-70] for incorporation into the cassette shown in (B). N=any nucleotide, and K=T or G.

FIG. 12 presents the results of FACS scanning analysis of peptide-grafted immunoglobulins in which the peptide has replaced the D segment in the heavy chain CDR3: (A) binding of immunoglobulins grafted with an anti-TPO receptor peptide to the TPO receptor, and (B) binding of immunoglobulins grafted with an anti-GLP-1 receptor peptide to the GLP-1 receptor.

DETAILED DESCRIPTION OF THE INVENTION

Figure 8:
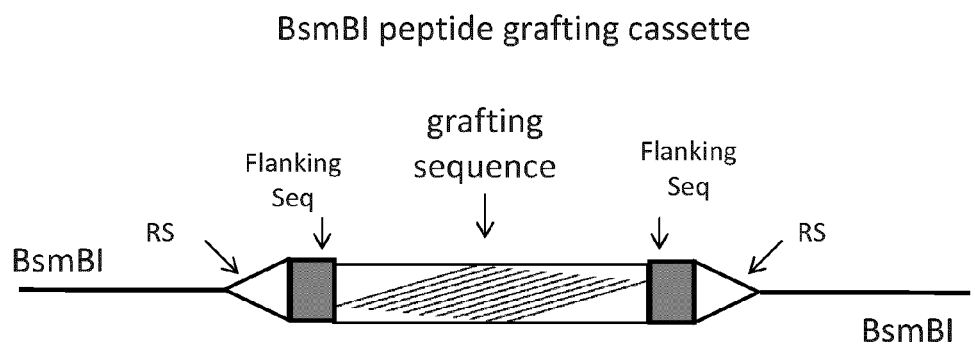
FIG. 8 presents a schematic representation of a generalised cassette for peptide grafting in accordance with one embodiment of the invention.

As illustrated herein, the use of components of the antibody V(D)J recombination system can be expanded outside their natural role of mediating assembly of antibody gene segments and may be used to generate sequence diversity in a variety of contexts and, specifically, at the junction region(s) of fusion proteins.

Fusion proteins in the context of the present invention include, in certain embodiments, fusions comprising two full length proteins and fusions comprising two or more protein domains or polypeptides, each associated with a desired function or activity. The protein domains or polypeptides may be derived from the same protein or they may be derived from different proteins, or one or more of the protein domains or polypeptides may be a non-naturally occurring polypeptide. Thus, in certain embodiments, such polypeptides may, for example, be sequences representing all or a portion of a known protein having the desired function or activity, or they may be non-naturally occurring sequences that have been shown to have a desired function or activity. In the simplest case, fusion proteins can be the result of the amino acid sequences corresponding to each protein, domain or polypeptide, being brought together to form the fusion protein. Fusion proteins may also comprise additional amino acids separating each protein, domain or polypeptide, that are not necessarily part of the protein, domain or polypeptide. These additional amino acids sequences joining the components of the fusion protein are referred to as a linker. Accordingly, in certain embodiments of the invention, a fusion protein may be defined as a protein in which two or more amino acid sequences that are not normally contiguous have been joined together. In certain embodiments, the fusion protein can comprise a small functional region of one protein inserted into a region of a second protein, protein domain or protein scaffold—the process used to generate such fusion proteins is often referred to as "peptide grafting."

One challenge with joining proteins, protein domains or polypeptides to produce a fusion protein is that the context and conformation of the fusion may not be appropriate for the functioning of the proteins, domains or polypeptides. The present invention recognizes that the natural V(D)J reaction has inherent characteristics, specifically the imprecise junctions generated during the joining process, that make it useful as a general means to generate sequence diversity and thus may be employed in the context of fusion proteins to generate a large repertoire of junctions between the component portions of the fusion protein.

Certain embodiments of the present invention thus relate to methods of generating fusion protein variants by introducing sequence diversity at the junction region or regions of the fusion protein and allows for the identification of a variant which preferably retains the optimal activity of the protein, or domain or polypeptide, of interest.

Certain embodiments of the invention relate to peptide-grafted immunoglobulins which comprise one or more peptides grafted into a CDR of an immunoglobulin scaffold. In some embodiments, the peptide is targeted to a membrane-bound receptor, such as a G-protein coupled receptor (GPCR) or ion channel.

In certain embodiments, the methods of the invention comprise generating fusion protein variants by introducing sequence diversity at a junction region between two proteins, domains or polypeptides. In some embodiments, therefore, the methods make use of a "bipartite" reaction that involves a single pair of RSSs, which may be used with or without flanking sequences, as described in more detail below.

In some embodiments, the methods comprise generating sequence diversity at two or more junctions between proteins, domains or polypeptides. For example, in certain embodiments, the methods are used for peptide grafting in which a protein domain or polypeptide having a desired function is integrated into a structural framework of a stably folded protein with suitable properties for the desired purpose. Examples of such frameworks include antibody scaffolds and other protein scaffolds consisting of a stably folded non-Ig protein. In some embodiments, therefore, the methods make use of a "tripartite" reaction that involves a RSS flanked donor cassette sequence (i.e. two pairs of RSSs) and diversity is generated at each junction. In certain embodiments, diversity at both junctions can be accomplished by two sequential bipartite reactions.

Accordingly, certain embodiments of the invention relate to methods of generating sequence diversity at a junction between proteins, protein domains or polypeptides comprised by a fusion protein by providing polynucleotides comprising coding sequences for the proteins, domains or polypeptides, and further comprising recombination signal sequences (RSSs) and subsequent introduction of the polynucleotides into a recombination-competent host cell, specifically a host cell that is capable of expressing at least RAG-1 and RAG-2 or functional fragments thereof, resulting in the generation and expression of variant fusion proteins. In certain embodiments, the present invention also relates to polynucleotides for generating variant fusion proteins comprising coding sequences for the constituent proteins, or domains or polypeptides, and further comprising recombination signal sequences (RSSs), as well as compositions comprising same. In some embodiments, the invention relates to fusion proteins generated from recombination of such polynucleotides and compositions comprising same.

Definitions

Unless defined otherwise, all technical and scientific terms used herein have the same meaning as commonly understood by one of ordinary skill in the art to which this invention belongs.

The term "domain," as used herein with respect to a protein refers to a portion of the protein that has, or is predicted to have, a desired function. Proteins may comprise more than one domain as distinct, non-contiguous regions of the protein. A domain can vary in size from a few amino acids to several hundred amino acids in length. As such, a domain may comprise substantially all of the protein from which it is derived, or it may be a fragment of the protein. In this context, a fragment is generally considered to be a polypeptide that has an amino-terminal and/or carboxy-terminal deletion compared to a full-length protein. Fragments typically are between about 3 and about 300 amino acids in length. In certain embodiments, a fragment is at least 3, 4, 5, 6, 7, 8, 9 or 10 amino acids long, and no more than 200 amino acids long, for example, between about 5 and 200, between about 5 and 190, between about 5 and 180, between about 5 and 170, between about 5 and 160, between about 5 and 150, between about 5 and 140, between about 5 and 130, between about 5 and 120, between about 5 and 110, between about 5 and 100, between about 5 and 90, between about 5 and 80, between about 5 and 70, between about 5 and 60 and between about 5 and 50 amino acids long. The term "domain" also encompasses variants of the naturally-occurring domain provided that the variants retain at least partial functionality, for example, 10%, 20%, 30%, 40%, 50% or more of the activity of the naturally occurring domain. Variants may be constructed by, for example, substituting or deleting residues not needed for functionality or by inserting residues that will not adversely affect functionality.

The term "polypeptide," as used herein refers broadly to an amino acid chain that may have various lengths, including a chain length shorter than 50 amino acids. A polypeptide may therefore range from about 2 to about 3000 amino acids in length, for example, between about 2 and about 1500 amino acids, between about 2 and about 1000 amino acids, between about 2 and about 500 amino acids, between about 2 and about 300 amino acids in length. The term as used herein encompasses analogs and mimetics as known in the art that mimic structural and thus biological function.

"Naturally occurring," as used herein with reference to an object, refers to the fact that the object can be found in nature. For example, an organism, or a polypeptide or polynucleotide sequence that is present in an organism that can be isolated from a source in nature and which has not been intentionally modified by man in the laboratory is naturally occurring.

The term "isolated," as used herein with reference to a material, means that the material is removed from its original environment (for example, the natural environment if it is naturally occurring). For example, a naturally occurring polynucleotide or polypeptide present in a living animal is not isolated, but the same polynucleotide or polypeptide separated from some or all of the co-existing materials in the natural system, is isolated. Such polynucleotides could be part of a vector and/or such polynucleotides or polypeptides could be part of a composition, and still be isolated in that such vector or composition is not part of its natural environment.

The term "deletion" as used herein with reference to a polynucleotide, polypeptide or protein has its common meaning as understood by those familiar with the art and may refer to molecules that lack one or more of a portion of a sequence from either terminus or from a non-terminal region, relative to a corresponding full length molecule. For example, in certain embodiments, a deletion may be a deletion of between 1 and about 1500 contiguous nucleotide or amino acid residues from the full length sequence.

The term "expression vector," as used herein, refers to a vehicle used in a recombinant expression system for the purpose of expressing a polynucleotide sequence constitutively or inducibly in a host cell, including prokaryotic, yeast, fungal, plant, insect or mammalian host cells, either in vitro or in vivo. The term includes both linear and circular expression systems. The term includes expression systems that remain episomal and expression systems that integrate into the host cell genome. The expression systems can have the ability to self-replicate or they may not (for example, they may drive only transient expression in a cell).

The term "antigen-binding domain," as used herein, refers to one or more fragments of an antibody that retain the ability to specifically bind to an antigen. Non-limiting examples of antibody fragments comprising antigen-binding domains include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulphide bridge at the hinge region; (iii) a Fd fragment consisting of the $V_H$ and $C_m$ domains; (iv) a Fv fragment consisting of the $V_L$ and $V_H$ domains of a single arm of an antibody, (v) a dAb fragment, which consists of a $V_H$ domain; and (vi) an isolated complementarity determining region (CDR). The term also encompasses single chain Fv (scFv) fragments, which comprise the two domains of the Fv fragment, $V_L$ and $V_H$, joined using recombinant methods by a synthetic linker that enables them to be made as a single protein chain in which the $V_L$ and $V_H$ regions pair to form monovalent molecules.

The term "bipartite reaction," as used herein, refers to a recombination reaction that involves a single pair of RSSs (12 bp and 23 bp, or 23 bp and 12 bp). When V(D)J recombination occurs it generates a double-stranded break in the nucleic acid sequence containing the RSSs. The double-stranded break is targeted as a result of the RSSs in that a 12 bp and 23 bp RSS are assembled with the RAG proteins to initiate the reaction. The ends of the DNA that will be subsequently rejoined will comprise the coding joint (or junction). An example of a bipartite reaction is in vivo immunoglobulin light chain recombination, which joins the Variable to the Joining segment—these two segments comprise the "substrates" for the bipartite reaction. The bipartite reaction can occur in the presence or absence of TdT.

The term "tripartite reaction," as used herein, refers to a recombination reaction that involves two pairs of RSSs (each 12 bp and 23 bp, or 23 bp and 12 bp). An example of a tripartite reaction is in vivo immunoglobulin heavy chain recombination, which joins the V, the D and the J gene segments. A tripartite reaction generates two independent coding junctions. Two sequential bipartite reactions can be considered to be a tripartite reaction in that a tripartite reaction may comprise two bipartite reactions occurring in the same substrate, usually (but not always) in close temporal time. The tripartite reaction can occur in the presence or absence of TdT.

The term "recombination-competent" when used herein with reference to a host cell means that the host cell is capable of mediating RAG-1/RAG-2 recombination. The host cell may, therefore, express RAG-1 and RAG-2, or functional fragments thereof, or may be modified (for example, transformed or transfected with appropriate genetic constructs) such that it expresses RAG-1 and RAG-2, or functional fragments thereof. The expression of one or both of RAG-1 and RAG-2 in the recombination-competent host cell may be constitutive or it may be inducible. A recombination-competent host cell may optionally further express TdT, or a functional fragment thereof.

As used herein, the term "about" refers to an approximately +/−10% variation from a given value. It is to be understood that such a variation is always included in any given value provided herein, whether or not it is specifically referred to.

The term "plurality" as used herein means more than one, for example, two or more, three or more, four or more, and the like.

Methods of Generating Variant Fusion Proteins

The methods according to the present invention comprise utilizing the V(D)J recombination system to generate sequence diversity in fusion proteins.

The use of V(D)J recombination as a method to modify an existing protein sequence as opposed to assembly of a protein from gene segments can present a number of challenges, including a number of features of the reaction that are under-appreciated in the art.

For example, the V(D)J recombination reaction is known to bring together different DNA sequences and result in large chromosomal deletions, which suggests that its utility to introduce sequence diversity would be limited to extended stretches of nucleic acid sequence that permit such large deletions. As demonstrated herein, however, the components of the V(D)J recombination system can be manipulated to allow the utility of this reaction to be extended to include targeted sequences within a restricted size of protein sequence, such as a small loop.

In addition, although the involvement of the enzyme TdT, which is responsible for non-template nucleotide additions (N-additions), is central to the reaction, the net size of the product following gene segment assembly is frequently less than would be predicted if no deletions or additions were to occur, i.e. the V(D)J reaction often results in a net loss of sequence. For example, the average size of the assembled germline V, D and J segments, without any additions or deletions, is 15 amino acids and yet the average CDR3 reported in humans is 12-13 amino acids, which includes N additions from TdT (Rock et al., 1994, *J Exp Med,* 179:323-328).

Another feature of V(D)J recombination that is underappreciated is that the additions introduced by TdT are small. In vivo and in vitro TdT additions have been reported to be typically an average of 2-4 nucleotides (Kallenbach et al., 1992, *PNAS USA,* 89:2799-2903; Bentolila et al., 1997, *J Immunol.,* 158:715-723). A larger number of amino acid changes per variant is generally preferred for mutagenesis techniques in order to allow for a greater amount of diversity to be sampled.

The above-noted features of V(D)J recombination can represent challenges to the application of V(D)J recombination to a non-antibody scaffold. The methods provided by the present invention, however, allow for this random process to be used as a valuable tool for semi-rational protein engineering.

In some embodiments, for example, the methods employ flanking sequences adjacent to one or more of the RSSs to allow for incorporation of additional sequences into the junction region(s) of the fusion protein to minimise any net deletion effect of the V(D)J recombination reaction and/or to introduce additional functionality by way of addition of specific amino acid residues. By way of example, when the targeted location is within a small loop of a protein, such as the CDR3 of an antibody, flanking sequences may be used in conjunction with the RSSs to ensure that the loop retains a minimal length once sequence diversification has taken place.

In certain embodiments, the methods of the present invention allow for the generation of both composition and length diversity simultaneously. In some embodiments, the methods are entirely cell-mediated thus eliminating the requirement for cloning of variants and their subsequent introduction into cells as is required by other methods.

The methods according to the present invention generally comprise the steps of providing polynucleotides comprising coding sequences for the components of a fusion protein (i.e. the constituent proteins, or domains or polypeptides) and further comprising recombination signal sequences (RSSs), introducing the polynucleotides into a recombination-competent host cell, and culturing the cell in vitro under conditions that allow for recombination and expression of the polynucleotides, thus generating a variant fusion protein. In certain embodiments, the methods further comprise screening the variant fusion protein for defined functional characteristics.

The host cell may constitutively express RAG-1 and RAG-2, and optionally TdT, or one or more of these proteins may be under inducible control. In certain embodiments, expression of one or more of RAG-1 and RAG-2, and optionally TdT, in the host cell is under inducible control allowing, for example, for expansion of the host cell prior to the induction of sequence diversity generation. Accordingly, in some embodiments, the method comprises the steps of: providing polynucleotides comprising coding sequences for the components of a fusion protein (i.e. the constituent proteins, domains or polypeptides) and further comprising recombination signal sequences (RSSs), introducing the polynucleotides into a recombination-competent host cell, wherein expression of one or more of RAG-1, RAG-2 and TdT is under inducible control, culturing the host cell under conditions allowing expansion of the host cell, inducing expression of one or more of RAG-1, RAG-2 and TdT, culturing the expanded host cells under conditions allowing recombination and expression of the polynucleotides, thereby generating a fusion protein variant.

In certain embodiments, the methods are used to generate a library of fusion protein variants that can be subsequently screened for variants having defined functional characteristics, and comprise the steps of: providing polynucleotides comprising coding sequences for the components of a fusion protein (i.e. the constituent proteins, domains or polypeptides) and further comprising recombination signal sequences (RSSs), introducing the polynucleotides into recombination-competent host cells, and culturing the cells under conditions that allow for recombination and expression of the polynucleotides, thus generating a library of variant fusion proteins. In certain embodiments, the methods further comprise screening the library of variant fusion proteins for variants having the defined functional characteristics.

In certain embodiments relating to peptide grafting in which the protein scaffold is an immunoglobulin, the methods may be used to generate a library of peptide-grafted variants by replacing the D segment-encoding region of a heavy chain with a cassette comprising a peptide encoding sequence flanked by RSS sequences (see FIG. 10A). The library of peptide-grafted variants thus generated will represent a wide variety of possible V segment-peptide-J segment combinations that can be screened for variants having the required functional characteristics.

Light chains or other heavy chain CDRs can also be similarly grafted by using a RSS flanked peptide sequence encoding cassette as an artificial D segment in a light chain or heavy chain CDR recombination substrate (see FIG. 10B). The library of peptide-grafted variants thus generated will represent a variety of antibodies with the peptide encoded DNA sequences and appropriate flanking sequences inserted into the targeted CDR.

The polynucleotides may be introduced into the host cell by way of a suitable vector or vectors and may be, for example, stably integrated into the genome of the cell, stably maintained exogenously to the genome or transiently expressed.

In some embodiments, the coding sequence for the protein, domain or polypeptide comprised by the polynucleotide is operably linked to a regulatable promoter, for example, an inducible promoter, such that expression of the encoded sequence can be controlled.

In some embodiments, the polynucleotides may also comprise additional coding sequences that encode a polypeptide that provides additional functionality to the fusion protein. For example, the polypeptide may localize the fusion protein to the cell membrane, nucleus or other organelle; provide for secretion of the fusion protein from the cell; introduce a detectable label, or the like.

In certain embodiments, the recombination is controlled. In some embodiments, the host cell is capable of cell divisions without recombination. As described herein, these and related embodiments permit expansion of the host cell population prior to the initiation of recombination events that give rise to sequence diversity in the fusion protein. Control of recombination in such host cells may be achieved, for example, through the use of an operably linked recombination control element (such as an inducible recombination control element, which may be a tightly regulated inducible recombination control element), and/or through the use of one or more low efficiency RSSs in the nucleic acid composition(s) (as described in more detail below), and/or through the use of low host cell expression levels of one or more of RAG-1 or RAG-2, and/or through design of the polynucleotide to integrate at a chromosomal integration site offering poor accessibility to host cell recombination mechanisms (for example, RAG-1 and/or RAG-2).

In some embodiments, the methods further comprise selecting a variant having the desired functional characteristics, and subjecting the variant to one or more additional rounds of sequence diversity generation in order to obtain further variants having optimised functional characteristics.
Fusion Protein Components The methods of the present invention may be used to generate sequence diversity in fusion proteins comprised of a wide variety of proteins, protein domains or polypeptides. The methods may be used, for example, to generate variants of a known fusion protein having improved activity, or they may be used to generate new fusion proteins with new activities or combinations of activities.

In general, the components for fusion proteins are selected on the basis that they have an activity or function that renders them useful for a given application, for example, therapeutic, diagnostic, nutraceutical, agricultural, or industrial application, or otherwise impart desirable characteristics to the fusion protein, such as improved stability, improved pharmacokinetics, decreased antigenicity, and the like.

For example, components may be selected that have activities/functions such as protein-ligand interaction, protein-protein interaction, enzymatic activity, light capture and emission, antigenic activity, and the like.

The components of the fusion protein may be derived from naturally occurring proteins or polypeptides, or they may be non-naturally occurring polypeptides known or demonstrated to have a desired activity or function.

Examples of naturally occurring proteins and polypeptides of interest which may be used in their entirety, or as a source of a domain having a desired function, include, but are not limited to, antibodies (mAbs such as IgG, IgM, IgA, and the like), hormones, protease inhibitors, antibiotics, antimicrobials, HIV entry inhibitors, collagen, human lactoferrin, cytokines, receptors, growth factors, toxins, protein and peptide antigens, enzymes involved in primary and secondary intracellular signaling and metabolic pathways (such as enterokinase, beta-glucuronidase (GUS), phytase, carbonic anhydrase, and the like), industrial enzymes (such as hydrolases, glycosidases, cellulases, oxido-reductases, and the like) and fluorescent proteins (such as green fluorescent protein (GFP), enhanced cyan fluorescent protein (ECFP), red fluorescent protein (DsRed) and the like).

In certain embodiments, the fusion protein is comprised of a polypeptide with a desired activity that has been "grafted" into a protein scaffold. Examples of polypeptides that may be used for such "peptide grafting" include polypeptides derived from various ligands, toxins, antigens, protein domains involved in protein-protein interactions, and the like. Certain embodiments of the invention contemplate peptide grafting using peptides that target a membrane bound receptor, such as a GPCR, ion channel, a member of the hematopoietic receptor superfamily or an integrin.

Various protein scaffolds are known. For example, immunoglobulins such as antibodies or antibody fragments that comprise an antigen-binding domain are suitable for use as protein scaffolds. Examples include, but are not limited to, IgA, IgA2, IgD, IgE, IgGs (i.e. IgG1, IgG2, IgG3 and/or IgG4) and IgM antibodies; camelid antibodies; shark antibodies; antibody fragments such as Fab, Fab', F(ab')$_2$, Fd, Fv and single-chain Fv (scFv) antibody fragments; diabodies, nobodies and fluorobodies. Certain embodiments of the invention relate to immunoglobulin scaffolds.

Non-immunoglobulin protein scaffolds are also known and include various stably folded non-Ig proteins as described in Binz, et al. (2005, *Nature Biotechnology*, 23(10):1257-1268), Nygren & Skerra (2004, *J Immunol. Methods*, 290:3-28) and Gebauer & Skerra (2009, *Curr. Op. Chem. Biol.*, 13:245-255). Examples of such protein scaffolds include, but are not limited to, cytotoxic lymphocyte-associated antigen-4 (CTLA-4), Tendamistat, 10$^{th}$ fibronectin type 3 domain ($^{10}$FN3), carbohydrate-binding module 4 of family 2 of xylanase of *Rhodothermus marinus* (CBM4-2), lipocalins ("anticalins"), T-cell receptor, Protein A domain (protein Z), immunity protein 9 (Im9), designed ankyrin repeat proteins (DARPins), designed tetratrico repeat (TPR) proteins, zinc finger proteins, protein VIII of filamentous bacteriophage (pVIII), avian pancreatic polypeptide, general control nonderepressible (yeast transcription factor) (GCN4), WW domain, Src homology domain 3 (SH3), Src homology domain 2 (SH2), PDZ domains, TEM-1, β-lactamase, green fluorescent protein (GFP), thioredoxin, staphylococcal nuclease, plant homeodomain finger protein (PHD-finger), chymotrypsin inhibitor 2 (CI-2), bovine pancreatic trypsin inhibitor (BPTI), Alzheimer amyloid β-protein precursor inhibitor (APPI), human pancreatic secretory trypsin inhibitor (hPSTI), ecotin, human lipoprotein-associated coagulation inhibitor domain 1 (LACI-D1), leech-derived trypsin inhibitor (LDTI), MTI-II, scorpion toxins, insect defensin A peptide, *Ecballium elaterium* trypsin inhibitor II (EETI-II), Min-23, cellulose-binding domain (CBD), periplasmic binding proteins (PBP), cytochrome $b_{562}$, low density lipoprotein (ldl) receptor domain A, γ-crystallin, ubiquitin, transferrin and C-type lectin-like domain. T-cell receptors are also useful protein scaffolds in certain embodiments.

Protein scaffolds can be considered as falling into two groups: a first group consisting of loop presenting scaffolds (which includes scaffolds presenting a single loop and scaffolds presenting a plurality of loops), and a second group consisting of interface presenting scaffolds, in which the binding site is presented on a secondary structure element. Examples of scaffolds in the first group include, but are not limited to, Kunitz domain inhibitors, hPSTI, APPI, LACI-D1, ecotin, members of the knottin family of proteins (such as EETI-II), thioredoxin, staphylococcal nuclease, immunoglobulins, CTLA-4, FN3, Tendamistat, GFP, members of the lipocalin family of proteins, and bilin binding protein (BBP) from *Pieris brassicae*. Examples in the second group include, but are not limited to, the immunoglobulin binding domain of Staphylococcal protein A (SPA) ("affibodies"), DARPins, leucine-rich repeat polypeptides, PDZ domains, cellulose binding domains (CBD), members of the lipocalin family of proteins, γ-crystallins, and $Cys_2His_2$ zinc-finger polypeptides. The binding domains of both of these groups of proteins have been studied and regions suitable for modification have been identified (see review by Nygren & Skerra, ibid.).

Polynucleotides

The methods of the present invention employ polynucleotides that comprise a coding sequence, i.e. a nucleic acid sequence encoding the protein, domain or polypeptide of interest. The polynucleotides may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A nucleic acid sequence which encodes a protein, domain or polypeptide for use in the methods of the present invention may be identical to the coding sequence known in the art for the protein, domain or polypeptide or may be a different coding sequence, which, as a result of the redundancy or degeneracy of the genetic code, encodes the same protein.

The polynucleotides may include only the coding sequence for the protein, domain or polypeptide; the coding sequence and additional coding sequence (for example, encoding a polypeptide providing additional functionality to the final fusion protein); the coding sequence (and optionally additional coding sequence) and non-coding sequence, such as introns or non-coding sequences 5' and/or 3' of the coding sequence. The coding sequence may be in the form of one or more exons, which may be contiguous or may be interspersed with one or more introns. The non-coding sequences may include, for example, one or more regulatory nucleic acid sequences that may be a regulated or regulatable promoter, enhancer, other transcription regulatory sequence, repressor binding sequence, translation regulatory sequence or other regulatory nucleic acid sequence.

The coding sequence for various proteins, domains or polypeptides that may be used in the methods of the invention may be a known sequence that can be obtained, for example, from public databases such as GenBank. Many proteins have been cloned and polynucleotides comprising the coding sequences for these proteins may be obtained from commercial sources. Alternatively, coding sequences can be obtained from an appropriate source, or otherwise generated or synthesized, using standard molecular biology techniques, such as those described in *Molecular Cloning: A Laboratory Manual* (Third Edition) (Sambrook, et al., 2001, Cold Spring Harbour Laboratory Press, NY) and *Current Protocols in Molecular Biology* (Ausubel et al. (Ed.), 1987 & Updates, J. Wiley & Sons, Inc., Hoboken, N.J.). In addition, many companies offer custom gene synthesis and may be used as a source of coding sequences.

In certain embodiments, the polynucleotide may be codon-optimized according to standard codon usage preference tables, such that its expression in the chosen host cell is optimized.

Certain embodiments of the invention encompass the use of variant polynucleotides in the present methods, for example, polynucleotides that encode analogs and/or derivatives of a protein (or a protein domain or polypeptide). The polynucleotide variants may be, for example, naturally-occurring allelic variants of the polynucleotide or non-naturally occurring variants. As is known in the art, an allelic variant is an alternate form of a nucleic acid sequence which may have at least one of a substitution, a deletion or an addition of one or more nucleotides, any of which does not substantially alter the function of the encoded protein or polypeptide. Non-naturally occurring polynucleotide variants may be accomplished by a number of conventional methods. For example, mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion(s), substitution(s), or deletion(s). Alternatively, oligonucleotide-directed site-specific mutagenesis procedures can be employed to provide an altered gene wherein predetermined codons can be altered by substitution, deletion or insertion. Exemplary methods of making such alterations are described, for example, in *Molecular Cloning: A Laboratory Manual* (Third Edition) (Sambrook, et al., 2001, Cold Spring Harbour Laboratory Press, NY) and *Current Protocols in Molecular Biology* (Ausubel et al. (Ed.), 1987 & Updates, J. Wiley & Sons, Inc., Hoboken, N.J.).

In certain embodiments of the invention, for example, those relating to peptide grafting and/or those that involve tripartite reactions, polynucleotides may be provided in the form of a cassette comprising a sequence encoding a peptide flanked by pairs of RSS sequences. Such cassettes may be inserted into a larger polynucleotide encoding the protein scaffold, which is then transfected into an appropriate host cell to allow recombination to occur. In some embodiments, such cassettes may comprise a peptide-encoding sequence flanked by pairs of RSS sequences with degenerate nucleotide sequences inserted between the RSS sequences and the peptide encoding sequences. The degenerate sequences allow for introduction of additional sequence diversity over that provided by the V(D)J recombination and are typically about 3 and about 50 nucleotides in length, for example, between about 3 and about 40 nucleotides, between about 3 and about 30 nucleotides, between about 3 and about 20 nucleotides, between about 3 and about 18 nucleotides or between about 3 and about 15 nucleotides in length. Non-limiting examples of cassettes comprising degenerate sequences are shown in FIG. 11.

Recombination Signal Sequences (RSSs)

The polynucleotides employed in the methods of the invention comprise recombination signal sequences (RSSs). The RSS in accordance with the present invention preferably consist of two conserved sequences (for example, heptamer, 5'-CACAGTG-3', and nonamer, 5'-ACAAAAACC-3'), separated by a spacer of either 12+/−1 bp (a "12-signal" RSS) or 23+/−1 bp (a "23-signal" RSS). Within the host cell, two RSSs (one 12-signal RSS and one 23-signal RSS) are selected and rearranged under the "12/23 rule." Recombination does not occur between two RSS signals with the same size spacer. As would be appreciated by one of skill in the art, the orientation of the RSS determines if recombination results in a deletion or inversion of the intervening sequence.

As a result of extensive investigations of RSS processes, it is known in the art which nucleotide positions within RSSs cannot be varied without compromising RSS functional activity in genetic recombination mechanisms, which nucleotide positions within RSSs can be varied to alter (for example, increase or decrease in a statistically significant manner) the efficiency of RSS functional activity in genetic recombination mechanisms, and which positions within RSSs can be varied without having any significant effect on RSS functional activity in genetic recombination mechanisms (see, for example, Ramsden et al., 1994, *Proc Natl Acad Sci USA* 88(23): 10721-10725; Akamatsu et al., 1994, *J Immunol* 153:4520; Hesse et al., 1989, *Genes Dev* 3:1053; Fanning et al., 1996, *Immunogenetics* 44(2):146-150; Larijani et al., 1999, *Nucleic Acids Res* 27(11):2304-2309; Nadel et al., 1998, *J Exp Med* 187:1495; Lee et al., 2003, *PLoS Biol* 1:E1; and Cowell et al., 2004, *Immunol. Rev.* 200:57).

In certain embodiments, the invention makes use of an RSS that is known in the art. Also contemplated in some embodiments are sequence variants of known RSSs that comprise one or more nucleotide substitutions (for example, about 1, 2, 3, 4, 5, 6, 7, 8, 9, 10, 11, 12, 13, 14, 15, 16, 17, 18 or more substitutions) relative to a known RSS sequence and which, by virtue of such substitutions, predictably have low efficiency (for example, about 1% or less, relative to a high efficiency RSS), medium efficiency (for example, about 10% to about 20%, relative to a high efficiency RSS) or high efficiency. Also contemplated in some embodiments are those RSS variants for which one or more nucleotide substitutions relative to a known RSS sequence will have no significant effect on the recombination efficiency of the RSS (for example, the success rate of the RSS in promoting formation of a recombination product, as known in the art).

Examples of RSS sequences known to the art, including their characterization as high, medium or low efficiency RSSs, are presented in Table 1A & B.

TABLE 1A

EXEMPLARY RECOMBINATION SIGNAL SEQUENCES
(12 NUCLEOTIDE SPACER)

| | Heptamer H12 | Spacer S12 | Nonamer N12 |
|---|---|---|---|
| Part I. Efficiency: HIGH | | | |
| 1 | CACAGTG | ATACAGACCTTA [SEQ ID NO: 1] | ACAAAAACC |
| 2 | CACAGTG | CTACAGACTGGA [SEQ ID NO: 2] | ACAAAAACC |
| 3 | CACAGTG | CTCCAGGGCTGA [SEQ ID NO: 3] | ACAAAAACC |
| 4 | CACAGTG | CTACAGACTGGA [SEQ ID NO: 2] | ACAAAAACC |
| 5 | CACAGTG | CTACAGACTGGA [SEQ ID NO: 2] | ACAAAAACC |
| 6 | CACAGTG | CTACAGACTGGA [SEQ ID NO: 2] | ACAAAAACC |
| 7 | CACAGTG | GTACAGACCAAT [SEQ ID NO: 4] | ACAGAAACC |
| Part II. Efficiency: MEDIUM (~10-20% of High) | | | |
| 8 | CACGGTG | CTACAGACTGGA [SEQ ID NO: 2] | ACAAAAACC |
| 9 | CACAATG | CTACAGACTGGA [SEQ ID NO: 2] | ACAAAAACC |
| 10 | CACAGCG | CTACAGACTGGA [SEQ ID NO: 2] | ACAAAAACC |
| 11 | CACAGTG | CTACAGACTGGA [SEQ ID NO: 2] | ACAAAAACC |
| 12 | CACAGTG | CTACAGACTGGA [SEQ ID NO: 2] | ACAAAAACC |
| 13 | CACAGTG | CTACAGACTGGA [SEQ ID NO: 2] | ACAAAAACC |
| 14 | CACAGTG | CTACAGACTGGA [SEQ ID NO: 2] | ACAAAAACC |
| 15 | CACAGTG | CTACAGACTGGA [SEQ ID NO: 2] | ACAAAAACC |
| 16 | CACAGTG | CTACAGACTGGA [SEQ ID NO: 2] | ACAAAAACC |
| 17 | CACAGTG | CTACAGACTGGA [SEQ ID NO: 2] | CAAAAACCC |
| 18 | CACAGTG | CTACAGACTGGA [SEQ ID NO: 2] | ACAAAAACC |
| 19 | CACAATG | CTACAGACTGGA [SEQ ID NO: 2] | ACAAAAACC |
| 20 | CACAGCG | CTACAGACTGGA [SEQ ID NO: 2] | ACAAAAACC |
| Part III. Efficiency: LOW (~1% or less of High) | | | |
| 21 | TACAGTG | CTACAGACTGGA [SEQ ID NO: 2] | ACAAAAACC |
| 22 | GACAGTG | CTACAGACTGGA [SEQ ID NO: 2] | ACAAAAACC |

TABLE 1A-continued

EXEMPLARY RECOMBINATION SIGNAL SEQUENCES (12 NUCLEOTIDE SPACER)

| | Heptamer H12 | Spacer S12 | Nonamer N12 |
|---|---|---|---|
| 23 | CATAGTG | CTACAGACTGGA [SEQ ID NO: 2] | ACAAAAACC |
| 24 | CACAATG | CTACAGACTGGA [SEQ ID NO: 2] | ACAAAAACC |
| 25 | CACAGTG | CTACAGACTGGA [SEQ ID NO: 2] | ACAAAAACC |
| 26 | CAGAGTG | CTCCAGGGCTGA [SEQ ID NO: 3] | ACAAAAACC |
| 27 | CACAGTG | CTCCAGGGCTGA [SEQ ID NO: 3] | AAAAAAACC |
| 28 | CTCAGTG | CTCCAGGGCTGA [SEQ ID NO: 3] | ACAAAAACC |

TABLE 1B

EXEMPLARY RECOMBINATION SIGNAL SEQUENCES (23 NUCLEOTIDE SPACER)

| | Heptamer H23 | Spacer S23 | Nonamer N23 | Ref.* |
|---|---|---|---|---|
| | Part I. Efficiency: HIGH | | | |
| 1 | CACAGTG | GTAGTACTCCACTGTCTGGCTGT [SEQ ID NO: 5] | ACAAAAACC | 4 |
| 2 | CACAGTG | GTAGTACTCCACTGTCTGGCTGT [SEQ ID NO: 5] | ACAAAAACC | 3 |
| 3 | CACAGTG | GTAGTACTCCACTGTCTGGGTGT [SEQ ID NO: 5] | ACAAAAACC | 1 |
| 4 | CACAGTG | TTGCAACCACATCCTGAGTGTGT [SEQ ID NO: 6] | ACAAAAACC | 2 |
| 5 | CACAGTG | GTAGTACTCCACTGTCTGGCTGT [SEQ ID NO: 5] | ACAAAAACC | 2 |
| 6 | CACAGTG | ACGGAGATAAAGGAGGAAGCAGG [SEQ ID NO: 7] | ACAAAAACC | 2 |
| 7 | CACAGTG | GCCGGGCCCCGCGGCCCGGCGGC [SEQ ID NO: 8] | ACAAAAACC | 5 |
| | Part II. Efficiency: MEDIUM (~10-20% of High) | | | |
| 8 | CACAGTG | GTAGTACTCCACTGTCTGGCTGT [SEQ ID NO: 5] | ACAAAAACC | 3 |
| 9 | CACAGTG | GTAGTACTCCACTGTCTGGCTGT [SEQ ID NO: 5] | ACAAAAACC | 3 |
| 10 | CACAGTG | GTAGTACTCCACTGTCTGGCTGT [SEQ ID NO: 5] | ACAAAAACC | 3 |
| 11 | CACAATG | GTAGTACTCCACTGTCTGGCTGT [SEQ ID NO: 5] | ACAAAAACC | 3 |
| 12 | CACAGCG | GTAGTACTCCACTGTCTGGCTGT [SEQ ID NO: 5] | ACAAAAACC | 3 |
| 13 | CACAGTA | GTAGTACTCCACTGTCTGGCTGT [SEQ ID NO: 5] | ACAAAAACC | 3 |
| 14 | CACAGTG | GTAGTACTCCACTGTCTGGCTGT [SEQ ID NO: 5] | ACAATAACC | 3 |
| 15 | CACAGTG | GTAGTACTCCACTGTCTGGCTGT [SEQ ID NO: 5] | ACAAGAACC | 3 |
| 16 | CACAGTG | GTAGTACTCCACTGTCTGGCTGT [SEQ ID NO: 5] | ACACGAACC | 3 |
| 17 | CACAGTG | GTAGTACTCCACTGTCTGGCTGT [SEQ ID NO: 5] | ACAAAAACC | 3 |
| 18 | CACAGTG | GTAGTACTCCACTGTCTGGCTGT [SEQ ID NO: 5] | ACACGAACC | 3 |
| 19 | CACAATG | GTAGTACTCCACTGTCTGGCTGT [SEQ ID NO: 5] | ACAAAAACC | 3 |
| 20 | CACAGCG | GTAGTACTCCACTGTCTGGCTGT [SEQ ID NO: 5] | ACAAAAACC | 3 |
| | Part III. Efficiency: LOW (~1% or less of High) | | | |
| 21 | CACAGTA | GTAGTACTCCACTGTCTGGCTGT [SEQ ID NO: 5] | ACAAAAACC | 3 |
| 22 | CACAGTG | GTAGTACTCCACTGTCTGGCTGT [SEQ ID NO: 5] | ACAAAAACC | 3 |
| 23 | CACAATG | GTAGTACTCCACTGTCTGGCTGT [SEQ ID NO: 5] | ACAAAAACC | 3 |
| 24 | CATAGTG | GTAGTACTCCACTGTCTGGCTGT [SEQ ID NO: 5] | ACAAAAACC | 3 |
| 25 | CACAGTG | GTAGTACTCCACTGTCTGGCTGT [SEQ ID NO: 5] | TGTCTCTGA | 3 |
| 26 | CACAGTG | GTAGTACTCCACTGTCTGGGTGT [SEQ ID NO: 5] | ACAAAAACC | 1 |
| 27 | CACAGTG | GTAGTACTCCACTGTCTGGGTGT [SEQ ID NO: 5] | ACAAAAACC | 1 |

TABLE 1B-continued

EXEMPLARY RECOMBINATION SIGNAL SEQUENCES
(23 NUCLEOTIDE SPACER)

| | Heptamer H23 | Spacer S23 | Nonamer N23 | Ref.* |
|---|---|---|---|---|
| 28 | CACAGTG | GTAGTACTCCACT GTCTGGGTGT [SEQ ID NO: 5] | ACAAAAACC | 1 |

*(1) Akamatsu, 1994, ibid; (2) Cowell, 2004, ibid; (3) Hesse, 1989 ibid; (4) Lee, 2003, ibid; (5) Nadel, 1998,ibid.

In accordance with certain embodiments of the invention, RSSs are used in pairs, in which the first RSS of the pair is capable of functional recombination with the second RSS of the pair (i.e. "complementary pairs"). It is to be understood that when a first RSS (for example present in a first polynucleotide or nucleic acid sequence) is described as being capable of functional recombination with a second RSS (for example present in a second polynucleotide or nucleic acid sequence), such capability includes compliance with the above-noted 12/23 rule for RSS spacers, such that if the first RSS comprises a 12-nucleotide spacer then the second RSS will comprise a 23-nucleotide spacer, and similarly if the first RSS comprises a 23-nucleotide spacer then the second RSS will comprise a 12-nucleotide spacer.

Complementary pairs of RSSs are generally separated by an intervening nucleotide sequence of about 100 bp or more in length. The actual nucleotide sequence of this intervening sequence is not critical to the invention and can accommodate a wide variety of sequences, including for example some selectable markers, some promoters and other regulatory elements such as polyadenylation signals, but preferably does not include insulator-like elements as exemplified by cHS4 and AAV1.

In certain embodiments, the intervening sequence comprises an expression cassette, for example containing a promoter and optionally poly(A) sequences that drive expression of a marker such as GFP or a cell surface marker such that recombination can be monitored, or a selectable marker such as a drug resistance gene such that the cell can be maintained in the un-recombined state via drug selection.

Regardless of the composition of the intervening sequence, it is preferably selected to be at least 100 bp in length, for example, at least 110 bp, at least 120 bp, at least 130 bp, at least 140 bp, at least 150 bp, but may range up to several kilobases in size, for example up to about 5 kb. One skilled in the art will understand that the exact upper limit for the intervening sequence will be dictated by the limitation of the vector system used. In certain embodiments, the intervening sequence is selected to be between about 100 bp and 5 kb, for example, between about 150 bp and 5 kb, between about 180 bp and 5 kb, between about 180 bp and 4 kb, between about 180 bp and 3 kb or between about 180 bp and 2 kb. In some embodiments, the intervening sequence is selected to be between about 100 bp and 1.5 kb, for example, between about 110 bp and 1.5 kb, between about 120 bp and 1.5 kb, between about 130 bp and 1.5 kb, between 140 bp and 1.5 kb, or between about 150 bp and 1.5 kb. In some embodiments, the intervening sequence is selected to be between about 180 bp and 1.9 kb, for example, between about 180 bp and 1.8 kb, between about 180 bp and 1.7 kb, between about 180 bp and 1.6 kb, or between about 180 bp and 1.5 kb. Other exemplary embodiments include intervening sequences of between about 190 bp and 1.5 kb, between about 200 bp and 1.5 kb, between about 210 bp and 1.5 kb, between about 220 bp and 1.5 kb, between about 230 bp and 1.5 kb, between about 240 bp and 1.5 kb, and between about 250 bp and 1.5 kb.

In certain embodiments, flanking sequences are included adjacent to the heptamer of the RSS. In accordance with this embodiment, the flanking sequences may be chosen to have a defined sequence (for example, to specifically encode one or more amino acids) or they may have a random sequence. In some embodiments, the flanking sequences may be selected to introduce certain characteristics at the site of insertion, for example, through the addition of one or more charged amino acids, histidine residues or cysteine residues. In certain embodiments, the flanking sequence may comprise a duplication of a part of the sequence into which the RSSs are to be introduced. In some embodiments, the position and length of the flanking sequences are selected to bias diversification towards one side of the insertion point, or to provide a larger loop size prior to diversification.

When used, the length of the flanking sequence is selected such that it does not interfere with the structural integrity of the target protein. In certain embodiments, the flanking sequences are between about 3 and about 300 bp, for example between about 3 and about 250 bp, between about 3 and about 200 bp, between about 3 and about 150 bp, between about 3 and about 100 bp, between about 3 and about 50 bp, or any amount therebetween.

The RSSs can be introduced into the polynucleotide by standard genetic engineering techniques such as those described in *Molecular Cloning: A Laboratory Manual* (Third Edition) (Sambrook, et al., 2001, Cold Spring Harbour Laboratory Press, NY) and *Current Protocols in Molecular Biology* (Ausubel et al. (Ed.), 1987 & Updates, J. Wiley & Sons, Inc., Hoboken, N.J.).

Additional Coding Sequences

In accordance with certain embodiments of the invention, the polynucleotide may comprise additional coding sequences encoding a polypeptide that provides additional functionality to the fusion protein. Examples of polypeptides that provide additional functionality include, but are not limited to, secretory signal sequences, leader sequences, plasma membrane anchor domain polypeptides such as hydrophobic transmembrane domains (see, for example, Heuck et al., 2002, *Cell Biochem. Biophys.* 36:89; Sadlish et al., 2002, *Biochem J.* 364:777; Phoenix et al., 2002, *Mol. Membr. Biol.* 19:1; Minke et al., 2002, *Physiol. Rev.* 82:429) or glycosylphosphatidylinositol attachment sites ("glypiation" sites) (see, for example, Chatterjee et al., 2001, *Cell Mol. Life Sci.* 58:1969; Hooper, 2001, *Proteomics* 1:748, and Spiro, 2002, *Glycobiol.* 12:43R), and other structural features that assist in localizing the fusion protein to the cell surface such as protein-protein association domains, lipid association domains, glycolipid association domains and proteoglycan association domains, for example, cell surface receptor binding domains, extracellular matrix binding domains, and lipid raft-associating domains (see, for example, Browman et al., 2007, *Trends Cell Biol* 17:394-402; Harder, T., 2004, *Curr Opin Immunol* 16:353-9; Hayashi, T. and Su, T. P., 2005, *Life Sci* 77:1612-24; Holowka, D. and Baird, B., 2001, *Semin Immunol* 13:99-105, and Wollscheid et al., 2004, *Subcell Biochem* 37:121-52).

Other examples of additional coding sequences that may be employed in some embodiments include intracellular targeting sequences, such as nuclear localization sequences and other sequences that target the protein to an intracellular location.

In some embodiments, the additional coding sequences may encode a "tag" to facilitate downstream screening and/or purification of the fusion protein. Examples of such sequences include, but are not limited to, affinity tags such as metal-affinity tags, histidine tags, protein A, glutathione S transferase, Glu-Glu affinity tag, substance P, FLAG peptide (Hopp et al., 1988, *Biotechnology* 6:1204), streptavidin binding peptide, or other antigenic epitopes or binding domains (see, in general, Ford et al., 1991, *Protein Expression and Purification* 2:95).

In some embodiments, the polynucleotide comprises additional coding sequences that encode a plasma membrane anchor domain. For example, a transmembrane polypeptide domain typically comprising a membrane spanning domain (such as an [α]-helical domain) which includes a hydrophobic region capable of energetically favorable interaction with the phospholipid fatty acyl tails that form the interior of the plasma membrane bilayer, or a membrane-inserting domain polypeptide typically comprising a membrane-inserting domain which includes a hydrophobic region capable of energetically favorable interaction with the phospholipid fatty acyl tails that form the interior of the plasma membrane bilayer but that may not span the entire membrane. Well known examples of transmembrane proteins having one or more transmembrane polypeptide domains include members of the integrin family, CD44, glycophorin, MHC Class I and II glycoproteins, EGF receptor, G protein coupled receptor (GPCR) family, receptor tyrosine kinases (such as insulin-like growth factor 1 receptor (IGFR) and platelet-derived growth factor receptor (PDGFR)), porin family and other transmembrane proteins. Certain embodiments of the invention contemplate using a portion of a transmembrane polypeptide domain such as a truncated polypeptide having membrane-inserting characteristics as may be determined according to standard and well known methodologies.

In some embodiments of the invention, the polynucleotide comprises additional coding sequences that encode a specific protein-protein association domain, for example a protein-protein association domain that is capable of specifically associating with an extracellularly disposed region of a cell surface protein or glycoprotein. In certain embodiments, the protein-protein association domain may result in an association that is initiated intracellularly, for instance, concomitant with the synthesis, processing, folding, assembly, transport and/or export to the cell surface of a cell surface protein. In some embodiments, the protein-protein association domain is known to associate with another cell surface protein that is membrane anchored and exteriorly disposed on a cell surface. Non-limiting examples of such domains include, RGD-containing polypeptides including those that are capable of integrin binding (see, for example, Heckmann, D. and Kessler, H., 2007, *Methods Enzymol* 426:463-503 and Takada et al., 2007, *Genome Biol* 8:215).

In some embodiments, the polynucleotide comprises a secretory signal sequence that encodes a secretory peptide. A secretory peptide is an amino acid sequence that acts to direct the secretion of a mature polypeptide or protein from a cell and is generally characterized by a core of hydrophobic amino acids. Secretory peptides are typically, but not exclusively, positioned at the amino termini of newly synthesized proteins. The secretory peptide may be cleaved from the mature protein during secretion and may, therefore, contain processing sites that allow cleavage of the signal peptide from the mature protein as it passes through the secretory pathway. Examples of secretory peptides are known in the art and include, but are not limited to, alpha mating factor leader sequence, the secretory pre-peptide of IL-15, the tissue Plasminogen Activator (tPA) secretory leader peptide, transferrin (Tf) signal sequence, IgE secretory peptides, IgHV and IgKV signal peptides and GM-CSF secretory peptides.

In certain embodiments, sequences encoding transmembrane domain are included in the polynucleotide to provide surface expression of the fusion protein. In some embodiments, the fusion protein is cloned in-frame with a selectable marker to allow for the selection of productive in-frame products. In some embodiments, the polynucleotide comprises sequences encoding transmembrane domain, a selectable marker and an enzyme cleavage site prior to the selectable marker to allow for cleavage of the fusion protein from the transmembrane domain.

Additional sequences, when used, can be included in the polynucleotide by standard genetic engineering techniques such as those described in *Molecular Cloning: A Laboratory Manual* (Third Edition) (Sambrook, et al., ibid.) and *Current Protocols in Molecular Biology* (Ausubel et al. (Ed.), ibid).

Vectors

Certain embodiments of the invention require the use of vectors as cloning and/or expression vehicles. A wide variety of suitable vectors are known in the art and may be employed as described or according to conventional procedures, including modifications, as described for example in Sambrook et al., ibid.; Ausubel et al., ibid., and elsewhere.

One skilled in the art will appreciate that the precise vector used is not critical to the instant invention and suitable vectors can be readily selected by the skilled person. Examples of expression vectors and cloning vehicles include, but are not limited to, viral particles, baculovirus, phage, plasmids, phagemids, cosmids, fosmids, bacterial artificial chromosomes, retrovirus vectors, viral DNA (for example, vaccinia, adenovirus, foul pox virus, pseudorabies and derivatives of SV40), P1-based artificial chromosomes, yeast plasmids, yeast artificial chromosomes, and other known vectors specific for specific host cells of interest.

Large numbers of suitable vectors are known to those of skill in the art, and are many commercially available. Exemplary commercially available vectors include the bacterial vectors: pcDNA (Invitrogen), pQE vectors (Qiagen), pBLUESCRIPT™ plasmids, pNH vectors, lambda-ZAP vectors (Stratagene); ptrc99a, pKK223-3, pDR540, and pRIT2T (Pharmacia); and the eukaryotic vectors: pXT1, pSGS (Stratagene), pSVK3, pBPV, pMSG and pSVLSV40 (Pharmacia). Other vectors include, for example, adenovirus (Ad) vectors (such as, non-replicating Ad5 vectors or replication-competent Ad4 and Ad7 vectors), adeno-associated virus (AAV) vectors (such as, AAV type 5), alphavirus vectors (such as, Venezuelan equine encephalitis virus (VEE), sindbis virus (SIN), semliki forest virus (SFV), and VEE-SIN chimeras), herpes virus vectors, measles virus vectors, pox virus vectors (such as, vaccinia virus, modified vaccinia virus Ankara (MVA), NYVAC (derived from the Copenhagen strain of vaccinia), and avipox vectors: canarypox (ALVAC) and fowlpox (FPV) vectors), and vesicular stomatitis virus vectors. Other suitable plasmids and vectors are known in the art and can readily be selected by the skilled worker. In accordance with various embodiments of the invention, either low copy number or high copy number vectors may be employed.

One skilled in the art will understand that the vector may further include regulatory elements, such as transcriptional elements, required for efficient transcription of the DNA sequence encoding the fusion protein. Examples of regulatory elements that can be incorporated into the vector include, but are not limited to, promoters, enhancers, terminators, alpha-factors, ribosome binding sites and polyadenylation signals.

One skilled in the art will appreciate that selection of suitable regulatory elements is dependent on the host cell chosen for expression of the encoded protein and that such regulatory elements may be derived from a variety of sources, including bacterial, fungal, viral, mammalian or insect genes.

Mammalian expression vectors, for example, may comprise one or more of an origin of replication, any necessary ribosome binding sites, a polyadenylation site, splice donor and acceptor sites, transcriptional termination sequences, and 5' flanking non-transcribed sequences. DNA sequences derived from the SV40 splice and polyadenylation sites, for example, may be used to provide the required non-transcribed genetic elements. Eukaryotic expression vectors may also contain one or more enhancers to increase expression levels of the protein. Enhancers are cis-acting elements of DNA, usually from about 10 to about 300 bp in length that act on a promoter to increase its transcription. Examples include, but are not limited to, the SV40 enhancer on the late side of the replication origin by 100 to 270, the cytomegalovirus early promoter enhancer, the polyoma enhancer on the late side of the replication origin and the adenovirus enhancers.

Examples of typical promoters include, but are not limited to, the bacterial promoters: lad, lacZ, T3, T7, gpt, lambda $P_R$, $P_L$ and trp; and the eukaryotic promoters: CMV immediate early, HSV thymidine kinase, early SV40, late SV40, LTRs from retrovirus and mouse metallothionein-I. Promoter regions can also be selected from a desired gene using chloramphenicol transferase (CAT) vectors or other vectors with selectable markers.

In certain embodiments the vector comprises an expression control sequence which is a "regulated promoter," which may be a promoter as provided herein or may be a repressor binding site, an activator binding site or other regulatory sequence that controls expression of a nucleic acid sequence. In some embodiments, the vector comprises a tightly regulated promoter that is specifically inducible and that permits little or no transcription of nucleic acid sequences under its control in the absence of an induction signal. Examples of such tightly regulated promoters are known in the art and described, for example, in Guzman et al. (1995, *J. Bacteriol.* 177:4121), Carra et al. (1993, *EMBO J.* 12:35), Mayer (1995, *Gene* 163:41), Haldimann et al. (1998, *J. Bacteriol.* 180:1277), Lutz et al. (1997, *NAR.* 25:1203), Allgood et al. (1997, *Curr. Opin. Biotechnol.* 8:474) and Makrides (1996, *Microbiol. Rev.* 60:512). In other embodiments of the invention, the vector comprises a regulated promoter that is inducible but that may not be tightly regulated. Inducible systems that include regulated promoters include, for example, the Tet system or other similar expression-regulating components, such as the Tet/on and Tet/off system (Clontech Inc., Palo Alto, Calif.), the Regulated Mammalian Expression system (Promega, Madison, Wis.), and the GeneSwitch System (Invitrogen Life Technologies, Carlsbad, Calif.).

In certain embodiments, the vector comprises a promoter that is not a regulated promoter; such a promoter may include, for example, a constitutive promoter such as an insect polyhedrin promoter.

In addition, vectors may contain one or more selectable marker genes to provide a phenotypic trait for selection of transformed host cells. Such selectable markers include for example genes encoding dihydrofolate reductase or genes conferring neomycin resistance in eukaryotic host cells, genes conferring ampicillin, chloramphenicol, erythromycin, kanamycin, neomycin or tetracycline resistance in bacterial host cells, and the *S. cerevisiae* TRP1 gene. Promoter regions can be selected from a desired gene using chloramphenicol transferase (CAT) vectors or other vectors with selectable markers. Selectable markers can also include biosynthetic genes, such as those in the histidine, tryptophan and leucine biosynthetic pathways.

In certain embodiments, the vector can have two replication systems to allow it to be maintained in two organisms, for example in mammalian or insect cells for expression and in a prokaryotic host for cloning and amplification.

Also contemplated are replicating and non-replicating episomal vectors for transient expression. The replicating vectors containing origin sequences that promote plasmid replication in the presence of the appropriate trans factors. The SV40 and polyoma origins and respective T-antigens are examples. Also contemplated are stably maintained episomal expression vectors. Episomal plasmids are usually based on sequences from DNA viruses, such as BK virus, bovine papilloma virus 1 and Epstein-Barr virus (see, for example, Van Craenenbroeck, K., et al., 2000, *Eur. J. Biochem.* 267:5665-5678). These vectors contain a viral origin of DNA replication and a viral early gene(s), the product of which activates the viral origin and thus allows the episome to reside in the transfected host cell line in a well-controlled manner. Episomal vectors are plasmid constructions that replicate in both eukaryotic and prokaryotic cells and can therefore also be "shuttled" from one host cell system to another.

In some embodiments the plasmid can be integrated into the host chromosome. Integration can occur by random methods or can be targeted. In some embodiments in which integrating expression vectors are used, the expression vector can contain at least one sequence homologous to the host cell genome, for example, two homologous sequences which flank the expression construct. The integrating vector can thus be directed to a specific locus in the host cell by selecting the appropriate homologous sequence for inclusion in the vector. Constructs and methods for integrating vectors are well known in the art. Alternatively, the use of recombination systems like Cre/Lox and Flp/Frt can be used to target integration. Other methods utilizing zinc-finger proteins as developed by Sangamo Biosciences, Inc. (Richmond, Calif.) provide another approach to targeting vector integration.

In certain embodiments, the methods described herein employ a vector or recombination system that allows for stable integration of the polynucleotide into the host cell genome. In some embodiments, the methods described herein employ a vector or recombination system that allows for stable integration of the polynucleotide into the host cell genome as a single copy.

In certain embodiments of the invention, the vector employed is a viral vector such as a retroviral vector. For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumour virus. Suitable promoters for inclusion in viral vectors include, but are not limited to, the retroviral LTR; the SV40 promoter; and the human cytomegalovirus (CMV) promoter described in Miller, et al. (1989, *Biotechniques* 7:980-990), or other suitable promoter (for example, cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art, and may be from among either regulated promoters or promoters as described above.

In those embodiments that employ a retroviral plasmid vector, the vector is used to transduce packaging cell lines to form producer cell lines. Examples of packaging cells which may be transfected include, but are not limited to, the PE501, PA317, [psi]-2, [psi]-AM, PA12, T19-14X, VT-19-17-H2, [psi]CRE, [psi]CRIP, GP+E-86, GP+envAm12, and DAN cell lines as described in Miller (1990, *Human Gene Therapy,* 7:5-14). The packaging cells may be transduced with the vector using various means known in the art such as, for example, electroporation, the use of liposomes, and CaPO$_4$ precipitation. The producer cell line generates infectious retroviral vector particles which include the polynucleotide encoding the protein. Such retroviral vector particles then may be employed to transduce eukaryotic cells, either in vitro or in vivo, and the transduced eukaryotic cells will express the polynucleotide encoding the protein. Eukaryotic cells which may be transduced include, but are not limited to, embryonic stem cells, embryonic carcinoma cells, hematopoietic stem cells, hepatocytes, fibroblasts, myoblasts, keratinocytes, endothelial cells, and bronchial epithelial cells.

The appropriate DNA or polynucleotide sequences can be inserted into the vector by a variety of procedures known in the art. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Sambrook et al., ibid.; Ausubel et al., ibid., and elsewhere.

The vector can be introduced into a suitable host cell by one of a variety of methods known in the art. Such methods can be found generally described in Ausubel et al. (ibid.) and include, for example, stable or transient transfection, lipofection, electroporation, and infection with recombinant viral vectors. One skilled in the art will understand that selection of the appropriate host cell for expression will be dependent upon the vector chosen. The polynucleotide may stably integrate into the genome of the host cell (for example, with retroviral introduction) or may exist either transiently or stably in the cytoplasm (for example, through the use of traditional plasmids or vectors, utilizing standard regulatory sequences, selection markers, and the like, as described above).

Host Cells

In accordance with the present invention, the host cell employed in the methods described herein is a host cell capable of utilizing recombination signals and undergoing RAG-1/RAG-2 mediated recombination. Accordingly, host cells suitable for use in the methods described herein express or can be engineered to express at least RAG-1 and RAG-2 or functional fragments thereof that allow the host cell to utilize recombination signals and undergo RAG-1/RAG-2 mediated recombination.

In certain embodiments, cell lines to be used as host cells may additionally contain a functional TdT gene. TdT is encoded by a single gene and expresses a nuclear enzyme whose expression in vivo is restricted to lymphoid progenitor cells. TdT has, however, been expressed in non-lymphoid cells and shown to participate in V(D)J recombination using retroviral and transient recombination substrates. TdT has been shown to be expressed as a number of different splice variants, including long form and short form. Certain embodiments of the invention contemplate the use of different isoforms of TdT.

TdT has also been shown to have a 3' to 5' exonuclease activity and the different isoforms of TdT have been shown to have different amounts of exonuclease activity. TdT exonuclease activity can be modulated by substitutions at the conserved aspartic acid residue in the exonuclease motif. In addition, expression of both isoforms was shown to modulate nuclease activity. TdT is highly conserved among species. While mice have two isoforms both human and bovine have three isoforms. In certain embodiments, TdT activity in the host cell can be modulated by altering the levels of TdT in the cell. In some embodiments, mutant forms of TdT or different combinations of isoforms may be used in the host cell to generate coding joints with different extents of deletion and addition.

Recombination-competent host cells may in certain embodiments be pre-B cells or pre-T cells that express RAG-1, RAG-2 and TdT proteins. Such pre-B and pre-T cells may be capable of being induced to express RAG-1, RAG-2 and TdT, or alternatively, may constitutively express RAG-1, RAG-2 and TdT but can be modified to substantially impair the expression of one, two or all three of these enzymes.

In some embodiments, the recombination-competent host cells are non-immune cells that have been transformed with genes encoding each of RAG-1, RAG-2 and TdT. One skilled in the art can readily select an appropriate non-immune host cell. Examples of host cells include, but are not limited to, yeast and mammalian cells. Specific non-limiting examples include green African monkey kidney (COS) cells, NIH 3T3 cells, Chinese hamster ovary (CHO) cells, BHK cells, human embryonic kidney (HEK 293) cells, Huh7.5 human hepatoma cells, Hep G2 human hepatoma cells, Hep 3B human hepatoma cells, HeLa cells and the like.

These and other recombination-competent host cells may be used according to contemplated embodiments of the present invention. For example, expression of RAG1 and/or RAG-2 has been observed in mature B-cells in vivo and in vitro (Maes et al., 2000, *J Immunol.* 165:703; Hikida et al., 1998, *J Exp Med.* 187:795; Casillas et al., 1995, *Mol Immunol.* 32:167; Rathbun et al., 1993, *Int Immunol.* 5:997, Hikida et al., 1996, *Science* 274:2092).

RAG-1 and RAG-2 have also been shown to be expressed in mature T-cell lines including Jurkat T-cells. CEM cells have been shown to have V(D)J recombination activity using extrachromosomal substrates (Gauss et al. 1998, *Eur J Immunol.* 28:351). Treatment of wild-type Jurkat T cells with chemical inhibitors of signaling components revealed that inhibition of Src family kinases using PP2, FK506, and the like, overcame the repression of RAG-1 and resulted in increased RAG-1 expression. Mature T-cells have also been shown to reactivate recombination with treatment of anti-CD3/IL7 (Lantelme et al., 2008, *Mol Immunol.* 45:328).

Tumor cells of non-lymphoid origin have also been shown to express RAG-1 and RAG-2 (Zheng et al., 2007, *Mol Immunol.* 44: 2221, Chen et al., 2007, *Faseb J.* 21:2931). Accordingly, in certain embodiments, these cells may also be suitable for use as recombination-competent host cells in the presently described methods. According to other embodiments that are contemplated herein, reactivation of V(D)J recombination would provide another approach to generating a suitable host cell with inducible recombinase expression.

Alternatively, only one of the RAG-1 or RAG-2 genes may be stably integrated into a host cell, and the other gene can be introduced by transformation to regulate recombination. For example, a cell line that is stably transformed with TdT and RAG-2 would be recombinationally silent. Upon transient transfection with RAG1, or viral infection with RAG-1, the cell lines would become recombinationally active. The skilled person will appreciate from these illustrative examples that other similar approaches may be used to control the onset of recombination in a host cell.

Substantial impairment of the expression of one or more recombination control elements (for example, one or more of a RAG-1 gene, RAG-2 gene or TdT gene) may be achieved by a variety of methods that are well known in the art for blocking specific gene expression, including antisense inhibition of gene expression, ribozyme mediated inhibition of gene expression, siRNA mediated inhibition of gene expression, and Cre recombinase regulation of expression control elements using the Cre/Lox system. As used herein, expression of a gene encoding a recombination control element is substantially impaired by such methods for inhibiting when host cells are substantially but not necessarily completely depleted of functional DNA or functional mRNA encoding the recombination control element, or of the relevant polypeptide. In certain embodiments, recombination control element expression is substantially impaired when cells are at least about 50% depleted of DNA or mRNA encoding the endogenous polypeptide (as detected using high stringency hybridization, for example) or at least about 50% depleted of detectable polypeptide (as measured by Western immunoblot, for example); for example, at least 75% depleted or at least 90% depleted.

Cell lines can also include added genetic elements giving them useful functionality. Invitrogen provides a flp-in system in which the Frt recombination signal is integrated into different host cell lines (3T3, BHK, CHO, CV-1, 293). Equivalent cell lines incorporating LoxP sites or other sites for targeting integration can be used. A tet inducible system (for example, T-Rex from Invitrogen, Carlsbad, Calif.) for 293 or HeLa cell lines or other available inducible systems may also be used.

Screening Assays

The methods according to the present invention may optionally include one or more screening steps, for example, to screen for expression of variant fusion proteins by the host cells and/or to screen for variant fusion proteins having a desired functionality.

In certain embodiments, the methods of the invention comprise screening transformed host cells for expression of variant fusion proteins. Various protein expression assays are known in the art and include the use of UV/VS spectrophotometry, fluorescence spectrophotometry, mass spectrometry and the like. As noted above, in some embodiments, the variant fusion proteins may comprise an additional polypeptide sequence to facilitate detection, for example, by localizing the protein to the cell surface or by incorporating a detectable label.

In certain embodiments in which the variant fusion proteins are not localized to the cell surface or secreted, the expression assay may further comprise a cell lysis step or the protein may be assayed directly within the cell for function.

In certain embodiments, the methods of the invention comprise submitting the variant fusion proteins to a functional assay to identify those variants having a desired functionality. The specific assay used will be dependent on the functionality being assessed. Various functional assays are known in the art and appropriate assays can be readily selected by the skilled worker. Commonly used assays include, for example, ELISA- and FACS-based assays.

The functionality of the variant fusion proteins may be assessed by assaying the cells expressing the variants or the variants may be isolated from the host cells and assayed as isolated proteins.

In some embodiments of the invention, the methods generate high numbers of variant fusion proteins and in such embodiments high throughput screening approaches are generally preferred. Many high throughput screening approaches are well known in the art and can be readily applied to identify and select variant fusion proteins with a desired functionality.

Polynucleotide Compositions

In certain embodiments, the invention provides for polynucleotides capable of undergoing RSS-mediated recombination when introduced into a recombination-competent host cell, and compositions comprising same.

In some embodiments, the polynucleotide is a "bipartite recombination substrate" and preferably comprises: a first nucleic acid sequence including a first coding sequence encoding a first portion of a fusion protein and a first recombination signal sequence (RSS), and a second nucleic acid sequence including a second coding sequence encoding a second portion of the fusion protein and a second RSS capable of functional recombination with the first RSS.

The coding sequences comprised by the bipartite recombination substrate as described above may encode portions of the same protein, for example different domains of the protein, or each may encode all or a portion of a different protein. When the coding sequences encode portions of the same protein, they may when taken together encode the whole protein, or they may encode a truncated or rearranged version of the protein.

In some embodiments, the bipartite recombination substrate may further comprise a linker sequence between the first and second coding sequence with the first and second RSSs positioned within or proximal to the linker sequence, such that when the polynucleotide undergoes RSS-mediated recombination, sequence diversity is introduced into the linker sequence.

In some embodiments, the polynucleotide is a "tripartite recombination substrate" and preferably comprises: a first nucleic acid sequence as described above; a second nucleic acid sequence including a second coding sequence encoding a second portion of the fusion protein, a second RSS capable of functional recombination with the first RSS, and a third RSS; and a third nucleic acid sequence including a third coding sequence encoding a third portion of the fusion protein and a fourth RSS capable of functional recombination with the third RSS.

In certain embodiments, the polynucleotide is a tripartite recombination substrate as described above in which the first and third coding sequences encode portions of the same protein, and the second coding sequence encodes a heterologous sequence that is inserted into the protein, with sequence diversity being generated at both junctions. In some embodiments, the tripartite recombination substrate may further comprise a linker sequence between the first and second coding sequence with the first and second RSSs positioned within or proximal to the linker sequence and/or a linker sequence between the second and third coding sequence with the third and fourth RSSs positioned within or proximal to the linker sequence, such that when the polynucleotide undergoes RSS-mediated recombination, sequence diversity is introduced into the linker sequence(s).

In certain embodiments, the polynucleotide is a tripartite recombination substrate as described above in which all three coding sequences encode portions of the same protein, for example different domains of the protein. In this case, the three coding sequences taken together may encode the whole protein, or may encode a truncated or rearranged version of the protein. In some embodiments, the polynucleotide is a tripartite recombination substrate as described above in which two of the three coding sequences encode portions of the same protein, for example different domains of the protein. Embodiments in which the tripartite recombination substrate comprises three coding sequences each from a different protein, for example each encoding a domain or polypeptide, are also contemplated.

In some embodiments, the polynucleotide is a tripartite recombination substrate as described above in which the first and third coding sequences encode portions of an antibody variable region, and the second coding sequence encodes a heterologous sequence that is inserted into the antibody variable region, for example into CDR1, CDR2 or CDR3, with sequence diversity being generated at both junctions. In some embodiments, the polynucleotide is a tripartite recombination substrate as described above in which the first and third coding sequences encode portions of an non-Ig protein, and the second coding sequence encodes a heterologous sequence that is inserted into the protein.

In some embodiments, the polynucleotide comprises RSSs that are accompanied by flanking sequences adjacent to one or both of the heptamers of the RSS. In some embodiments, the polynucleotide comprises RSSs that are accompanied by flanking sequences that encode a specific amino acid, or amino acids, or peptide sequence.

The polynucleotide compositions may be provided as isolated polynucleotides or they may be provided as part of a vector, in which case they may be operatively linked to one or more regulatory elements, such as, promoters, enhancers, terminators, alpha-factors, ribosome binding sites, polyadenylation signals and the like, as described above. The present invention also contemplates that the compositions may be provided as host cells that have been transformed with the polynucleotide or a vector comprising the polynucleotide. Examples of suitable host cells include those described above.

Applications

In accordance with one aspect of the present invention, the methods can be used to generate variants of a fusion protein, for example fusion proteins having a desired functionality or in which one or more of the components of the fusion protein have an improved or optimized functionality. In certain embodiments, the methods are employed to generate a large number of variants of the fusion protein for subsequent screening for a desired or improved functionality.

In certain embodiments, the methods are used to generate modified protein scaffolds that include a heterologous amino acid sequence that provides a new functionality to the protein scaffold, for example, a ligand-binding functionality. In some embodiments, the methods are used to generate variants of a fusion protein that comprise two different proteins or protein domains joined by a linker in which sequence diversity is introduced into the linker in order to optimize the functionality of one or both of the components of the fusion protein.

In some embodiments, the methods are used to graft non-antibody sequences (for example, a protein domain or polypeptide) into an antibody CDR and identify the appropriate sequence context (length and composition) that allows the protein domain or polypeptide to remain functional within the context of the antibody scaffold.

In certain embodiments, the methods of the invention are used to insert large protein domains into a heterologous coding sequence, such as a protein scaffold, and retain biological function. In some embodiments, the methods use flanking sequences next to the heptamer of one or more of the RSSs such that an inserted protein domain is allowed to maintain an appropriate confirmation for functionality within the heterologous protein scaffold.

In certain embodiments, the invention provides for the use of the methods for peptide grafting to generate fusion proteins with ligand-binding properties (for example, modified antibodies, avimers, adnectins, or other antibody mimetics) for therapeutic purposes, for diagnostic purposes, for drug targeting (for example, through the use of a ligand-binding protein that targets a protein on a particular cell or tissue type as a targeting moiety for attachment to a therapeutic or diagnostic compound), or for research applications (such as screening assays, chromatography and the like).

Peptide-Grafted Immunoglobulins

Certain embodiments of the invention relate to peptide-grafted immunoglobulins in which one or more peptides of interest having optimized flanking sequences have been grafted into one or more CDRs of an immunoglobulin. In certain embodiments, the peptide(s) comprised by the peptide-grafted immunoglobulins are targeted to a receptor. In some embodiments, the peptide(s) comprised by the peptide-grafted immunoglobulins are targeted to a receptor from a clinically relevant receptor class, such as a GPCR or ion channel. Such receptors have historically been difficult to target. As demonstrated herein, it is possible to graft peptides with reactivity to a GPCR into the CDRs of a full length human IgG scaffold and retain the ability of the peptide(s) to bind their target thus demonstrating that peptide-grafted immunoglobulins can be used successfully to target these complex membrane proteins.

Certain embodiments of the invention thus relate to peptide-grafted immunoglobulins that comprise one or more peptides targeted to a GPCR. GPCRs are classified into six families: the rhodopsin family (A), the secretin-receptor family (B), the metabotropic glutamate receptor family (C), fungal pheromone P- and α-factor receptors (D), fungal pheromone A- and M-factor receptors (E) and cyclic-AMP receptors from Dictyostelium (F). Peptide-grafted immunoglobulins that comprise one or more peptides targeted to a GPCR from any one of these families are contemplated in various embodiments of the invention. In certain embodiments, the peptide-grafted immunoglobulins comprise one or more peptides targeted to a Family B GPCR.

Suitable peptides for targeting a GPCR may be derived from, for example, a known natural or synthetic ligand. Peptides may also be derived from snake venom peptides, or toxic peptides from other organisms, which are small and contain a loop structure, and are thus suitable for CDR grafting.

In some embodiments, the invention relates to peptide-grafted immunoglobulins comprising one or more peptides targeted to the GLP-1 receptor. Suitable peptides include those derived from GLP-1 and from exendin-4. Non-limiting examples of appropriate targeting peptides and flanking sequences are provided in Example 10 (see Tables 5 and 6).

The immunoglobulin scaffold may be a full-length immunoglobulin (such as a full-length IgA, IgA2, IgD, IgE, IgGs (i.e. IgG1, IgG2, IgG3 or IgG4) or IgM) or an immunoglobulin fragment (such as a Fab, Fab', F(ab')$_2$, Fd, Fv and single-chain Fv (scFv) fragment). Certain embodiments of the invention relate to peptide-grafted immunoglobulins in which the immunoglobulin scaffold is a full-length IgG immunoglobulin.

Immunoglobulins suitable for use in the methods described herein may be derived from a variety of sources and technologies including, but not limited to, mammals including mice, transgenic mice and humans, phage display or yeast display, or they may be synthetically derived immunoglobulins or fragments thereof.

Certain embodiments of the invention contemplate the use of immunoglobulin scaffolds from camelid antibodies; HCAns; single chain antibodies; shark antibodies; diabodies; nanobodies and fluorobodies.

The peptide(s) may be grafted into a heavy chain CDR or a light chain CDR or both. In some embodiments, the peptide(s) may be grafted into a heavy chain CDR3 or a light chain CDR3 or both. In certain embodiments, the peptide is grafted into at least a heavy chain CDR. In some embodiments, the peptide replaces the D segment in the heavy chain CDR3.

Optimization of the flanking sequences may be achieved using the methods described above, or by other methods described in the art. For example, gene synthesis can be used to synthesize a V gene segment utilizing degenerate nucleotides in selected positions flanking the peptide encoding sequence. The synthesis of V gene segments with different lengths of flanking sequences in combination with degenerate nucleotides results in both sequence length and composition differences flanking the peptide. These peptide-grafted immunoglobulin variable gene sequences can be cloned and manipulated by any of a variety of methods known in the art for screening or selection, such as phage display, yeast display, or transfection or infection of mammalian cell lines.

Another method for generating libraries of peptide-grafted immunoglobulin variants includes cloning utilizing oligonucleotides. The V and/or J gene sequences and peptide encoding DNA sequences can cloned together utilizing different oligonucleotide adapters that contain different amino acid sequences and are designed to ligate and join the variable sequences to the peptide encoding DNA sequences. The oligonucleotides can also differ in length and a large set of oligonucleotides can be generated that represent different lengths and compositions of amino acids. Cloning these pools of oligonucleotides in between the VH gene segment and the DNA sequences encoding the peptide will generate novel fusions differing in both length and composition. Techniques utilizing trinucleotide mutagenesis have also been described.

Another method to generate libraries of peptide-grafted immunoglobulin variants utilizes PCR. PCR-based cloning can also be employed to generate amino acid diversity of length and composition between the V and/or the J gene segment. Primers annealing to the peptide encoding sequence can be designed to include degenerate oligonucleotides. The use of degenerate flanking sequences on both the forward and reverse primers will generate a mixture of PCR fragments containing the peptide encoding sequences and a diversity of flanking sequences. PCR primers can be designed with different lengths of flanking sequences. The PCR products are then cloned in between a variable and joining gene segment to generate a library of peptide grafted antibody variable chain variants.

These above techniques can also be combined. Other techniques are known in the art, including site-directed mutagenesis that would target diversity to the flanking nucleotide sequences, or the use of error-prone PCR.

Typically the peptide will comprise both an upstream (i.e. C-terminal) and a downstream (i.e. N-terminal) flanking sequence, although embodiments in which only one of an upstream or a downstream flanking sequence is present are also contemplated. Flanking sequences may be between about 1 and about 30 amino acids in length, for example, between about 2 and about 30 amino acids in length, between about 1 and about 25 amino acids, between about 2 and about 25 amino acids, between about 1 and about 20 amino acids, between about 2 and about 20 amino acids, between about 1 and about 15 amino acids in length, between about 2 and about 15 amino acids in length, or any amount therebetween, for example 1, 2, 3, 4, 5, 6, 7, 8, 9, 10 or more amino acids in length. The upstream and downstream flanking sequences may be the same length or may be different lengths.

In some embodiments, the peptide-grafted immunoglobulins are initially identified by employing the methods of the present invention to graft the peptide into the immunoglobulin scaffold and to optimize the flanking sequences. Certain embodiments of the invention thus relate to the use of the methods described herein that employ components of the V(D)J recombination system to generate the above-described peptide-grafted immunoglobulins. Once an active peptide-grafted immunoglobulin has been thus identified, it may be sequenced and additional quantities of the molecule prepared by standard molecular biology and protein purification techniques. Further optimization of the peptide-grafted immunoglobulin using the methods described herein is also contemplated in certain embodiments.

Kits

Certain embodiments of the invention provide for kits comprising a polynucleotide capable of undergoing RSS-mediated recombination when introduced into a recombination-competent host cell, or a composition comprising a polynucleotide capable of undergoing RSS-mediated recombination when introduced into such a host cell, as described above.

When the kit comprises a composition, the composition may comprise an isolated polynucleotide, a polynucleotide comprised by a vector (in which case the polynucleotide may be operatively linked to one or more regulatory elements, such as, promoters, enhancers, terminators, alpha-factors, ribosome binding sites, polyadenylation signals and the like), or a host cell that has been transformed with the polynucleotide or a vector comprising the polynucleotide.

When the kit comprises an isolated polynucleotide, the kit may further comprise a vector suitable for expression of the polynucleotide and/or a recombination-competent host cell.

The kit may further comprise vectors encoding one or more of RAG-1, RAG-2 and TdT that are suitable for transforming a host cell such that the host cell expresses, or is capable of expressing, RAG-1, RAG-2 and/or TdT.

The kit may further comprise one or more additional components to assist with cloning the polynucleotide and/or transformation of host cells, such as buffers, enzymes, selection reagents, growth media and the like.

One or more of the components of the kit may optionally be lyophilised and the kit may further comprise reagents suitable for the reconstitution of the lyophilised components.

Individual components of the kit would be packaged in separate containers and, associated with such containers, can be instructions for use. The instructions for use may be provided in paper form or in computer-readable form, such as a disc, CD, DVD or the like.

To gain a better understanding of the invention described herein, the following examples are set forth. It will be understood that these examples are intended to describe illustrative embodiments of the invention and are not intended to limit the scope of the invention in any way.

EXAMPLES

Example 1: Construction of a Fusion Protein Grafting Acceptor Vector

A vector was designed to allow a selected amino acid sequence to be grafted into the variable region of an antibody heavy chain. A schematic of the vector is shown in FIG. 1A and the nucleotide sequence [SEQ ID NO:28] is provided in FIG. 1(B).

The vector comprises a stuffer sequence between two BsmBI restriction sites, with an upstream $V_H$ sequence and 23 bp RSS and a downstream 23 bp RSS and $J_H$ sequence operably linked to the IgG1 constant region. The vector is designed to accept a nucleic acid sequence encoding the selected amino acid sequence flanked by 12 bp RSSs. The locations of the various components of the vector are provided in Table 2 below.

Additional details are provided in Example 9, together with an exemplary method for transfection of a recombination substrate into a recombination-competent host cell, expansion of the host cell and recombination and expression of the substrate.

TABLE 2

Location Of Components Of The Fusion Protein Grafting Acceptor Vector Within SEQ ID NO: 28

| Component | Location |
|---|---|
| CMV promoter | 1-621 |
| VH3-33 | 663-1015 |
| Flanking sequences (optional) | 1016 |
| 23 bp-RSS | 1016-1054 |
| Intervening sequence #1 | 1055-1608 |
| BsmBI site #1 | 1609-1614 |
| Stuffer sequences | 1615-3556 |
| BsmBI site #2 | 3557-3562 |
| Intervening sequences #2 | 3563-4159 |
| 23 bp-RSS | 4160-4198 |
| Flanking sequences (optional) | 4199 |
| JH4 | 4199-4246 |
| Spice donor-intron-splice acceptor | 4247-4541 |
| CH1-hinge-CH2CH3 | 4542-5530 |
| Transmembrane sequence | 5531-5596 |
| Cytoplasmic sequence | 5597-5698 |

Example 2: Grafting RGD from Fibronectin Type III 10 into an Antibody Scaffold The grafting of RGD from fibronectin type III 10 into an antibody scaffold using the V(D)J in vitro system will be conducted as follows.

The RGD sequence is derived from fibronectin and is flanked by 12 bp RSSs and BsmBI sites (SEQ ID NO:29, below) and placed into the acceptor vector described in Example 1 to generate a recombination substrate for generating a library of variant fusion proteins.

Nucleotide sequence of RGD peptide #1 (61 bp; 20 amino acids; in capitals) flanked by 12 bp RSSs and BsmBI sites. Nucleotides encoding "RGD" in bold.

[SEQ ID NO: 29]
cgtctctccaagtgcaaagggacaggaggttttttgttaagggctgta tcactgtgTATACCATCACTGTGTATGCTGTCACTGGCCGTGGAGAC

AGCCCCGCAAGCAGCAAGCCAATTTCCATTcacagtgatacagccct taacaaaaaccccctactgcaacctggcggtaagagacg Nucleotide sequence of RGD peptide #1 (61 bp)

[SEQ ID NO: 30]
TATACCATCACTGTGTATGCTGTCACTGGCCGTGGAGACAGCCCCGC

AAGCAGCAAGCCAATTTCCATT

Amino acid sequence of RGD peptide #1 (20 amino acids) [SEQ ID NO:31].
YTITVYAVTGRGDSPASSKPISI Nucleotide sequence of RGD peptide #2 (39 bp; 13 amino acids; in capitals) flanked by 12 bp RSSs and BsmBI sites. Nucleotides encoding "RGD" in bold.

[SEQ ID NO: 32]
cgtctctccaagtgcaaagggacaggaggttttttgttaagggctgta tcactgtgTATGCTGTCACTGGCCGTGGAGACAGCCCCGCAAGCAGC cacagtgatacagcccttaacaaaaaccccctactgcaacctggcggt aagagacg Nucleotide sequence of RGD peptide #2 (39 bp)

[SEQ ID NO: 33]
TATGCTGTCACTGGCCGTGGAGACAGCCCCGCAAGCAGC

Amino acid sequence of RGD peptide #2 (13 amino acids)

[SEQ ID NO: 34]
YAVTGRGDSPASS

The fibronectin sequences can be modified so that an RGD peptide sequence is created in all three reading frames. The modified fibronectin sequence is shown below.

[SEQ ID NO: 35]
TATACCATCACGTGGAGACCTGTGTATGCTGTCACTGGCCGTGGAG

ACAGCCCCGCGGAGACAAGCAGCAAGCCAATTTCCATT

The three reading frames with the RGD sequences are shown in FIG. 2 [SEQ ID NOs:9-11].

The acceptor vector with a selected RGD peptide construct is co-integrated into a cell line with a kappa light chain. The cell line is selected for light chain expression and the ability to recombine the integrated substrate. The cell line is then expanded in the unrecombined state and V(D)J recombination is induced to generate a library of greater than 10 million cells each expressing a unique fusion protein on the cell surface. The cell library is then incubated with soluble form of biotinylated alphaVBeta5 integrin and avidin-conjugated fluorochrome, and FACS sorted to isolate fusion proteins with integrin binding properties.

Example 3: Grafting G-Protein Coupled Receptor Ligands into an Antibody Scaffold G protein-coupled receptors (GPCRs) are a family of integral transmembrane proteins thought to have the same molecular architecture, consisting of seven transmembrane domains (7TM), three extracellular loops (EC1, EC2, EC3), three intracellular loops (IC1, IC2, and IC3), an amino-terminal extracellular domain and an intracellular carboxyl terminus. This topology is predicted from the analysis of hydropathy profiles and from a limited amount of experimental evidence, most importantly from the crystal structure rhodopsin GPCRs were classified into six families: the rhodopsin family (A), the secretin-receptor family (B), the metabotropic glutamate receptor family (C), fungal pheromone P- and α-factor receptors (D), fungal pheromone A- and M-factor receptors (E) and cyclic-AMP receptors from Dictyostelium (F). Although many anti-GPCR antibodies have been generated it is generally appreciated that GPCRs are difficult targets to generate neutralizing antibodies. This Example will utilize domain grafting of sequences derived from GPCR ligands to engineer anti-GPCR specificity and antibodies with desired activities.

Peptide sequences derived from glucagon-like peptide-1 (GLP-1) and Exendin-4 are used to generate fusion proteins targeting GLP-1R, a receptor belonging to the B1 family of seven-transmembrane G protein-coupled receptors. GLP-1 is a peptide hormone generated in intestinal L-cells that binds to GLP-1R on pancreatic beta-cells and potentiates the synthesis and release of insulin in a glucose-dependent manner. Exendin-4 is a peptide hormone found in the saliva of the Gila monster. It is a GLP-1R agonist that binds to the receptor with an affinity and potency similar to GLP-1.

Two versions of GLP-1 have been selected to generate fusion proteins. The first version is based on the complete hormone sequence (amino acids 7-37). A second version is based on a truncated form of GLP-1 that spans amino acids 13-33. This region has been found to assume an alpha-helical confirmation when bound to GLP-1R and includes several residues important for receptor binding. Schematic representations of a cassette comprising each sequence together with appropriate 12 bp RSS sequences, as well as the respective nucleotide sequences [SEQ ID NOs:36 and 37] and amino acid sequences [SEQ ID NOs:38 and 39] for the cassettes are provided in FIG. 3.

Fusion proteins will be generated from three forms of exendin-4. The first version is based on all 39 amino acids of the natural peptide. The second version is based on amino acids 9-39. This truncated form of exendin-4 is a competitive antagonist that binds to GLP-1R with high affinity. The third version was based on residues 15-27. This region is believed to form the most critical interactions with GLP1R. Schematic representations of a cassette comprising each sequence together with appropriate 12 bp RSS sequences, as well as the respective nucleotide sequences [SEQ ID NOs: 40, 41 and 42] and amino acid sequences [SEQ ID NOs:43, 44 and 45] for the cassettes are provided in FIG. 4.

The nucleic acid sequences encoding the peptides will be codon optimized and stop codons introduced into the other non-relevant reading frames. The bolded sequences in FIGS. 3 and 4 represent the specific nucleic acid sequences encoding the appropriate peptide. The sequences are gene synthesized as a cassette that includes flanking BsmBI sites and 12 bp RSS sequences as shown. The BsmBI sites are used to clone the RSS-peptide-RSS cassette into the acceptor vector described in Example 1.

Example 4: Peptide Grafting to Generate an Anti-CXCR1 Binding Antibody

This example utilizes sequences from IL-8, Gro-alpha and LL-37 (which are all ligands that bind CXCR1) to generate an antibody with anti-CXCR1 specificity. Each of the peptides described below can be generated as a cassette including flanking BsmBI sites and 12 bp RSS sequences as described above for the RGD and GLP-1 sequences.

The canonical chemokine CXCL8 (IL-8) (Nucleotide Accession: NM_000584) is a member of the CXC chemokine family. This chemokine is one of the major mediators of the inflammatory response. This chemokine is secreted by several cell types. It functions as a chemoattractant, and is also a potent angiogenic factor. IL-8 binds with high affinity to two highly homologous chemokine receptors CXCR1 and CXCR2, which mediate pleiotropic responses including the onset of inflammation, angiogenesis, tumorogenesis and wound healing. The CXCR1 and CXCR2 receptors are GPCRs. The chemokines are folded into three anti-parallel b-sheets and a helix on the top, with an unstructured N-terminus containing the ELR triad, and the CXC motif which connects the ELR to the N-loop and the 30 s loop. On the basis mutagenesis and structural studies of chemokines and their cognate receptors, a two-site model is postulated for the interactions of chemokines with their cognate receptors. Site 1 includes the receptor N-terminus, which recognizes the N-loop of chemokines, and site 2 includes extracellular loops of the receptor for binding to the N-terminus of chemokines to trigger receptor activation.

The amino acids involved in IL-8 binding to its receptor have been identified. Antibodies that neutralize IL-8 activity have been mapped to the ELRCXC sequences in the IL-8 protein. This Example utilizes sequences from this region of the IL-8 molecule as a peptide for grafting into an Ig scaffold to generate an anti-CXCR1 specific antibody. The use of sequences from the N-loop would also serve as potential sources for IL-8 based domain grafting. Other ligands that bind to CXCR1, such as Gro-alpha and LL-37, are also sources for peptide grafting. In some cases the sequences are engineered so that stop codons are introduced into the other reading frames.

The IL-8 nucleotide and amino acid sequences [SEQ ID NOs:46 and 47, respectively] are provided in FIG. 5(A). The sequence that will be used for peptide grafting is shown in FIG. 5(B) [SEQ ID NO:12].

CXCL1, Gro-alpha, is also a ligand for CXCR2. The binding domain as been identified as: ATELRCQCLQTLQGIHPKNIQSV [SEQ ID NO:48] (also shown in FIG. 5(C)).

The sequence that will be used for peptide grafting is shown in FIG. 5(D) [SEQ ID NO:49].

LL-37 has also been shown to bind to CXCR2. A silent substitution of (G>A) places a stop codon in reading frame #2:

```
                                        [SEQ ID NO: 50]
CTGCTAGGTGATTTCTTCCGGAAATCTAAA
```

(also see FIG. 5(E)).

Example 5: ErbB Receptor Peptides for Peptide Grafting

The source of sequences for peptide grafting is not limited to ligands. This Example identifies regions of the ErbB receptor (a member of the EGF receptor family) that are suitable for grafting into a protein scaffold using the methods of the present invention.

ErbB receptor extracellular regions all contain four distinct domains Domains I, II, III and IV. Domains II and IV are referred to as cysteine rich domains (CRI and CRII). During receptor dimerization all intermolecular contacts are mediated by the receptors. Current models for receptor dimerization suggest that ErbB family members adopt a tethered closed configuration in which loops from CRI and CRII form a structure in which the dimerization arm in CRI is occluded. Upon ligand binding the receptor forms an open configuration in which the dimerization arm in CRI is now exposed and free to engage the dimerization loop on an adjacent receptor thus forming an ErbB dimer. ErbB2 does not have a ligand and its structure is found to be in an untethered form constitutively. Alignment of various ErbB sequences showing the dimerization arm are shown in FIG. 6 [SEQ ID NOs:13-16].

As a way to target HER2 and EGFR receptors, receptor-receptor interacting domains can be used to direct the binding of a fusion protein. In the case of HER2, domains can be generated using the receptor dimerization arm. For EGFR receptor the dimerization arm as well as the inhibition domain in Cysteine Rich Domain 2 (CR2) of the Extracellular Domain (CR1IVc and CRIVd) can be used. Given that EGFR forms a closed "tethered" structure, the domains for the EGFR may only bind receptor when the receptor is in the untethered form, which may allow the untethered form of EGFR to be specifically targeted, which in turn could provide the antibody with a unique clinically useful specificity in targeting diseases associated with over-expression of EGFR and its variants.

Sequences of peptides from ErbB2 selected for grafting into the vector described in Example 1 are provided below. The BsmBI sites and RSSs are not shown but would be generated as described in the previous Examples as gene synthesized cassettes for cloning into the appropriate acceptor vector.

Peptide #1 (V981)

This peptide contains the ErbB2 dimerization arm. Stop codons are present in alternative forward frames. Stops in an inverted orientation are present in one out of the 3 frames.

Nucleotide Sequence:

[SEQ ID NO: 51]
TGCCCAGCCCTGGTAACCTACAACACAGACACGTTTGAGTCCATGCC

CAATCCCGAGGGCCGGTATACATTCGGCGCCAGCTGT

Amino Acid Sequence:

[SEQ ID NO: 52]
CPALVTYNTDTFESMPNPEGRYTFGASC

Peptide #2 (V982)

This peptide contains the ErbB2 dimerization arm with additional endogenous sequences flanking the cysteine residues as a means to ensure that a larger portion of the fusion proteins will contain these residues. Stop codons are present in alternative forward frames. Stops in an inverted orientation are present in 1 out of the 3 frames.

Nucleotide Sequence:

[SEQ ID NO: 53]
CTGCACTGCCCAGCCCTGGTAACCTACAACACAGACACGTTTGAGTCCAT

GCCCAATCCCGAGGGCCGGTATACATTCGGCGCCAGCTGTGTGACT

Amino Acid Sequence:

[SEQ ID NO: 54]
LHCPALVTYNTDTFESMPNPEGRYTFGASCVT

Peptide #3 (V983)

This peptide contains the ErbB1 dimerization arm. Stop codons are present in one of the alternative forward frames. Stops in an inverted orientation are present in 2 out of the 3 frames.

Nucleotide Sequence:

[SEQ ID NO: 55]
TGCCCCCCACTCATGCTCTACAACCCCACCACGTACCAGATGGATGTGAA

CCCCGAGGGCAAATACAGCTTTGGTGCCACCTGC

Amino Acid Sequence:

[SEQ ID NO: 56]
CPPLMLYNPTTYQMDVNPEGKYSFGATC

Peptide #4 (V984)

This peptide contains two loops from the CRII. These domains bind to the dimerization loop in CRI in the tethered configuration. Upon ligand binding, these loops potentially may form intermolecular contacts with the same loop in another untethered ErbB receptor. Fusion proteins containing this domain could thus potentially bind to CRI or CRII domains of untethered ErbB receptors.

Stops are present in this peptide in alternative forward frames and in 2 of the 3 reverse frames.

Nucleotide Sequence:

[SEQ ID NO: 57]
TGTGCCCACTACATTGACGGCCCCCACTGCGTGAAGACCTGCCCGGCAGG

AGTCATGGGTGAAAACAACACCCTGGTCTGGAAGTACGCAGACGCCGGCC

ATGTGTGC

Amino Acid Sequence:

[SEQ ID NO: 58]
CAHYIDGPHCVKTCPAGVMGENNTLVWKYADAGHVC

Peptide #5 (V985)

This domain contains the 5' loop in CRII (first loop of peptide #4). As with peptide #4, this domain binds to the dimerization loop in CRI in the tethered configuration and fusion proteins containing the domain represented by peptide #5 could thus also potentially bind to CRI or CRII domains of untethered ErbB receptors.

Nucleotide Sequence:

[SEQ ID NO: 59]
TGTGCCCACTACATTGACGGCCCCCACTGC

Amino Acid Sequence:

[SEQ ID NO: 60]
CAHYIDGPHC

Peptide #6 (V986)

This domain contains the 3' loop in CRII (second loop of peptide #4). As with peptide #4, this domain binds to the dimerization loop in CRI in the tethered configuration and fusion proteins containing the domain represented by peptide #6 could thus also potentially bind to CRI or CRII domains of untethered ErbB receptors.

Nucleotide Sequence:

[SEQ ID NO: 61]
TGCCCGGCAGGAGTCATGGGAGAAAATAACACCCTAGTCTGGAAGTACGC

AGACGCCGGCCATGTGTGC

Amino Acid Sequence:

[SEQ ID NO: 62]
CPAGVMGENNTLVWKYADAGHVC

Example 6: Preparation of Constructs for Introducing Sequence Diversity into a Fibronectin Domain The methods of the present invention can also be used to graft peptides into non-Ig scaffolds or to join two non-Ig sequences or a non-Ig sequence and an Ig sequence. This Example demonstrates the principle of using V(D)J in a non-Ig context. The same peptides identified in the preceding Examples 2-5 can be introduced into the 10Fn3 loop. The same method described below is used for Ig and non-Ig peptide grafting using V(D)J. An exemplary acceptor vector for grafting peptides into the 10Fn3 loop is shown in FIG. 7. Both this vector and the acceptor vector shown in FIG. 1 allow easy manipulation of the flanking sequences of the 12 RSSs. Similar vectors can be constructed to allow easy manipulation of the flanking sequences of the 23 bp RSSs.

Example 7: Recombination and Expression of a Recombination Substrate

In brief, HEK293 cells, containing an integrated LoxP sequence (Fukushige et al., 1992, PNAS USA, 89:7905-7909; Baubonis et al., 1993, NAR, 21(9):2025-2029; Thomson et al., 2003, Genesis, 36:162-167) were maintained in DMEM media with 10% FBS. Integration into the LoxP site was shown to support high protein expression and also support V(D)J recombination of inserted substrates and provides an easy method to generate integrants with the required properties. Vectors comprising the recombination substrate were designed to include a LoxP site for targeted integration which is in-frame with a codon-optimized hygromycin open reading frame. Bipartite vectors were also designed so that productive rearrangements will be in-frame with the selectable marker neomycin. The neomycin gene is cloned in-frame with a transmembrane domain, both of which are downstream of a furin cleavage site that allows for secretion of the encoded protein (see FIG. 9 and SEQ ID NO:64, as an example).

For example, for bipartite substrates, HEK293 cells containing the LoxP site were co-transfected with the bipartite substrate containing the hygromycin gene for selection of stable integrants and a vector expressing the CRE protein at a ratio of 10:1 substrate to CRE expressing vector. Specifically, a 10 cm dish of cells was transfected using a polyethylenimine (PEI; 1 mg/ml) to DNA ratio of 3:1. 21.6 ug of substrate DNA was mixed with 2.4 ug of CRE expression vector and placed in 1.5 ml OptiMEM™ media and mixed with an equal volume of OptiMEM™ containing the 72 ul of PEI. The transfection was carried out for 24 hours and the following day the transfection media was removed and replaced with fresh DMEM media. The following day the transfected cells were split into ten 10 cm² dishes and selection was carried out for approximately 2 weeks. A pool of stable hygromycin resistant cells were selected. The cell line was subsequently expanded in the un-recombined state to approximately 10 million cells and transfected with RAG-1, RAG-2 and TdT. 72 hours post-transfection the cells were placed in neomycin selection (1 mg/ml).

Tripartite recombination substrates used vectors designed such that puromycin could be used for in-frame selection. Tripartite vectors also included a modified neomycin cassette that allows for maintenance of the unrecombined substrate during expansion.

Example 8: Preparation of Immunoglobulins Grafted with an Anti-TPO Receptor Peptide Full length human IgGs comprising a peptide targeted to the TPO receptor (shown below) were prepared using a recombination substrate comprising the cassette shown in FIG. 11A, which includes 5' and 3' flanking sequences that include degenerative nucleotide combinations to generate diversity at the ends in addition to the diversity that is generated via V(D)J recombination. The flanking VH gene segment in the recombination substrate was VH1-69 and the flanking JH segment was JH6.

Anti-TPO receptor peptide: IEGPTLRQWLAARA [SEQ ID NO:71]

Cells incorporating a tripartite V(D)J recombination substrate containing the recombination cassette shown in FIG. 11A were cultured and induced to generate peptide grafted variants as described in the preceding Examples. V(D)J recombined cells expressing the peptide-grafted antibodies were incubated with biotinylated TPO receptor (R&D Systems). The cells were subsequently stained with Streptavidin-PE to identify cells that had successfully bound the receptor and FACS sorted. cDNA from the FACS sorted cells were subsequently cloned into pcDNA to express the novel antibody as a full length IgG containing a transmembrane domain.

Amino acid and nucleotide sequences of the peptide and flanking sequences, for exemplary peptide-grafted immunoglobulins isolated by this approach that were shown to bind to the TPO receptor are shown in Tables 3 and 4 below. In each case, the VH and JH segments utilized were IGHV1-69*01 and IGHJ6, respectively.

TABLE 3

Amino Acid Sequences of Anti-TPO Receptor Peptides and Flanking Sequences [SEQ ID NOs: 19-25]

| | CDR3 AA Sequence | | | |
|---|---|---|---|---|
| | 5' FLANK | Sequences incorporated from anti-TpoR peptide | 3' FLANK | SEQ ID NO |
| Anti-TpoR 1 | ARDLVD | IEGPTLRQWLAARA | HGREYYYYYMDV | 19 |
| Anti-TpoR 2 | ARDPTLWL | IEGPTLRQWLAARA | EYYYYYYMDV | 20 |
| Anti-TpoR 3 | AGPLR | IEGPTLRQWLAARA | SLYYMDV | 21 |
| Anti-TpoR 4 | ARAKSSQ | IEGPTLRQWLAARA | ELRLQHYYMDV | 22 |

TABLE 4-continued

Nucleotide Sequences of Anti-TPO Receptor Peptides and Flanking Sequences [SEQ ID NOs: 26, 27 and 81-85]

| | Variable Gene Nucleotide Sequences (Heavy Chain) | SEQ ID NO |
|---|---|---|
| Anti-TpoR 5 | CAGGTGCAGCTGGTGCAGTCTGGCGCCGAAGTGAAGAAA CCCGGCAGCAGCGTGAAGGTGTCCTGCAAGGCCAGCGGC GGCACCTTCAGCAGCTACGCCATCAGCTGGGTCCGCCAG GCTCCTGGACAGGGACTGGAATGGATGGGCGGCATCATC CCCATCTTCGGCACCGCCAAATACGCCCAGAAATTCCAG GGCAGAGTGACCATCACCGCCGACGAGAGCACCAGCACC GCCTACATGGAACTGAGCAGCCTTCGAAGCGAGGACACC GCTGTGTATTACTGTGCGAGGAAGCCGCAGGCTATCGAG GGCCCTACCCTGAGACAGTGGCTGGCCGCTAGAGCTCTG GGAAACTACTACATGGACGTCTGGGGCAAAGGGACCACG GTCACCGTGTCCTCAG | 83 |
| Anti-TpoR 6 | CAGGTGCAGCTGGTGCAGTCTGGCGCCGAAGTGAAGAAA CCCGGCAGCAGCGTGAAGGTGTCCTGCAAGGCCAGCGGC GGCACCTTCAGCAGCTACGCCATCAGCTGGGTCCGCCAG GCTCCTGGACAGGGACTGGAATGGATGGGCGGCATCATC CCCATCTTCGGCACCGCCAACTACGCCCAGAAATTCCAG GGCAGAGTGACCATCACCGCCGACGAGAGCACCAGCACC GCCTACATGGAACTGAGCAGCCTTCGAAGCGAGGACACC GCTGTGTATTACTGTGCGAGAACGTTGCGTATCGAGGGC CCTACCCTGAGACAGTGGCTGGCCGCTAGAGCTCCGGCG GCCTACTACTACTACATGGACGTCTGGGGCAAAGGG ACCACGGTCACCGTGTCCTCAG | 84 |
| Anti-TpoR 7 | CAGGTGCAGCTGGTGCAGTCTGGCGCCGAAGTGAAGAAA CCCGGCAGCAGCGTGAAGGTGTCCTGCAAGGCCAGCGGC GGCACCTTCAGCAGCTACGCCATCAGCTGGGTCCGCCAG GCTCCTGGACAGGGACTGGAATGGATGGGCGGCATCATC CCCATCTTCGGCACCGCCAACTACGCCCAGAAATTCCAG GGCAGAGTGACCATCACCGCCGACGAGAGCACCAGCACC GCCTACATGGAACTGAGCAGCCTTCGAAGCGAGGACACC GCTGTGTATTACTGTGCGAGTTGTAGGTCTATCGAGGGCC CTACCCTGAGACAGTGGCTGGCCGCTCGAGCTTGTCTGG ATCTGATCGGGTACTACTACATGGACGTCTGGGGCAAAG GGACCACGGTCACCGTGTCCTCAG | 85 |

Example 9: Binding of Immunoglobulins Grafted with an Anti-TPO Receptor Peptide to the TPO Receptor HEK-293 cells were transfected with 4 peptide grafted antibody clones isolated as described in Example 8 or a negative control antibody. The expression vector expresses the IgGs as full length IgG1 with a transmembrane domain which links the antibody to the cell surface. The clones used were Anti-TpoR 1, 3, 4 and 5 from Table 3 (clones 1-4, respectively).

24 hrs post transfection, cells were trypsinized and incubated with 1 ug/ml biotinylated soluble TPOR (R&D Systems) or 1 ug/ml irrelevant biotinylated protein diluted in PBS+2% FBS. Following a 1 hr incubation, cells were pelleted, staining media was aspirated and the cells resuspended into 1 ug/ml R-Phycoerythrin labelled Streptavidin and 1 ug/ml Gt anti Human IgG Fc Alexa 647 conjugated antibody (Jackson Laboratories)+7AAD diluted into PBS+2% FBS and then incubated for an additional 1 hr.

Following the incubation cells were pelleted, staining media was aspirated, the cells resuspended into PBS+2% FBS and then analyzed by flow cytometry. The results are shown in FIG. 12A and show that all four of the peptide-grafted IgGs bound the TPO receptor and that the binding activity of the grafted peptide was affected by both the composition and the length of the flanking sequences.

Example 10: Preparation of Immunoglobulins Grafted with Anti-GLP-1 Receptor Peptides Full length human IgGs comprising a peptide targeted to the GLP-1 receptor were prepared using a recombination substrate incorporating the cassette shown in FIG. 11B, which includes 5' and 3' flanking sequences that include degenerative nucleotide combinations to generate diversity at the ends in addition to the diversity that is generated via V(D)J recombination. The peptide encoding sequences used in the cassette are shown in FIG. 11C [SEQ ID NOs:66-70]. These sequences encoded peptides derived from GLP-1 or exendin-4 as indicated. The flanking VH gene segments in the recombination substrate were VH1-2*01, VH1-3*01, VH1-8*01, VH1-18*01, VH1-46*01, VH1-24*01, VH1-45*01, VH1-58*01, VH1-69*01, VH1-f*01, VH2-5*01, VH2-26*01, VH2-70*01, VH3-7*01, VH3-11*01, VH3-21*01, VH3-23*01, VH3-30*01, VH3-33*01, VH3-48*01, VH3-53*01, VH3-9*01, VH3-13*01, VH3-20*01, VH3-43*01, VH3-64*01, VH3-66*01, VH3-74*01, VH3-d*01, VH3-15*01, VH3-49*01, VH3-72*01, VH3-73*01, VH4-30-1*01, VH4-30-4*01, VH4-31*01, VH4-39*01, VH4-59*01, VH4-61*01, VH4-4*02, VH4-28*01, VH4-30-2*01, VH4-34*01, VH4-b*01, VH5-51*01, VH5-a*01, VH6-1*01, VH7-4-1*01 and the flanking JH segments used were JH1, JH2, JH3, JH4, JH5, JH6.

Cells incorporating a tripartite V(D)J recombination substrate containing the cassette shown in FIG. 11B were cultured and induced to generate peptide grafted variants.

V(D)J recombined cells expressing the peptide-grafted antibodies were incubated with FLAG(DDK) tagged soluble GLP-1 receptor. The cells were subsequently stained with biotinylated mouse anti-FLAG antibody (Sigma Aldrich) and Streptavidin-PE to identify cells that had successfully bound the receptor and FACS sorted. cDNA from the FACS sorted cells were subsequently cloned into pcDNA to express the novel antibody as a full length IgG that would be secreted into the supernatant.

Greater than 100 anti-GLP1R binding variants were generated using this approach. Amino acid and nucleotide sequences of the peptide and flanking sequences for exemplary peptide-grafted immunoglobulins comprising an exendin-4 peptide isolated by this approach that were shown to bind to the GLP-1 receptor are shown in Tables 5A and 6 below. The VH and JH segments utilized in each case are shown in Table 5B.

TABLE 5B

VH and JH Segments Utilized in Anti GLPR 1-9

|  | VH Segment | JH Segment |
| --- | --- | --- |
| Anti GLP1R 1 | IGHV1-69*01 | IGHJ5 |
| Anti GLP1R 2 | IGHV1-69*01 | IGHJ2 |
| Anti GLP1R 3 | IGHV3-64*01 | IGHJ3 |
| Anti GLP1R 4 | IGHV3-64*01 | IGHJ3 |
| Anti GLP1R 5 | IGHV3-73*01 | IGHJ1 |
| Anti GLP1R 6 | IGHV1-69*01 | IGHJ3 |
| Anti GLP1R 7 | IGHV1-f*01 | IGHJ3 |
| Anti GLP1R 8 | IGHV1-69*01 | IGHJ5 |
| Anti GLP1R 9 | IGHV3-20*01 | IGHJ2 |

TABLE 5A

Amino Acid Sequences of Anti-GLP-1 Receptor Exendin-4 Peptides and Flanking Sequences (Anti-GLPR 1-9) [SEQ ID NOs: 72-80]

| | CDR3 AA Sequence | | | SEQ ID NO |
| --- | --- | --- | --- | --- |
| | 5' FLANK | Exendin sequences incorporated | 3' FLANK | |
| Anti GLP1R 1 | ARRASSV | HGEGTFTSDLSKQMEEEAVRLFIEWLK NGGPSSGAPPPS | DGSWFDP | 72 |
| Anti GLP1R 2 | AST | HGEGTFTSDLSKQMEEEAVRLFIEWLK NGGPSSGAPPPS | DWYFDL | 73 |
| Anti GLP1R 3 | A | HGEGTFTSDLSKQMEEEAVRLFIEWLK NGGPSSGAPPPS | SMLDAFDI | 74 |
| Anti GLP1R 4 | AREL | HGEGTFTSDLSKQMEEEAVRLFIEWLK NGGPSSGAPPPS | DDAFDI | 75 |
| Anti GLP1R 5 | TSF | HGEGTFTSDLSKQMEEEAVRLFIEWLK NGGPSSGAPPPS | QTLEYFQH | 76 |
| Anti GLP1R 6 | ARDG | HGEGTFTSDLSKQMEEEAVRLFIEWLK NGGPSSGAPPPS | WWPPDAFDI | 77 |
| Anti GLP1R 7 | ATD | -GEGTFTSDLSKQMEEEAVRLFIEWLKN GGPSSGAPPPS | MYDAFDI | 78 |
| Anti GLP1R 8 | ARL | HGEGTFTSDLSKQMEEEAVRLFIEWLK NGGPSSGAPPPS | LANNWFDP | 79 |
| Anti GLP1R 9 | ARDH | ---------LSKQMEEEAVRLFIEWLKNGGPSSGAP PPS | YWYFDL | 80 |

TABLE 6

Nucleotide Sequences of Anti-GLP-1 Receptor Exendin-4
Peptides and Flanking Sequences [SEQ ID NOs: 86-94]

| | Variable Gene Nucleotide Sequences (Heavy Chain) | SEQ ID NO |
|---|---|---|
| Anti GLP1R 1 | CAGGTGCAGCTGGTGCAGTCTGGCGCCGAAGTGAAGAAACCCG GCAGCAGCGTGAAGGTGTCCTGCAAGGCCAGCGGCGGCACCTT CAGCAGCTACGCCATCAGCTGGGTCCGCCAGGCTCCTGGACAG GGACTGGAATGGATGGGCGGCATCATCCCCATCTTCGGCACCG CCAACTACGCCCAGAAATTCCAGGGCAGAGTGACCATCACCGC CGACGAGAGCACCAGCACCGCCTACATGGAACTGAGCAGCCTT CGAAGCGAGGACACCGCTGTGTATTACTGTGCGAGACGGGCCT CTAGTGTGCATGGCGAGGGCACCTTCACCTCCGACCTGTCCAAA CAAATGGAAGAAGAAGCCGTCCGGCTGTTCATCGAATGGCTGA AAAATGGCGGCCCTTCCTCTGGCGCCCCTCCTCCTTCTGATGGA AGCTGGTTCGACCCCTGGGGCCAGGGAACCCTGGTCACCGTGTC CTCAG | 86 |
| Anti GLP1R 2 | CAGGTGCAGCTGGTGCAGTCTGGCGCCGAAGTGAAGAAACCCG GCAGCAGCGTGAAGGTGTCCTGCAAGGCCAGCGGCGGCACCTT CAGCAGCTACGCCATCAGCTGGGTCCGCCAGGCTCCTGGACAG GGACTGGAATGGATGGGCGGCATCATCCCCATCTTCGGCACCG CCAACTACGCCCAGAAATTCCAGGGCAGAGTGACCATCACCGC CGACGAGAGCACCAGCACCGCCTACATGGAACTGAGCAGCCTT CGAAGCGAGGACACCGCTGTGTATTACTGTGCGAGTACTCATG GCGAGGGCACCTTCACCTCCGACCTGTCCAAACAAATGGAAGA AGAAGCCGTCCGGCTGTTCATCGAATGGCTGAAAAATGGCGGC CCTTCCTCTGGCGCCCCTCCTCCTTCTGACTGGTACTTCGATCTC TGGGGCCGTGGCACCCTGGTCACTGTGTCCTCAG | 87 |
| Anti GLP1R 3 | GAAGTGCAGCTGGTGGAAAGCGGCGGAGGCCTGGTGCAGCCTG GCGGCAGCCTGAGACTGTCTTGCGCCGCCAGCGGCTTCACCTTC AGCAGCTACGCCATGCACTGGGTCCGCCAGGCCCCTGGCAAGG GACTGGAATACGTGTCCGCCATCAGCTCGAACGGCGGCAGCAC CTACTACGCCAACAGCGTGAAGGGCCGGTTCACCATCAGCCGG GACAACGCCAAGAACAGCCTGTACCTGCAGATGAACAGCCTGC GGGCCGAGGACACCGCCGTGTATTACTGTGCGCATGGCGAGGG CACCTTCACCTCCGACCTGTCCAAACAAATGGAAGAAGAAGCC GTCCGGCTGTTCATCGAATGGCTGAAAAATGGCGGCCCTTCCTC TGGCGCCCCTCCTCCTTCTAGTATGCTCGATGCTTTTGATATCTG GGGCCAAGGGACAATGGTCACCGTGTCCTCAG | 88 |
| Anti GLP1R 4 | GAAGTGCAGCTGGTGGAAAGCGGCGGAGGCCTGGTGCAGCCTG GCGGCAGCCTGAGACTGTCTTGCGCCGCCAGCGGCTTCACCTTC AGCAGCTACGCCATGTCACTGGGTCCGCCAGGCCCCTGGCAAGG GACTGGAATACGTGTCCGCCATCAGCTCGAACGGCGGCAGCAC CTACTACGCCAACAGCGTGAAGGGCCGGTTCACCATCAGCCGG GACAACAGCAAGAACACCCTGTACCTGCAGATGGGCAGCCTGC GGGCCGAGGATATGGCCGTGTATTACTGTGCGAGAGAGCTGCA TGGCGAGGGCACCTTCACCTCCGACCTGTCCAAACAAATGGAA GAAGAAGCCGTCCGGCTGTTCATCGAATGGCTGAAAAATGGCG GCCCTTCCTCTGGCGCCCCTCCTCCTTCTGATGATGCTTTTGATA TCTGGGGCCAAGGGACAATGGTCACCGTGTCCTCAG | 89 |
| Anti GLP1R 5 | GAAGTGCAGCTGGTGGAAAGCGGCGGAGGCCTGGTGCAGCCTG GCGGCAGCCTGAAACTGAGCTGCGCCGCCAGCGGCTTCACCTTT AGCGGCAGCGCCATGCACTGGGTCCGCCAGGCCTCTGGCAAGG GACTGGAATGGGTCGGACGGATTCGAAGCAAGGCCAACAGCTA CGCCACCGCCTACGCCGCCTCCGTGAAGGGCCGGTTCACCATCA GCCGGGACGACAGCAAGAACACCGCCTACCTGCAGATGAACAG CCTGAAAACCGAGGACACCGCCGTGTATTACTGTACTAGTTTTC ATGGCGAGGGCACCTTCACCTCCGACCTGTCCAAACAAATGGA AGAAGAAGCCGTCCGGCTGTTCATCGAATGGCTGAAAAATGGC GGCCCTTCCTCTGGCGCCCCTCCTCCTTCTCAGACGCTGGAATA CTTCCAGCACTGGGGCCAGGGCACCCTGGTCACCGTGTCCTCAG | 90 |
| Anti GLP1R 6 | CAGGTGCAGCTGGTGCAGTCTGGCGCCGAAGTGAAGAAACCCG GCAGCAGCGTGAAGGTGTCCTGCAAGGCCAGCGGCGGCACCTT CAGCAGCTACGCCATCAGCTGGGTCCGCCAGGCTCCTGGACAG GGACTGGAATGGATGGGCGGCATCATCCCCATCTTCGGCACCG CCAACTACGCCCAGAAATTCCAGGGCAGAGTGACCATCACCGC CGACGAGAGCACCAGCACCGCCTACATGGAACTGAGCAGCCTT CGAAGCGAGGACACCGCTGTGTATTACTGTGCGAGAGATGGTC ATGGCGAGGGCACCTTCACCTCCGACCTGTCCAAACAAATGGA AGAAGAAGCCGTCCGGCTGTTCATCGAATGGCTGAAAAATGGC GGCCCTTCCTCTGGCGCCCCTCCTCCTTCTTGGTGGCCACCCGAT GCTTTTGATATCTGGGGCCAAGGGACAATGGTCACCGTGTCCTC AG | 91 |

TABLE 6-continued

Nucleotide Sequences of Anti-GLP-1 Receptor Exendin-4
Peptides and Flanking Sequences [SEQ ID NOs: 86-94]

| | Variable Gene Nucleotide Sequences (Heavy Chain) | SEQ ID NO |
|---|---|---|
| Anti GLP1R 7 | GAAGTGCAGCTGGTGCAGTCTGGCGCCGAAGTGAAGAAACCTG GCGCCACCGTGAAGATCAGCTGCAAGGTGTCCGGCTACACCTTC ACCGACTACTACATGCACTGGGTGCAGCAGGCCCCTGGCAAGG GACTGGAATGGATGGGCCTGGTCGATCCCGAGGACGGCGAGAC AATCTACGCCGAGAAGTTCCAGGGCAGAGTGACCATCACCGCC GACACCAGCACCGACACCGCCTACATGGAACTGAGCAGCCTGC GGAGCGAGGACACCGCTGTGTATTACTGTGCAACAGATGGCGA GGGCACCTTCACCTCCGACCTGTCCAAACAAATGGAAGAAGAA GCCGTCCGGCTGTTCATCGAATGGCTGAAAAATGGCGGCCCTTC CTCTGGCGCCCCTCCTCCTTCTATGTATGATGCTTTTGATATCTG GGGCCAAGGGACAATGGTCACCGTGTCCTCAG | 92 |
| Anti GLP1R 8 | CAGGTGCAGCTGGTGCAGTCTGGCGCCGAAGTGAAGAAACCCG GCAGCAGCGTGAAGGTGTCCTGCAAGGCCAGCGGCGGCACCTT CAGCAGCTACGCCATCAGCTGGGTCCGCCAGGCTCCTGGACAG GGACTGGAATGGATGGGCGGCATCATCCCCATCTTCGGCACCG CCAACTACGCCCAGAAATTCCAGGGCAGAGTGACCATCACCGC CGACGAGAGCACCAGCACCGCCTACATGGAACTGAGCAGCCTT CGAAGCGAGGACACCGCTGTGTATTACTGTGCGCGGCTTCATGG CGAGGGCACCTTCACCTCCGACCTGTCCAAACAAATGGAAGAA GAAGCCGTCCGGCTGTTCATCGAATGGCTGAAAAATGGCGGCC CTTCCTCTGGCGCCCCTCCTCCTTCTTTGGCGAACAACTGGTTCG ACCCCTGGGGCCAGGGAACCCTGGTCACCGTGTCCTCAG | 93 |
| Anti GLP1R 9 | GAAGTGCAGCTGGTGGAAAGCGGAGGCGGAGTGGTTCGACCTG GCGGAAGCCTGAGACTGTCTTGCGCCGCCAGCGGCTTCACCTTT GACGACTACGGCATGAGCTGGGTCCGCCAGGCCCCTGGCAAGG GACTGGAATGGGTGTCCGGCATCAACTGGAACGGCGGCAGCAC CGGCTACGCCGACAGCGTGAAGGGCCGGTTCACCATCAGCCGG GACAACGCCAAGAACAGCCTGTACCTGCAGATGAACAGCCTGC GGGCCGAGGACACCGCCTTGTATCACTGTGCGAGAGATCACCT GTCCAAACAAATGGAAGAAGAAGCCGTCCGGCTGTTCATCGAA TGGCTGAAAAATGGCGGCCCTTCCTCTGGCGCCCCTCCTCCTTC TTACTGGTACTTCGATCTCTGGGGCCGTGGCACCCTGGTCACTG TGTCCTCAG | 94 |

Example 11: Binding of Immunoglobulins Grafted with an Anti-GLP-1 Receptor Peptide to Natively Expressed Full-Length GLP-1 Receptor To generate soluble peptide-grafted antibody for analysis, HEK-293 cells were transfected with 4 peptide grafted antibody clones isolated as described in Example 10. All four antibodies were derived from a recombination substrate using Exendin-4 1-39 (see FIG. 11C). The clones used were Anti-GLP1R 1, 6, 7 and 9 from Table 5 (clones 1-4, respectively). The negative control in this experiment was an irrelevant antibody. 24 hrs post transfection supernatants from the transfected cells were harvested and spun down at 14000 rpm for 5 min to remove cell debris.

In order to generate target cells expressing the native GLP-1 receptor, HEK293 cells were transfected with an expression construct which expresses full length GLP1R or mock transfected to serve as a negative control. 24 hrs later both the mock transfected and GLP1R transfected cells were trypsinized and incubated with the 250 ul supernatants isolated above. 1 ul of Gt anti-Human IgG R-Phycoerythrin conjugated antibody (Jackson Laboratories, 1 mg/ml Stock Solution) was added to the receptor transfected cells/supernatant mixture. After a 1 hr incubation cells were spun down, staining solution was aspirated, the cells resuspended into PBS+2% FBS+1 ug/ml 7AAD and analyzed by flow cytometry. The results are shown in FIG. 12B and show that that all four of the peptide-grafted IgGs bound the natively expressed full-length GLP-1 receptor.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

What is claimed is:

1. A method of generating a fusion protein which is an antibody, an antigen-binding domain of the antibody or a T-cell receptor (TCR) into which a heterologous polypeptide comprising a natural or synthetic polypeptide ligand has been grafted into a complementarity determining region (CDR) of the fusion protein, the fusion protein retaining protein-binding functionality of the polypeptide ligand, wherein the polypeptide ligand is capable of binding to a G protein-coupled receptor (GPCR), the method comprising:

(i) providing recombination-competent host cells that are capable of expressing RAG-1 and RAG-2 and which comprise at least one nucleic acid for expression of the fusion protein following in vitro recombination, the at least one nucleic acid comprising:

a first nucleic acid sequence comprising a first coding sequence encoding a first portion of the antibody, the antigen-binding domain or the TCR and further comprising a first recombination signal sequence (RSS);

a second nucleic acid sequence comprising a second RSS capable of functional recombination with the first RSS, a second coding sequence encoding the polypeptide comprising the ligand and further comprising a third RSS; and a third nucleic acid sequence comprising a third coding sequence encoding a second portion of the antibody, the antigen-binding domain or the TCR, the third nucleic acid sequence further comprising a fourth RSS capable of functional recombination with the third RSS;

wherein the first nucleic acid sequence, the second nucleic acid sequence and the third nucleic acid sequence together comprise a tripartite recombination substrate capable of recombining to insert the second coding sequence into a polynucleotide sequence encoding the CDR or to replace an immunoglobulin D segment-encoding sequence within the polynucleotide sequence encoding the CDR with the second coding sequence, the recombination generating sequence diversity at both recombination junctions;

(ii) culturing the recombination-competent host cells in vitro under conditions allowing:

(a) recombination of the first RSS with the second RSS and the third RSS with the fourth RSS to generate a library of chimeric polynucleotide variants comprising the first coding sequence, the second coding sequence and the third coding sequences; and (b) expression of the library of chimeric polynucleotides so as to generate a library of fusion protein variants; and (iii) screening the library of fusion protein variants using a functional assay to identify the fusion protein having retained protein binding functionality of the polypeptide ligand.

2. The method according to claim 1, wherein the first nucleic acid sequence, the second nucleic acid sequence and the third nucleic acid sequence are comprised within a single polynucleotide.

3. The method according to claim 2, wherein the first nucleic acid sequence and the second nucleic acid sequence further comprise a nucleotide sequence encoding a polypeptide linker and the first RSS and the second RSS are positioned within or proximal to the nucleotide sequence encoding the polypeptide linker, whereby recombination in step (ii) introduces sequence diversity into the nucleotide sequence encoding the polypeptide linker.

4. The method according to claim 1, wherein the first portion and the second portion of the antibody, the antigen-binding domain or the TCR are from an antibody or an antigen-binding domain.

5. The method according to claim 4, wherein the first portion and the second portion of the antibody, the antigen-binding domain or the TCR are from a heavy chain of the antibody or the antigen-binding domain.

6. The method according to claim 4, wherein the first portion and the second portion of the antibody, the antigen-binding domain or the TCR are from a light chain of the antibody or the antigen-binding domain.

7. The method according to claim 4, wherein the CDR is a CDR3 and the first RSS and the fourth RSS are positioned within a region encoding the CDR3.

8. The method according to claim 1, wherein one or more of the first nucleic acid sequence, the second nucleic acid sequence and the third nucleic acid sequence further comprises flanking sequences adjacent to, respectively: the first RSS; the second RSS and/or the third RSS; and the fourth RSS.

9. The method according to claim 1, wherein one or both of the first nucleic acid sequence and the third nucleic acid sequence further comprises additional coding sequences that encode a membrane anchor domain peptide.

10. The method according to claim 1, wherein the recombination-competent host cells are capable of expressing TdT.

11. The method according to claim 2, wherein the single polynucleotide is stably integrated into the genomes of the recombination-competent host cells.

12. The method according to claim 11, wherein the single polynucleotide is stably integrated into the genome of each of the recombination-competent host cells as a single copy.

13. The method according to claim 1, wherein expression of at least one of the RAG-1 and the RAG-2 is under inducible control in the recombination-competent host cells, and wherein step (ii) comprises inducing expression of the at least one of the RAG-1 and the RAG-2.

14. The method according to claim 1, wherein the polypeptide ligand is a natural ligand.

15. The method according to claim 1, wherein the polypeptide ligand that is capable of binding to the GPCR is derived from GLP-1, exendin-4 or TPO.

16. The method according to claim 1, wherein the polypeptide ligand that is capable of binding to the GPCR has the sequence set forth in SEQ ID NO:38, 43, 71 or 73-80, or a fragment thereof.

17. The method according to claim 1, wherein the fusion protein comprises a full length IgG scaffold.

* * * * *